US012383547B2

(12) United States Patent
Pulley et al.

(10) Patent No.: US 12,383,547 B2
(45) Date of Patent: Aug. 12, 2025

(54) METHODS OF TREATMENT FOR A KIDNEY DISEASE

(71) Applicant: Vanderbilt University, Nashville, TN (US)

(72) Inventors: Jill M. Pulley, Nashville, TN (US); Jana K. Shirey-Rice, Brentwood, TN (US); Rebecca N. Jerome, Nashville, TN (US); Frederic T. Billings, IV, Nashville, TN (US); Nicole M. Zaleski, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 495 days.

(21) Appl. No.: 18/003,644

(22) PCT Filed: Jul. 1, 2021

(86) PCT No.: PCT/US2021/040204
§ 371 (c)(1),
(2) Date: Dec. 28, 2022

(87) PCT Pub. No.: WO2022/006470
PCT Pub. Date: Jan. 6, 2022

(65) Prior Publication Data
US 2023/0310411 A1    Oct. 5, 2023

Related U.S. Application Data

(60) Provisional application No. 63/048,623, filed on Jul. 6, 2020, provisional application No. 63/047,217, filed on Jul. 1, 2020.

(51) Int. Cl.
*A61K 31/47*    (2006.01)
*A61P 13/12*    (2006.01)

(52) U.S. Cl.
CPC .............. *A61K 31/47* (2013.01); *A61P 13/12* (2018.01)

(58) Field of Classification Search
CPC .............................. A61K 31/47; A61P 13/12
See application file for complete search history.

(56) References Cited

U.S. PATENT DOCUMENTS

| | | |
|---|---|---|
| 5,441,951 A | 8/1995 | Serhan |
| 5,565,473 A | 10/1996 | Belley et al. |
| 5,648,512 A | 7/1997 | Serhan |
| 6,048,897 A | 4/2000 | Serhan |
| 6,316,648 B1 | 11/2001 | Serhan |
| 6,569,075 B2 | 5/2003 | Serhan |
| 6,620,919 B2 | 9/2003 | Serhan |
| 6,635,776 B2 | 10/2003 | Serhan |
| 6,653,493 B2 | 11/2003 | Serhan |
| 6,750,360 B2 | 6/2004 | Serhan |
| 6,887,901 B1 | 5/2005 | Serhan |
| 7,189,853 B2 | 3/2007 | Sundaram et al. |
| 7,288,569 B2 | 10/2007 | Serhan |
| 7,294,728 B2 | 11/2007 | Serhan |
| 7,498,334 B2 | 3/2009 | Eggenweiler et al. |
| 7,741,369 B2 | 6/2010 | Serhan |
| 7,772,433 B2 | 8/2010 | Dalton et al. |
| 7,825,271 B2 | 11/2010 | Serhan |
| 8,007,830 B2 | 8/2011 | Down |
| 8,080,682 B2 | 12/2011 | Dalton et al. |
| 8,158,828 B2 | 4/2012 | Dalton et al. |
| 8,426,465 B2 | 4/2013 | Dalton et al. |
| 8,637,706 B2 | 1/2014 | Dalton et al. |
| 8,846,756 B2 | 9/2014 | Dalton et al. |
| 8,853,266 B2 | 10/2014 | Dalton et al. |
| 8,936,825 B2 | 1/2015 | Myers et al. |
| 9,068,991 B2 | 6/2015 | Goix et al. |
| 9,078,888 B2 | 7/2015 | Dalton et al. |
| 9,260,416 B2 | 2/2016 | Roppe et al. |
| 9,561,191 B2 | 2/2017 | Myers et al. |
| 9,669,025 B2 | 6/2017 | May |
| 9,669,026 B2 | 6/2017 | May |
| 9,884,038 B2 | 2/2018 | Dalton et al. |
| 9,889,110 B2 | 2/2018 | Dalton et al. |
| 10,053,418 B2 | 8/2018 | Dalton et al. |
| 10,201,537 B2 | 2/2019 | May |
| 10,206,919 B2 | 2/2019 | May |
| 2001/0031882 A1 | 10/2001 | Serhan |

(Continued)

FOREIGN PATENT DOCUMENTS

| AU | 765343 B2 | 9/2003 |
|---|---|---|
| AU | 2013219238 A1 | 9/2013 |

(Continued)

OTHER PUBLICATIONS

Abdel-Raheem IT, et al. Renoprotective effects of montelukast, a cysteinyl leukotriene receptor antagonist, against methotrexate-induced kidney damage in rats. Naunyn Schmiedebergs Arch Pharmacol. Apr. 2014;387(4):341-353.

Abdulamir AS, et al. Different inflammatory mechanisms in lungs of severe and mild asthma: crosstalk of NF-kappa-B, TGFbeta1, Bax, Bcl-2, IL-4 and IgE. Scand J Clin Lab Invest. 2009;69(4):487-495.

Acker MA, et al. Mitral-valve repair versus replacement for severe ischemic mitral regurgitation. N Engl J Med. Jan. 2, 2014;370(1):23-32.

Adzhubei I, et al. Predicting functional effect of human missense mutations using PolyPhen-2. Curr Protoc Hum Genet Editor Board Jonathan Haines Al. Jan. 2013;Chapter 7:Unit7.20, pp. 1-52.

(Continued)

*Primary Examiner* — Michael B. Pallay
(74) *Attorney, Agent, or Firm* — Michael Best & Friedrich LLP

(57) ABSTRACT

Disclosed herein are methods for preventing, treating, or reducing the severity of a cardiac surgery-associated acute kidney injury and extracorporeal membrane oxygenation-associated acute kidney injury in a subject. The methods include administering to the subject a therapeutically effective amount of a leukotriene receptor antagonist compound.

24 Claims, 3 Drawing Sheets

(56) References Cited

U.S. PATENT DOCUMENTS

| | | |
|---|---|---|
| 2002/0010351 A1 | 1/2002 | Serhan |
| 2002/0082435 A1 | 6/2002 | Serhan |
| 2002/0091279 A1 | 7/2002 | Serhan |
| 2002/0111505 A1 | 8/2002 | Serhan |
| 2003/0032827 A1 | 2/2003 | Serhan |
| 2003/0134901 A1 | 7/2003 | Serhan |
| 2005/0059686 A1 | 3/2005 | Eggenweiler et al. |
| 2005/0148668 A1 | 7/2005 | Serhan |
| 2006/0069158 A1 | 3/2006 | Serhan |
| 2007/0265296 A1 | 11/2007 | Dalton et al. |
| 2007/0281906 A1 | 12/2007 | Dalton et al. |
| 2008/0057068 A1 | 3/2008 | Dalton et al. |
| 2008/0076828 A1 | 3/2008 | Dalton et al. |
| 2008/0076829 A1 | 3/2008 | Dalton et al. |
| 2009/0030036 A1 | 1/2009 | Dalton et al. |
| 2009/0258945 A1 | 10/2009 | Serhan |
| 2009/0270498 A1 | 10/2009 | Serhan |
| 2011/0237664 A1 | 9/2011 | Dalton et al. |
| 2012/0076921 A1 | 3/2012 | Myers et al. |
| 2012/0136052 A1 | 5/2012 | Dalton et al. |
| 2012/0157539 A1 | 6/2012 | Dalton et al. |
| 2012/0277311 A1 | 11/2012 | Serhan |
| 2013/0029948 A1 | 1/2013 | Roppe et al. |
| 2013/0034562 A1 | 2/2013 | Dalton et al. |
| 2013/0324602 A1 | 12/2013 | Dalton et al. |
| 2014/0011774 A1 | 1/2014 | Dalton et al. |
| 2014/0083180 A1 | 3/2014 | Schaefer et al. |
| 2014/0134274 A1 | 5/2014 | Steiner et al. |
| 2014/0296149 A1 | 10/2014 | Zhang et al. |
| 2015/0150825 A1 | 6/2015 | Myers et al. |
| 2015/0272874 A1 | 10/2015 | Sawa et al. |
| 2015/0352101 A1 | 12/2015 | May |
| 2016/0089356 A1 | 3/2016 | Dalton et al. |
| 2016/0166530 A1 | 6/2016 | Dalton et al. |
| 2017/0172979 A1 | 6/2017 | Rubinstein et al. |
| 2017/0182117 A1 | 6/2017 | Wilson et al. |
| 2017/0231980 A1 | 8/2017 | May |
| 2017/0240506 A1 | 8/2017 | Dalton et al. |
| 2017/0266199 A1* | 9/2017 | Berger ............... A61P 11/00 |
| 2018/0064682 A1 | 3/2018 | Rubinstein et al. |
| 2018/0071242 A1 | 3/2018 | Dalton et al. |
| 2018/0273470 A1 | 9/2018 | Narayanan et al. |
| 2018/0344814 A1 | 12/2018 | Wilson |

FOREIGN PATENT DOCUMENTS

| | | |
|---|---|---|
| AU | 2013200516 A1 | 9/2015 |
| AU | 2015264895 A1 | 6/2017 |
| EP | 0703897 B1 | 8/1997 |
| EP | 0791576 A2 | 8/2008 |
| EP | 2913047 A1 | 9/2015 |
| WO | WO 1994029262 A1 | 12/1994 |
| WO | WO 1998011049 A1 | 3/1998 |
| WO | WO 2000050639 A2 | 8/2000 |
| WO | WO 2003066598 A1 | 8/2003 |
| WO | WO 2008008433 A1 | 1/2008 |
| WO | WO 2008024456 A2 | 7/2008 |
| WO | WO 2008091555 A2 | 7/2008 |
| WO | WO 2008127717 A1 | 10/2008 |
| WO | WO 2008130464 A1 | 10/2008 |
| WO | WO 2008130571 A1 | 10/2008 |
| WO | WO 2009122187 A2 | 10/2009 |
| WO | WO 2010021697 A2 | 2/2010 |
| WO | WO 2010077882 A2 | 7/2010 |
| WO | WO 2010077883 A2 | 7/2010 |
| WO | WO 2010141761 A2 | 12/2010 |
| WO | WO 2011017350 A2 | 2/2011 |
| WO | WO 2011041462 A2 | 4/2011 |
| WO | WO 2011041729 A2 | 4/2011 |
| WO | WO 2011073231 A1 | 6/2011 |
| WO | WO 2011159550 A2 | 12/2011 |
| WO | WO 2012024620 A2 | 2/2012 |
| WO | WO 2012040262 A1 | 3/2012 |
| WO | WO 2012078593 A2 | 6/2012 |
| WO | WO 2012078805 A1 | 6/2012 |
| WO | WO 2012171900 A1 | 6/2012 |
| WO | WO 2012139081 A2 | 10/2012 |
| WO | WO 2012139093 A2 | 10/2012 |
| WO | WO 2013012915 A1 | 1/2013 |
| WO | WO 2013012918 A1 | 1/2013 |
| WO | WO 2013032591 A1 | 3/2013 |
| WO | WO 2013119871 A1 | 8/2013 |
| WO | WO 2013154878 A1 | 10/2013 |
| WO | WO 2014097151 A2 | 6/2014 |
| WO | WO 2014145873 A2 | 9/2014 |
| WO | WO 2014164285 A2 | 10/2014 |
| WO | WO 2015008230 A1 | 1/2015 |
| WO | WO 2015042052 A1 | 3/2015 |
| WO | WO 2015042053 A1 | 3/2015 |
| WO | WO 2015051244 A1 | 4/2015 |
| WO | WO 2015058143 A1 | 4/2015 |
| WO | WO 2015061724 A1 | 4/2015 |
| WO | WO 2015125138 A1 | 8/2015 |
| WO | WO 2015143012 A1 | 9/2015 |
| WO | WO 2015154023 A1 | 10/2015 |
| WO | WO 2015162558 A1 | 10/2015 |
| WO | WO 2015175171 A1 | 11/2015 |
| WO | WO 2016027253 A1 | 2/2016 |
| WO | WO 2016153948 A1 | 9/2016 |
| WO | WO 2017048702 A1 | 3/2017 |
| WO | WO 2017083371 A1 | 5/2017 |
| WO | WO 2017083470 A1 | 5/2017 |
| WO | WO 2017207385 A1 | 12/2017 |
| WO | WO 2018060072 A1 | 4/2018 |
| WO | WO 2018060174 A1 | 4/2018 |
| WO | WO 2018170480 A1 | 9/2018 |
| WO | WO 2018232122 A1 | 12/2018 |

OTHER PUBLICATIONS

Adzhubei IA, et al. A method and server for predicting damaging missense mutations. Nat Methods. Apr. 2010;7(4):248-249.

Ailawadi G, et al. Exclusion of the left atrial appendage with a novel device: early results of a multicenter trial. J Thorac Cardiovasc Surg. Nov. 2011;142(5):1002-1009.

Akcay A, et al. Mediators of Inflammation in Acute Kidney Injury. Mediators Inflamm [Internet]. 2009: 137072.

Al Saadi MM, et al. Effects of Montelukast on free radical production in whole blood and isolated human polymorphonuclear neutrophils (PMNs) in asthmatic children. Saudi Pharm J. Oct. 2011;19(4):215-220.

Al-Amran, Fadhil G., Najah R. Hadi, and Lubna Abdul-Sattar Mahdi. "Effect of montelukast on myocardial ischemia reperfusion injury after coronary artery bypass graft surgery." World Heart Journal 8.3 (2016): 261-270.

Allen SP, et al. Enhanced excretion of urinary leukotriene E4 in coronary artery disease and after coronary artery bypass surgery. Coron Artery Dis. Oct. 1993;4(10):899-904.

Altraja S, et al. Synthesis of tenascin and laminin beta2 chain in human bronchial epithelial cells is enhanced by cysteinyl leukotrienes via CysLTI receptor. Respir Res. May 26, 2008;9:44.

Antczak A, et al. Exhaled eicosanoids and biomarkers of oxidative stress in exacerbation of chronic obstructive pulmonary disease. Arch Med Sci AMS. May 9, 2012;8(2):277-285.

Arm JP. Leukotriene generation and clinical implications. Allergy Asthma Proc. Feb. 2004;25(1):37-42.

Aslani A, et al. Design, formulation, and physicochemical evaluation of montelukast orally disintegrating tablet. Int J Prev Med. 2016;7(1):120.

Atakan A, et al. Renal protective effects of leukotriene receptor blockers in an experimental model of cyclosporine nephrotoxicity. Transplant Proc. Feb. 2008;40(1):279-284.

Badr KF, et al. Lipoxygenase products in normal and diseased glomeruli. Ann N Y Acad Sci. Nov. 15, 1994;744:216-228.

Baldwin DS, et al. Renal failure and interstitial nephritis due to penicillin and methicillin. N Engl J Med. Dec. 5, 1968;279(23):1245-1252.

Bandaru S, et al. Structure based virtual screening of ligands to identify cysteinyl leukotriene receptor 1 antagonist. Bioinformation. Oct. 30, 2014;10(10):652-657.

(56) References Cited

OTHER PUBLICATIONS

Bao Y-W, et al. Kidney disease models: tools to identify mechanisms and potential therapeutic targets. Zool Res. 2018 18;39(2):72-86.
Baraldi E, et al. Cysteinyl leukotrienes and 8-isoprostane in exhaled breath condensate of children with asthma exacerbations. Thorax. Jun. 2003;58(6):505-509.
Basile DP, et al. Pathophysiology of Acute Kidney Injury. Compr Physiol. Apr. 2012,2(2):1303-1353.
Bavaria JE, et al. The St Jude Medical Trifecta aortic pericardial valve: results from a global, multicenter, prospective clinical study. J Thorac Cardiovasc Surg. Feb. 2014;147(2):590-597.
Beytur A, et al. Beneficial effects of montelukast against cisplatin-induced acute renal damage in rats. Ren Fail. 2012;34(3):343-349.
Billings FT, et al. Clinical trial endpoints in acute kidney injury. Nephron Clin Pract. 2014;127(1-4):89-93.
Billings FT, et al. Comparative effects of angiotensin receptor blockade and ACE inhibition on the fibrinolytic and inflammatory responses to cardiopulmonary bypass. Clin Pharmacol Ther. Jun. 2012;91(6):1065-1073.
Billings FT, et al. Early postoperative statin therapy is associated with a lower incidence of acute kidney injury after cardiac surgery. J Cardiothorac Vasc Anesth. Dec. 2010;24(6):913-920.
Billings FT, et al. High-Dose Perioperative Atorvastatin and Acute Kidney Injury Following Cardiac Surgery: A Randomized Clinical Trial. JAMA. Mar. 1, 2016;315(9):877-888.
Billings FT, et al. Obesity and Oxidative Stress Predict AKI after Cardiac Surgery. J Am Soc Nephrol. Jul. 2012;23(7):1221-1228.
Billings FT, et al. Perioperative intravenous acetaminophen attenuates lipid peroxidation in adults undergoing cardiopulmonary bypass: a randomized clinical trial. PLoS One. 2015;10(2):e0117625.
Billings FT. "Acute kidney injury following cardiac surgery: a clinical model." Nephron 143.3 (2019): 202-206.
Bloom B. Repurposing Social Impact Bonds for Medicine. Stanford Social Innovation Review [Internet]. Apr. 8, 2016; Available from: https://ssir.org/articles/entry/repurposing_social_impact_bonds_for_medicine (3 pages).
Bowton E, et al. "Biobanks and electronic medical records: enabling cost-effective research." Science translational medicine 6.234 (2014): 234cm3-234cm3.
Bowton E, et al. Phenotype-Driven Plasma Biobanking Strategies and Methods. Journal of Personalized Medicine. May 14, 2015;5(2):140-152.
Brooks, P. M., et al. "Nonsteroidal antiinflammatory drugs-differences and similarities." New England Journal of Medicine 324.24 (1991): 1716-1725.
Bundgaard, H. et al. "Esters of N, N-disubstituted 2-hydroxyacetamides as a novel highly biolabile prodrug type for carboxylic acid agents." Journal of medicinal chemistry 30.3 (1987): 451-454.
Busse WW. Leukotrienes and Inflammation. Am J Respir Crit Care Med. Jun. 1, 1998;157(6):S210-S213.
Butterly DW, et al. A role for leukotrienes in cyclosporine nephrotoxicity. Kidney Int. Jun. 2000;57(6):2586-2593.
Byrne DW, et al. Clinical and translational research studios: a multidisciplinary internal support program. Acad Med. Aug. 2012;87(8):1052-1059.
Cai C, et al. Relationship between urinary cysteinyl leukotriene E4 levels and clinical response to antileukotriene treatment in patients with asthma. Lung. Apr. 2007;185(2):105-112.
Challa AP, et al. Systematically Prioritizing Candidates in Genome-Based Drug Repurposing. Assay Drug Dev Technol. Dec. 2019; 17(8):352-363.
Challa AP, et al. Systematically Prioritizing Targets in Genome-Based Drug Repurposing. Proceedings of the 2018 ACM International Conference on Bioinformatics, Computational Biology, and Health Informatics—BCB '18 [Internet]. Washington, DC, USA: ACM Press; 2018. p. 543-543.
Chaney MA, et al. Protamine Administration via the Ascending Aorta May Prevent Cardiopulmonary Instability. J Cardiothorac Vasc Anesth. Jun. 2016;30(3):647-655.

Chawla LS, et al. Association between AKI and long-term renal and cardiovascular outcomes in United States veterans. Clin J Am Soc Nephrol. Mar. 2014;9(3):448-456.
Chawla LS, et al. The severity of acute kidney injury predicts progression to chronic kidney disease. Kidney International. Jun. 2011;79(12):1361-1369.
Chen Y, et al. Formulation and evaluation of a montelukast sodium orally disintegrating tablet with a similar dissolution profile as the marketed product. Pharm Dev Technol. Mar. 2017;22(2):168-172.
Chertow GM, et al. Independent association between acute renal failure and mortality following cardiac surgery. Am J Med. Apr. 1998;104(4):343-348.
Chertow GM, et al. Preoperative renal risk stratification. Circulation. Feb. 18, 1997;95(4):878-884.
Chibana K, et al. Up-regulation of cysteinyl leukotriene 1 receptor by IL-13 enables human lung fibroblasts to respond to leukotriene C4 and produce eotaxin. J Immunol Baltim Md 1950. Apr. 15, 2003;170(8):4290-4295.
Choby JE, et al. A Phenome-Wide Association Study Uncovers a Pathological Role of Coagulation Factor X during Acinetobacter baumannii Infection. Infect Immun. Mar. 2019;87(5) (15 pages).
Ciprandi G, et al. Nasal cytokine modulation by montelukast in allergic children: a pilot study. Eur Ann Allergy Clin Immunol. Oct. 2003;35(8):295-299.
Colgan SP, et al. Adenosine and Hypoxia-Inducible Factor Signaling in Intestinal Injury and Recovery. Annu Rev Physiol [Internet]. 2012;74 (28 pages).
Collard CD, et al. Pathophysiology, Clinical Manifestations, and Prevention of Ischemia-Reperfusion Injury. Anesthesiology. The American Society of Anesthesiologists; Jun. 1, 2001;94(6):1133-1138.
Collins FS. Seeking a Cure for One of the Rarest Diseases: Progeria. Circulation. Jul. 12, 2016;134(2):126-129.
Conlon PJ, et al. Acute renal failure following cardiac surgery. Nephrol Dial Transplant. May 1999;14(5):1158-1162.
Coskun AK, et al. The effects of montelukast on antioxidant enzymes and proinflammatory cytokines on the heart, liver, lungs, and kidneys in a rat model of cecal ligation and puncture-induced sepsis. Scientific WorldJournal. Jul. 7, 2011;11:1341-1356.
Crick FHC, On protein synthesis. Symposium of the Society of Experimental Biology. 1958 12; 140.
Cummings JJ, et al. Intraoperative prediction of cardiac surgery-associated acute kidney injury using urinary biomarkers of cell cycle arrest. J Thorac Cardiovasc Surg. Apr. 2019;157(4):1545-1553.e5.
Cysltr1 (human) | Gene Target—PubChem [Internet]. 2016. Available from: https://pubchem.ncbi.nlm.nih.gov/target/gene/CYSLTR1/human. 19 pages.
Cysteinyl leukotriene receptor 1 (human) | Protein Target—PubChem [Internet]. 2017. Available from: https://pubchem.ncbi.nlm.nih.gov/target/protein/Q9Y271 (20 pages).
De Caestecker et al. Translating Knowledge Into Therapy for Acute Kidney Injury. Semin Nephrol. Jan. 2018;38(1):88-97.
De Prost et al. Changes in cysteinyl leukotrienes during and after cardiac surgery with cardiopulmonary bypass in patients with and without chronic obstructive pulmonary disease. J Thorac Cardiovasc Surg. Jun. 2011;141(6):1496-1502.e3.
Del Duca D, et al. Renal failure after cardiac surgery: timing of cardiac catheterization and other perioperative risk factors. Ann Thorac Surg. Oct. 2007;84(4):1264-1271.
Delaney JT, et al. Predicting clopidogrel response using DNA samples linked to an electronic health record. Clin Pharmacol Ther. Feb. 2012;91(2):257-263.
Denny JC, et al. Identification of Genomic Predictors of Atrioventricular Conduction: Using Electronic Medical Records as a Tool for Genome Science. Circulation. Nov. 16, 2010;122(20):2016-2021.
Denny JC, et al. PheWAS: demonstrating the feasibility of a phenome-wide scan to discover gene-disease associations. Bioinformatics. May 1, 2010;26(9):1205-1210.
Denny JC, et al. Systematic comparison of phenome-wide association study of electronic medical record data and genome-wide association study data. Nat Biotechnol. Dec. 2013;31(12):1102-1110.

(56) References Cited

OTHER PUBLICATIONS

Denny JC, et al. Variants near FOXE1 are associated with hypothyroidism and other thyroid conditions: using electronic medical records for genome- and phenome-wide studies. Am J Hum Genet. Oct. 7, 2011;89(4):529-542.

Depré M, et al. Effect of multiple doses of montelukast, a CysLT1 receptor antagonist, on digoxin pharmacokinetics in healthy volunteers. J Clin Pharmacol. Sep. 1999;39(9):941-944.

Derose JJ, et al. Pacemaker Implantation After Mitral Valve Surgery With Atrial Fibrillation Ablation. J Am Coll Cardiol. May 21, 2019;73(19):2427-2435.

Dhawan R, et al. Prospective, randomized clinical trial comparing use of intraoperative transesophageal echocardiography to standard care during radical cystectomy. Ann Card Anaesth. Sep. 2018;21(3):255-261.

Di Capite J, et al. Targeting Ca2+ release-activated Ca2+ channel channels and leukotriene receptors provides a novel combination strategy for treating nasal polyposis. Journal of Allergy and Clinical Immunology. Nov. 2009;124(5):1014-1021.e3.

Diamant Z, et al. Montelukast in the treatment of asthma and beyond. Expert Rev Clin Immunol. Nov. 1, 2009;5(6):639-658.

Diamant Z, et al. The effect of inhaled leukotriene D4 and methacholine on sputum cell differentials in asthma. Am J Respir Crit Care Med. Apr. 1997;155(4):1247-1253.

Dockhorn RJ, et al. Comparison of the effects of intravenous and oral montelukast on airway function: a double blind, placebo controlled, three period, crossover study in asthmatic patients. Thorax. Apr. 2000,55(4):260-265.

Doyle JF, et al. Acute kidney injury: short-term and long-term effects. Critical Care. Jul. 4, 2016;20(1):188.

Duncan AE, et al. Effect of 6% hydroxyethyl starch 130/0.4 on kidney and haemostatic function in cardiac surgical patients: a randomised controlled trial. Anaesthesia. Sep. 2020;75(9):1180-1190.

Duncan AE, et al. Hyperinsulinemic Normoglycemia Does Not Meaningfully Improve Myocardial Performance during Cardiac Surgery: A Randomized Trial. Anesthesiology. Aug. 2015;123(2):272-287.

Duncan AE, et al. Hyperinsulinemic Normoglycemia during Cardiac Surgery Reduces a Composite of 30-day Mortality and Serious In-hospital Complications: A Randomized Clinical Trial. Anesthesiology. Jun. 2018;128(6):1125-1139.

Dvashe, et al. Leukotriene C4 is the major trigger of stress-induced oxidative DNA damage. Nat Commun. Dec. 11, 2015;6:10112.

Ellis JL, et al. Role of cysteinyl-leukotrienes and histamine in mediating intrinsic tone in isolated human bronchi. Am J Respir Crit Care Med. Jan. 1994;149(1):118-122.

Eltzschig HK, et al. Ischemia and reperfusion-from mechanism to translation. Nature Medicine. Nature Publishing Group; Nov. 2011;17(11):1391-1401.

Ely EW, et al. Delirium in Mechanically Ventilated Patients: Validity and Reliability of the Confusion Assessment Method for the Intensive Care Unit (CAM-ICU). JAMA. Dec. 5, 2001;286(21):2703-2710.

Ericson-Neilsen W, et al. Steroids: pharmacology, complications, and practice delivery issues. Ochsner J. 2014;14(2):203-207.

Evans SR, et al. Desirability of Outcome Ranking (DOOR) and Response Adjusted for Duration of Antibiotic Risk (RADAR). Clin Infect Dis. Oxford Academic; Sep. 1, 2015;61(5):800-806.

Evans SR, et al. Methodologies for pragmatic and efficient assessment of benefits and harms: Application to the SOCRATES trial. Clin Trials. Dec. 2020;17(6):617-626.

Farkouh ME, et al. Strategies for multivessel revascularization in patients with diabetes. N Engl J Med. Dec. 20, 2012;367(25):2375-2384.

FDA Center for Drug Evaluation and Research. FDA requires Boxed Warning about serious mental health side effects for asthma and allergy drug montelukast (Singulair); advises restricting use for allergic rhinitis. FDA [Internet]. FDA; Mar. 2020; Available from: https://www.fda.gov/drugs/drug-safety-and-availability/fda-requires-boxed-warning-about-serious-mental-health-side-effects-asthma-and-allergy-drug (8 pages).

FDA. Drug Approval Package: Singulair (Montelukast Sodium) NDA# 020829 [Internet]. 2005. Available from: https://www.accessdata.fda.gov/drugsatfda_docs/nda/98/020829s000_SingulairTOC.cfm (348 pages).

Fleming GA, et al. Angiotensin-converting enzyme inhibition alters the inflammatory and fibrinolytic response to cardiopulmonary bypass in children. Pediatr Crit Care Med. Sep. 2011;12(5):532-538.

Forrest JK, et al. Early Outcomes With the Evolut PRO Repositionable Self-Expanding Transcatheter Aortic Valve With Pericardial Wrap. JACC Cardiovasc Interv. Jan. 22, 2018;11(2):160-168.

Gad AM, et al. Renoprotective effects of montelukast in an experimental model of cisplatin nephrotoxicity in rats. J Biochem Mol Toxicol. Dec. 2017;31(12).

Gadaleta D, et al. Neutrophil leukotriene generation increases after cardiopulmonary bypass. J Thorac Cardiovasc Surg. Oct. 1994;108(4):642-647.

Gamble C, et al. Guidelines for the Content of Statistical Analysis Plans in Clinical Trials. JAMA. Dec. 19, 2017;318(23):2337-2343.

Garg AX, et al. Safety of a Restrictive versus Liberal Approach to Red Blood Cell Transfusion on the Outcome of AKI in Patients Undergoing Cardiac Surgery: A Randomized Clinical Trial. J Am Soc Nephrol. Jul. 2019;30(7):1294-1304.

Garg AX, et al. Steroids in caRdiac Surgery (SIRS) trial: acute kidney injury substudy protocol of an international randomised controlled trial. BMJ Open. Mar. 5, 2014;4(3):e004842.

Gerlach RM, et al. Intraoperative Use of Nondepolarizing Neuromuscular Blocking Agents During Cardiac Surgery and Postoperative Pulmonary Complications: A Prospective Randomized Trial. J Cardiothorac Vasc Anesth. Jun. 2019;33(6):1673-1681.

Gialdini G, et al. Perioperative atrial fibrillation and the long-term risk of ischemic stroke. JAMA. Aug. 13, 2014;312(6):616-622.

Gillinov AM, et al. Rate Control versus Rhythm Control for Atrial Fibrillation after Cardiac Surgery. N Engl J Med. May 19, 2016;374(20):1911-1921.

Giustino G, et al. Left Main Revascularization With PCI or CABG in Patients With Chronic Kidney Disease: EXCEL Trial. J Am Coll Cardiol. Aug. 14, 2018;72(7):754-765.

Giustino G, et al. Mortality After Repeat Revascularization Following PCI or CABG for Left Main Disease: The EXCEL Trial. JACC Cardiovasc Interv. Feb. 10, 2020;13(3):375-387.

Golba K, et al. Mechanisms of functional mitral regurgitation in ischemic cardiomyopathy determined by transesophageal echocardiography (from the Surgical Treatment for Ischemic Heart Failure Trial). Am J Cardiol. Dec. 1, 2013;112(11):1812-1818.

Goldman S, et al. Midterm, multicenter clinical and hemodynamic results for the Trifecta aortic pericardial valve. J Thorac Cardiovasc Surg. Mar. 2017,153(3):561-569.e2.

Goldstein JA, et al. Calcium channel blockers as drug repurposing candidates for gestational diabetes: Mining large scale genomic and electronic health records data to repurpose medications. Pharmacol Res. Apr. 2018;130:44-51.

Goldstein JA, et al. PregOMICS—Leveraging systems biology and bioinformatics for drug repurposing in maternal-child health. Am J Reprod Immunol. May 4, 2018;e12971.

Gormley SM, et al. Plasma and urinary cytokine homeostasis and renal dysfunction during cardiac surgery. Anesthesiology. Nov. 2000;93(5):1210-1216.

Grams ME, et al. Explaining the Racial Difference in AKI Incidence. JASN. American Society of Nephrology; Aug. 1, 2014;25(8):1834-1841.

Guelin, et al. Montelukast therapy and psychological distress in chronic obstructive pulmonary disease (COPD): a preliminary report. Arch Gerontol Geriatr. Feb. 2011;52(1):e36-39.

Gulbins E, et al. Cysteinyl leukotriene actions on the microcirculation of the normal and split hydronephrotic rat kidney. Eur J Clin Invest. Apr. 1991;21(2):184-196.

Harris PA, et al. Research electronic data capture (REDCap)—a metadata-driven methodology and workflow process for providing translational research informatics support. J Biomed Inform. Apr. 2009;42(2):377-381.

(56) References Cited

OTHER PUBLICATIONS

Hashim AA, et al. Cysteinyl leukotrienes predominantly mediate cisplatin-induced acute renal damage in male rats. J Physiol Pharmacol. Oct. 2018;69(5) 779-787.
Hay DW. Pharmacology of leukotriene receptor antagonists. More than inhibitors of bronchoconstriction. Chest. Feb. 1997;111(2 Suppl):35S-45S.
Heagerty, P. J., et al. "Time-dependent ROC curves for censored survival data and a diagnostic marker." Biometrics 56.2 (2000): 337-344.
Hebbring SJ, et al. A PheWAS approach in studying HLA-DRB1*1501. Genes Immun. Apr. 2013;14(3):187-191.
Helmy MM, et al. Montelukast abrogates rhabdomyolysis-induced acute renal failure via rectifying detrimental changes in antioxidant profile and systemic cytokines and apoptotic factors production. Eur J Pharmacol. May 15, 2012;683(1):294-300.
Helmy MW, et al. Enhanced lipoxygenase/LTD4 signaling accounts for the exaggerated hypertensive and nephrotoxic effects of cyclosporine plus indomethacin in rats. Biomed Pharmacother Biomedecine Pharmacother. Jun. 2018;102:309-316.
Himmelfarb J, et al. Perioperative THR-184 and AKI after Cardiac Surgery. J Am Soc Nephrol. 2018;29(2):670-679.
Hoffman BC, et al. Urinary Leukotriene E4 as a Biomarker of Exposure, Susceptibility, and Risk in Asthma: An Update. Immunol Allergy Clin North Am. 2018;38(4):599-610.
Holgate ST, et al. Roles of cysteinyl leukotrienes in airway inflammation, smooth muscle function, and remodeling. J Allergy Clin Immunol. Jan. 2003;111(1 Suppl):S18-34; discussion S34-36.
Hormati A, et al. Radioprotective effects of montelukast, a selective leukotriene CysLT1 receptor antagonist, against nephrotoxicity induced by gamma radiation in mice. J Biochem Mol Toxicol. Jun. 2020;34(6):e22479.
Huang GD, et al. Clinical trials recruitment planning: A proposed framework from the Clinical Trials Transformation Initiative. Contemporary Clinical Trials. Mar. 1, 2018;66:74-79.
Huber M, et al. Metabolism of cysteinyl leukotrienes in monkey and man. Eur J Biochem. Nov. 26, 1990;194(1):309-315.
Ikeda G, et al. Effect of a cysteinyl leukotriene receptor antagonist on experimental emphysema and asthma combined with emphysema. Am J Respir Cell Mol Biol. Jan. 2014;50(1):18-29.
Imamura T, et al. Association of Inflow Cannula Position with Left Ventricular Unloading and Clinical Outcomes in Patients with HeartMate II Left Ventricular Assist Device. Asaio J. Jun. 2019;65(4):331-335.
Imamura T, et al. Improvement in Biventricular Cardiac Function After Ambulatory Counterpulsation. J Card Fail. Jan. 2019;25(1):20-26.
Imig JD, et al. Immune and Inflammatory Role in Renal Disease. Compr Physiol. Apr. 2013;3(2):957-976.
International Preliminary Report on Patentability for Application No. PCT/US2021/040204 dated Dec. 13, 2022 (5 pages).
International Search Report and Written Opinion for Application No. PCT/US2021/040204 dated Oct. 19, 2021 (12 pages).
Jerome RN, et al. Using Human "Experiments of Nature" to Predict Drug Safety Issues: An Example with PCSK9 Inhibitors. Drug Saf. 2018;41(3):303-311.
Johnson DA, et al. Case Study: Community Engagement and Clinical Trial Success: Outreach to African American Women: Recruitment of African American Women in Clinical Trial. Clinical and Translational Science. Aug. 2015;8(4):388-390.
Joosten YA, Israel TL, Williams NA, Boone LR, Schlundt DG, Mouton CP, Dittus RS, Bernard GR, Wilkins CH. Community Engagement Studios: A Structured Approach to Obtaining Meaningful Input From Stakeholders to Inform Research. Academic Medicine. Dec. 2015;90(12):1646-1650.
KDIGO Clinical Practice Guideline for Acute Kidney Injury. Kidney International Supplements [Internet]. Mar. 2012;2(1). Available from: https://kdigo.org/wp-content/uploads/2016/10/KDIGO-2012-AKI-Guideline-English.pdf (141 pages).

Kerr PM, et al. Endothelial feedback and the myoendothelial projection. Microcirculation. Jul. 2012;19(5):416-422.
Khan BA, et al. The Confusion Assessment Method for the ICU-7 Delirium Severity Scale: A Novel Delirium Severity Instrument for Use in the ICU. Critical Care Medicine. May 2017;45(5):851-857.
Khera T, et al. Ultrasound-Guided Pecto-Intercostal Fascial Block for Postoperative Pain Management in Cardiac Surgery: A Prospective, Randomized, Placebo-Controlled Trial. J Cardiothorac Vasc Anesth. Jul. 24, 2020.
Khodir AE, et al. Montelukast reduces sepsis-induced lung and renal injury in rats. Can J Physiol Pharmacol. Oct. 2014;92(10):839-847.
Khwaja, A. "Kdigo clinical practice guidelines for acute kidney injury." Nephron Clinical Practice 120.4 (2012): c179-c184.
Klausner JM, et al. Postischemic renal injury is mediated by neutrophils and leukotrienes. Am J Physiol. May 1989;256(5 Pt 2):F794-802.
Koch CG, et al. A Randomized Clinical Trial of Red Blood Cell Transfusion Triggers in Cardiac Surgery. Ann Thorac Surg. Oct. 2017;104(4):1243-1250.
Kose E, et al. The effects of montelukast against amikacin-induced acute renal damage. Eur Rev Med Pharmacol Sci. Apr. 2012;16(4):503-511.
Kumar P, et al. Predicting the effects of coding non-synonymous variants on protein function using the SIFT algorithm. Nat Protoc. 2009;4(7):1073-1081.
Laitinen LA, et al. Leukotriene E4 and granulocytic infiltration into asthmatic airways. Lancet Lond Engl. Apr. 17, 1993;341(8851):989-990.
Lapar DJ, et al. Multicenter evaluation of high-risk mitral valve operations: implications for novel transcatheter valve therapies. Ann Thorac Surg. Dec. 2014;98(6):2032-2038.
Leaf DE, et al. End Points for Clinical Trials in Acute Kidney Injury. Am J Kidney Dis. Jan. 2017;69(1):108-116.
Lee W, et al. Leukotrienes induce the migration of Th17 cells. Immunol Cell Biol. Jun. 2015;93(5):472-479.
Lek M, et al. Analysis of protein-coding genetic variation in 60,706 humans. Nature. 2016 18;536(7616):285-291.
Lindroth H, et al. Delirium Severity Trajectories and Outcomes in ICU Patients. Defining a Dynamic Symptom Phenotype. Ann Am Thorac Soc. 2020;17(9):1094-1103.
Liu L, et al. Leukotriene receptor antagonists do not improve lung function decline in COPD: a meta-analysis. Eur Rev Med Pharmacol Sci. Feb. 2018;22(3):829-834.
Loef BG, Epema AH, Smilde TD, Henning RH, Ebels T, Navis G, Stegeman CA. Immediate postoperative renal function deterioration in cardiac surgical patients predicts in-hospital mortality and long-term survival. J Am Soc Nephrol. Jan. 2005;16(1):195-200.
Lopez MG, et al. The Risk of Oxygen during Cardiac Surgery (ROCS) trial: study protocol for a randomized clinical trial. Trials. 2017 26;18(1):295.
Lynch KR, et al. Characterization of the human cysteinyl leukotriene CysLTI receptor I Nature. Nature. Jun. 24, 1999;399(6738):789-93.
Mack MJ, et al. Effect of Cerebral Embolic Protection Devices on CNS Infarction in Surgical Aortic Valve Replacement: A Randomized Clinical Trial. JAMA. Aug. 8, 2017;318(6):536-547.
Maeba S, et al. Effect of montelukast on nuclear factor kappaB activation and proinflammatory molecules. Ann Allergy Asthma Immunol. Jun. 2005;94(6):670-674.
Maekawa A, et al. GPR17 regulates immune pulmonary inflammation induced by house dust mites. J Immunol Baltim Md 1950. Aug. 1, 2010;185(3):1846-1854.
Malek, M. et al. "Renal ischemia/reperfusion injury; from pathophysiology to treatment." Journal of renal injury prevention 4.2 (2015): 20-27.
Mamoun NF, et al. Intravenous acetaminophen analgesia after cardiac surgery: A randomized, blinded, controlled superiority trial. J Thorac Cardiovasc Surg. Sep. 2016;152(3):881-889.el.
Mao, H., et al. "Cardiac surgery-associated acute kidney injury." Cardiorenal medicine 3.3 (2013): 178-199.
Marrazzo F, et al. Protocol of a randomised controlled trial in cardiac surgical patients with endothelial dysfunction aimed to

(56) References Cited

OTHER PUBLICATIONS prevent postoperative acute kidney injury by administering nitric oxide gas. BMJ Open. Jul. 4, 2019;9(7):e026848.

Mauermann WJ, et al. Amiodarone versus lidocaine and placebo for the prevention of ventricular fibrillation after aortic crossclamping: a randomized, double-blind, placebo-controlled trial. J Thorac Cardiovasc Surg. Nov. 2012;144(5):1229-1234.

McBride WT, et al. Cytokine phenotype, genotype, and renal outcomes at cardiac surgery. Cytokine. Jan. 2013;61(1):275-284.

McGovern T, et al. CysLTI Receptor Is Protective against Oxidative Stress in a Model of Irritant-Induced Asthma. J Immunol Baltim Md 1950. 2016 01;197(1):266-277.

McIlroy DR, et al. Perioperative Clinical Trials in AKI. Semin Nephrol. 2020;40(2):173-187.

McIlroy DR, et al. Systematic review and consensus definitions for the Standardised Endpoints in Perioperative Medicine (StEP) initiative: renal endpoints. Br J Anaesth. Nov. 2018;121(5):1013-1024.

Medzhitovr. Origin and physiological roles of inflammation. Nature. Nature Publishing Group; Jul. 2008;454(7203):428-435.

Mehra MR, et al. A Fully Magnetically Levitated Left Ventricular Assist Device—Final Report. N Engl J Med. Apr. 25, 2019;380(17):1618-1627.

Mehta RH, et al. Levosimendan in Patients with Left Ventricular Dysfunction Undergoing Cardiac Surgery. N Engl J Med. May 25, 2017;376(21):2032-2042.

Mehta, S., et al. "The prognostic importance of duration of AKI: a systematic review and meta-analysis." BMC nephrology 19.1 (2018): 1-10.

Mohebati A, et al. Effect of Zileuton and Celecoxib on Urinary LTE4 and PGE-M Levels in Smokers. Cancer Prevention Research. Jul. 1, 2013;6(7):646-655.

Moledina DG, et al. Association of T Cell-Derived Inflammatory Cytokines With Acute Kidney Injury and Mortality After Cardiac Surgery. Kidney International Reports. Dec. 1, 2019;4(12):1689-1697.

Moledina DG, et al. Plasma Monocyte Chemotactic Protein-1 Is Associated With Acute Kidney Injury and Death After Cardiac Operations. Ann Thorac Surg. Aug. 2017;104(2):613-620.

Montuschip, et al. Liquid chromatography-mass spectrometry measurement of leukotrienes in asthma and other respiratory diseases. J Chromatogr B Analyt Technol Biomed Life Sci. Aug. 1, 2014;964:12-25.

Moore KP, et al. Increased production of cysteinyl leukotrienes in hepatorenal syndrome. J Hepatol. Sep. 1990;11(2):263-271.

Mori M, et al. Eosinophil superoxide anion generation induced by adhesion molecules and leukotriene D4. Int Arch Allergy Immunol. 2009;149 Suppl 1:31-38.

Mozaffarian D, et al. Fish Oil and Postoperative Atrial Fibrillation: The Omega-3 Fatty Acids for Prevention of Post-operative Atrial Fibrillation (OPERA) Randomized Trial. JAMA. Nov. 21, 2012;308(19):2001-2011.

Mullard A. Low-cost non-profit drug repurposing. Nat Rev Drug Discov. Dec. 28, 2018;18(1):7.

Nasreddine ZS, et al. The Montreal Cognitive Assessment, MoCA: A Brief Screening Tool for Mild Cognitive Impairment. Journal of the American Geriatrics Society. 2005;53(4):695-699.

National Institutes of Health. NIH Genomic Data Sharing Policy [Internet]. National Institutes of Health: Grants. 2014. Available from: http://grants.nih.gov/grants/guide/notice-files/NOT-OD-14-124.html (17 pages).

Nelson MR, et al. The support of human genetic evidence for approved drug indications. Nat Genet. Aug. 2015;47(8):856-860.

Newman MF, et al. Effect of adenosine-regulating agent acadesine on morbidity and mortality associated with coronary artery bypass grafting: the RED-CABG randomized controlled trial. JAMA. Jul. 11, 2012;308(2):157-164.

O'Donoghue M., et al. Lipoprotein-Associated Phospholipase A2 and Its Association With Cardiovascular Outcomes in Patients With Acute Coronary Syndromes in the Prove IT-TIMI 22 (PRavastatin or ator Vastatin Evaluation and Infection Therapy—Thrombolysis in Myocardial Infarction) Trial. Circulation. American Heart Association; Apr. 11, 2006;113(14):1745-1752.

O'Gara BP, et al. Prevention of Early Postoperative Decline: A Randomized, Controlled Feasibility Trial of Perioperative Cognitive Training. Anesth Analg. Mar. 2020;130(3):586-595.

O'Kane D, et al. Preconditioning against renal ischaemia reperfusion injury: the failure to translate to the clinic. J Nephrol. Jan. 11, 2019.

O'Neal JB, et al. Acute kidney injury following cardiac surgery: current understanding and future directions. Critical Care. Jul. 4, 2016;20(1):187.

O'Neal JB, et al. Effect of Preoperative Beta-Blocker Use on Outcomes Following Cardiac Surgery. Am J Cardiol. Oct. 15, 2017;120(8):1293-1297.

Oetjens MT, et al. Assessment of a pharmacogenomic marker panel in a polypharmacy population identified from electronic medical records. Pharmacogenomics. May 2013;14(7):735-744.

Okusa MD, et al. Design of clinical trials in acute kidney injury: a report from an NIDDK workshop—prevention trials. Clin J Am Soc Nephrol. May 2012;7(5):851-855.

Oliver WC, et al. A prospective, randomized, double-blind trial of 3 regimens for sedation and analgesia after cardiac surgery. J Cardiothorac Vasc Anesth. Feb. 2011;25(1):110-119.

Oprea TI, et al. Computational and Practical Aspects of Drug Repositioning. Assay Drug Dev Technol. Jul. 1, 2015;13(6):299-306.

Oshima Y, et al. Corticosteroid reduction by addition of cetirizine and montelukast in biopsy-proven minimal-change nephrotic syndrome concomitant with allergic disorders. Sci Rep. Jan. 30, 2020;10(1):1490.

Otunctemur A, et al. Beneficial effects montelukast, cysteinyl-leukotriene receptor antagonist, on renal damage after unilateral ureteral obstruction in rats. Int Braz J Urol Off J Braz Soc Urol. Apr. 2015;41(2):279-287.

Otunctemur A, et al. Protective effect of montelukast which is cysteinyl-leukotriene receptor antagonist on gentamicin-induced nephrotoxicity and oxidative damage in rat kidney. Ren Fail. 2013;35(3):403-410.

Palevsky PM, et al. Design of clinical trials in acute kidney injury: report from an NIDDK workshop on trial methodology. Clin J Am Soc Nephrol. May 2012;7(5):844-850.

Palevsky, PM. "Endpoints for clinical trials of acute kidney injury." Nephron 140.2 (2018): 111-115.

Pan H, et al. SEARS: A Seamless Dose Escalation/Expansion with Adaptive Randomization Scheme. Clin Trials. Feb. 2014;11(1):49-59.

Pandharipande PP, et al. Long-Term Cognitive Impairment after Critical Illness. New England Journal of Medicine. Massachusetts Medical Society; Oct. 3, 2013;369(14):1306-1316.

Pannu N, et al. Association between AKI, Recovery of Renal Function, and Long-Term Outcomes after Hospital Discharge. Clin J Am Soc Nephrol. Feb. 7, 2013;8(2):194-202.

Parker AR, et al. Lipid Mediators in Aspirin-Exacerbated Respiratory Disease. Immunol Allergy Clin North Am. Nov. 2016;36(4):749-763.

Pelclová D, et al. 8-isoprostane and leukotrienes in exhaled breath condensate in Czech subjects with silicosis. Ind Health. Dec. 2007;45(6):766-774.

Peters-Golden M, et al. Cysteinyl leukotrienes: multi-functional mediators in allergic rhinitis. Clin Exp Allergy J Br Soc Allergy Clin Immunol. Jun. 2006;36(6):689-703.

Peters-Golden M, et al. Leukotrienes. N Engl J Med. Nov. 1, 2007;357(18):1841-1854.

Philip G, et al. Analysis of behavior-related adverse experiences in clinical trials of montelukast. J Allergy Clin Immunol. Oct. 2009;124(4):699-706.e8.

Philip G, et al. Reports of suicidality in clinical trials of montelukast. J Allergy Clin Immunol. Oct. 2009;124(4):691-696.e6.

Picado C. Mechanisms of aspirin sensitivity. Curr Allergy Asthma Rep. May 2006;6(3):198-202.

Popma JJ, et al. Transcatheter Aortic-Valve Replacement with a Self-Expanding Valve in Low-Risk Patients. N Engl J Med. May 2, 2019;380(18):1706-1715.

(56) References Cited

OTHER PUBLICATIONS

Poulin S, et al. Cysteinyl-leukotrienes induce vascular endothelial growth factor production in human monocytes and bronchial smooth muscle cells. Clin Exp Allergy J Br Soc Allergy Clin Immunol. Feb. 2011;41(2):204-217.
Pretorius M, et al. Angiotensin-converting enzyme inhibition or mineralocorticoid receptor blockade do not affect prevalence of atrial fibrillation in patients undergoing cardiac surgery. Crit Care Med. Oct. 2012;40(10):2805-2812.
Profita M, et al. Cysteinyl leukotriene-1 receptor activation in a human bronchial epithelial cell line leads to signal transducer and activator of transcription 1-mediated eosinophil adhesion. J Pharmacol Exp Ther. Jun. 2008;325(3):1024-1030.
Pulley J, et al. Principles of human subjects protections applied in an opt-out, de-identified biobank. Clin Transl Sci. Feb. 2010;3(1):42-48.
Pulley JM, et al. Accelerating Precision Drug Development and Drug Repurposing by Leveraging Human Genetics. ASSAY and Drug Development Technologies. Apr. 2017;15(3):113-119.
Pulley JM, et al. Advocating for mutually beneficial access to shelved compounds. Future Med Chem. Jun. 1, 2018;10(12):1395-1398.
Pulley JM, et al. Attitudes and perceptions of patients towards methods of establishing a DNA biobank. Cell Tissue Bank. Mar. 2008;9(1):55-65.
Pulley JM, et al. Motivation for Launching a Cancer Metastasis Inhibition (CMI) Program. Targeted Oncology. Feb. 2018;13(1):61-68.
Pulley JM, et al. Using What We Already Have: Uncovering New Drug Repurposing Strategies in Existing Omics Data. Annual Review of Pharmacology and Toxicology. 2020;60(1):333-352.
Pulley JM, et al. When Enough Is Enough: Decision Criteria for Moving a Known Drug into Clinical Testing for a New Indication in the Absence of Preclinical Efficacy Data. ASSAY and Drug Development Technologies. Dec. 2017;15(8):354-361.
Rabb H, et al. Inflammation in AKI: Current Understanding, Key Questions, and Knowledge Gaps. J Am Soc Nephrol. Feb. 2016;27(2):371-379.
Rafnsson A, et al. Urinary Leukotriene E4 Is Associated with Renal Function but Not with Endothelial Function in Type 2 Diabetes. Dis Markers. 2013;35(5):475-480.
Ramirez AH, et al. Predicting warfarin dosage in European-Americans and African-Americans using DNA samples linked to an electronic health record. Pharmacogenomics. Mar. 2012, 13(4):407-418.
Rangrass G, et al. Explaining racial disparities in outcomes after cardiac surgery: the role of hospital quality. JAMA Surg. Mar. 2014;149(3):223-227.
Rankin GO, et al. Role of leukotrienes in N-(3,5-dichlorophenyl)succinimide (NDPS) and NDPS metabolite nephrotoxicity in male Fischer 344 rats. Toxicology. Oct. 9, 2012;300(1-2):92-99.
Reinhold SW, et al. Lipoxygenase products in the urine correlate with renal function and body temperature but not with acute transplant rejection. Lipids. Feb. 2013;48(2):167-175.
Reiss TF, et al. Effects of montelukast (MK-0476), a new potent cysteinyl leukotriene (LTD4) receptor antagonist, in patients with chronic asthma. J Allergy Clin Immunol. Sep. 1996;98(3):528-534.
Reiss TF, et al. Effects of montelukast (MK-0476); a potent cysteinyl leukotriene receptor antagonist, on bronchodilation in asthmatic subjects treated with and without inhaled corticosteroids. Thorax. Jan. 1997;52(1):45-48.
Ritchie MD, et al. Genome- and phenome-wide analyses of cardiac conduction identifies markers of arrhythmia risk. Circulation. Apr. 2, 2013;127(13):1377-1385.
Ritchie MD, et al. Robust replication of genotype-phenotype associations across multiple diseases in an electronic medical record. American journal of human genetics. Apr. 2010;86(4):560-572.
Robinson DR. Eicosanoids, inflammation, and anti-inflammatory drugs. Clin Exp Rheumatol. Oct. 1989;7 Suppl 3:S155-161.

Roden DM, et al. Development of a Large-Scale De-Identified DNA Biobank to Enable Personalized Medicine. Clinical Pharmacology & Therapeutics. May 21, 2008;84(3):362-369.
Roozenbeek B, et al. The added value of ordinal analysis in clinical trials: an example in traumatic brain injury. Crit Care. 2011;15(3):R127.
Rosamond W, et al. Heart disease and stroke statistics—2007 update: a report from the American Heart Association Statistics Committee and Stroke Statistics Subcommittee. Circulation. Feb. 6, 2007;115(5):e69-171.
Rosner MH, et al. Acute kidney injury associated with cardiac surgery. Clin J Am Soc Nephrol. Jan. 2006;1(1):19-32.
Rubinstein I, et al. Long-term montelukast therapy in moderate to severe COPD—a preliminary observation. Respir Med. Feb. 2004;98(2):134-138.
Rubinstein M, et al. Leukotrienes and kidney diseases. Curr Opin Nephrol Hypertens. Jan. 2018;27(1):42-48.
Ryckwaert F, et al. Incidence, risk factors, and prognosis of a moderate increase in plasma creatinine early after cardiac surgery. Crit Care Med. Jul. 2002;30(7):1495-1498.
Saager L, et al. Intraoperative tight glucose control using hyperinsulinemic normoglycemia increases delirium after cardiac surgery. Anesthesiology. Jun. 2015;122(6):1214-1223.
Saari, W. S., et al. "Synthesis and antihypertensive activity of some ester progenitors of methyldopa." Journal of Medicinal Chemistry 21.8 (1978):746-753.
Sahib, H. A., et al. "Protective effect of montelukast against acute kidney injury in rats induced by diclofenac." Journal of Pharmaceutical Sciences and Research 10.9 (2018): 2415-2418.
Sakamoto, F. et al. "Studies on prodrugs. II. Preparation and characterization of (5-substituted 2-oxo-1, 3-dioxolen-4-yl) methyl esters of ampicillin." Chemical and pharmaceutical bulletin 32.6 (1984): 2241-2248.
Sarau HM, et al. Identification, molecular cloning, expression, and characterization of a cysteinyl leukotriene receptor. Mol Pharmacol. Sep. 1999;56(3):657-663.
Savari S. Cysteinyl leukotrienes and their receptors: Bridging inflammation and colorectal cancer. World J Gastroenterol. 2014;20(4):968-977.
Schoors DF, et al. Single dose pharmacokinetics, safety and tolerability of MK-0476, a new leukotriene D4-receptor antagonist, in healthy volunteers. Br J Clin Pharmacol. Sep. 1995;40(3):277-280.
Sellke FW. Vascular changes after cardiopulmonary bypass and ischemic cardiac arrest: roles of nitric oxide synthase and cyclooxygenase. Brazilian Journal of Medical and Biological Research. Nov. 1999;32(11):1345-1352.
Sener G, et al. Chronic renal failure-induced multiple-organ injury in rats is alleviated by the selective CysLT1 receptor antagonist montelukast. Prostaglandins Other Lipid Mediat. Jun. 2007;83(4):257-267.
Sener G, et al. Gastroprotective effect of leukotriene receptor blocker montelukast in alendronat-induced lesions of the rat gastric mucosa. Prostaglandins Leukot Essent Fatty Acids. Jan. 2005;72(1):1-11.
Sener G, et al. Montelukast protects against renal ischemia/reperfusion injury in rats. Pharmacol Res. Jul. 1, 2006;54(1):65-71.
Sessler CN, et al. The Richmond Agitation-Sedation Scale. Am J Respir Crit Care Med. American Thoracic Society—AJRCCM; Nov. 15, 2002;166(10):1338-1344.
Shaefi S, et al. Intraoperative Oxygen Concentration and Neurocognition after Cardiac Surgery. Anesthesiology. Feb. 1, 2021;134(2):189-201.
Sharp CN, et al. Developing better mouse models to study cisplatin-induced kidney injury. Am J Physiol—Ren Physiol. Jul. 19, 2017;313(4):F835-F841.
Shelton KT, et al. Minimizing ICU Neurological Dysfunction with Dexmedetomidine-induced Sleep (MINDDS): protocol for a randomised, double-blind, parallel-arm, placebo-controlled trial. BMJ Open. Apr. 20, 2018;8(4):e020316.
Shi SM, et al. Delirium Incidence and Functional Outcomes After Transcatheter and Surgical Aortic Valve Replacement. J Am Geriatr Soc. Jul. 2019;67(7):1393-1401.

(56) References Cited

OTHER PUBLICATIONS

Sim N-L, et al. SIFT web server: predicting effects of amino acid substitutions on proteins. Nucleic Acids Res. Jul. 2012;40(Web Server issue):W452-457.

Singh A, et al. On-pump versus off-pump coronary artery bypass graft surgery among patients with type 2 diabetes in the Bypass Angioplasty Revascularization Investigation 2 Diabetes trial. Eur J Cardiothorac Surg. Feb. 2016;49(2):406-416.

Singulair (Montelukast Sodium) Package Insert. [Internet]. 2009. FDA; Available from: https://www.accessdata.fda.gov/drugsatfda_docs/label/2009/020829s051_020830s052_021409s0281bl.pdf (25 pages).

Skrypnyk NI, et al. Bridging translation for acute kidney injury with better preclinical modeling of human disease. Am J Physiol Renal Physiol. May 15, 2016;310(10):F972-F984.

Sparrow HG, et al. Disparate outcomes observed within Kidney Disease: Improving Global Outcomes (KDIGO) acute kidney injury stage 1. Kidney Int. 2019;95(4):905-913.

Spector SL, et al. Safety of antileukotriene agents in asthma management. Ann Allergy Asthma Immunol. Jun. 2001;86(6 Suppl 1):18-23.

Stählibe, et al. Effects of P-Selectin Antagonist Inclacumab in Patients Undergoing Coronary Artery Bypass Graft Surgery: SELECT-CABG Trial. J Am Coll Cardiol. Jan. 26, 2016;67(3):344-346.

Subramaniam B, et al. Effect of Intravenous Acetaminophen vs Placebo Combined With Propofol or Dexmedetomidine on Postoperative Delirium Among Older Patients Following Cardiac Surgery: The DEXACET Randomized Clinical Trial. JAMA. Feb. 19, 2019;321(7):686-696.

Suddek GM. Montelukast ameliorates kidney function and urinary bladder sensitivity in experimentally induced renal dysfunction in rats. Fundam Clin Pharmacol. Apr. 2013;27(2):186-191.

Sunay M, et al. Do Montelukast Sodium and N-Acetylcysteine Have a Nephroprotective Effect on Unilateral Ureteral Obstruction? A Placebo Controlled Trial in a Rat Model. J Urol. Oct. 2015;194(4):1132-1137.

Suri RM, et al. A prospective, randomized comparison of 3 contemporary bioprosthetic aortic valves: should hemodynamic performance influence device selection? J Thorac Cardiovasc Surg. Dec. 2012;144(6):1387-1398.

Suri RM, et al. Prospective US investigational device exemption trial of a sutureless aortic bioprosthesis: One-year outcomes. J Thorac Cardiovasc Surg. May 2019;157(5):1773-1782.e3.

Suzuki H, et al. Murine Models of Human IgA Nephropathy. Semin Nephrol. 2018;38(5):513-520.

Szeto WY, et al. Appropriate patient selection or health care rationing? Lessons from surgical aortic valve replacement in the Placement of Aortic Transcatheter Valves I trial. J Thorac Cardiovasc Surg. Sep. 2015;150(3):557-568.e11.

Tahan F, et al. Montelukast inhibits tumour necrosis factor-alpha-mediated interleukin-8 expression through inhibition of nuclear factor-kappaB p65-associated histone acetyltransferase activity. Clin Exp Allergy. May 2008;38(5):805-811.

Tamada T, et al. Leukotriene Receptor Antagonists and Antiallergy Drugs. Handb Exp Pharmacol. 2017;237:153-169.

Teachey DT, et al. Treatment with sirolimus results in complete responses in patients with autoimmune lymphoproliferative syndrome. Br J Haematol. Apr. 2009;145(1):101-106.

Teslariu O, et al. Influence of montelukast on cisplatin-induced experimental acute renal failure. Rev Med Chir Soc Med Nat Iasi. Sep. 2014;118(3):612-617.

Thakar CV, et al. Renal dysfunction and serious infections after open-heart surgery. Kidney Int. Jul. 2003;64(1):239-246.

Thompson MD, et al. Cysteinyl Leukotrienes Pathway Genes, Atopic Asthma and Drug Response: From Population Isolates to Large Genome-Wide Association Studies. Front Pharmacol [Internet]. Dec. 1, 2016;7, 1-17.

Tintinger GR, et al. Montelukast: more than a cysteinyl leukotriene receptor antagonist? Scientific WorldJournal. Dec. 14, 2010;10:2403-2413.

Truong TM, et al. The ImPreSS Trial: Implementation of Point-of-Care Pharmacogenomic Decision Support in Perioperative Care. Clin Pharmacol Ther. Dec. 2019;106(6):1179-1183.

Tsuji, E., et al. "Preparation of 3-acetoacetylaminobenzo [b] furan derivatives with cysteinyl leukotriene receptor 2 antagonistic activity." Organic & biomolecular chemistry 1.18 (2003): 3139-3141.

Tuğtepe H, et al. Oxidative renal damage in pyelonephritic rats is ameliorated by montelukast, a selective leukotriene CysLTl receptor antagonist. Eur J Pharmacol. Feb. 14, 2007;557(1):69-75.

Turan A, et al. Dexmedetomidine for reduction of atrial fibrillation and delirium after cardiac surgery (DECADE): a randomised placebo-controlled trial. The Lancet. Elsevier; Jul. 18, 2020;396(10245):177-185.

Turan A, et al. Methylprednisolone Does Not Reduce Persistent Pain after Cardiac Surgery. Anesthesiology. Dec. 2015;123(6):1404-1410.

Uriel N, et al. Clinical Outcomes and Quality of Life With an Ambulatory Counterpulsation Pump in Advanced Heart Failure Patients: Results of the Multicenter Feasibility Trial. Circ Heart Fail. Apr. 2020,13(4):e006666.

Usmani M, et al. Development and Evaluation of Orally Disintegrating Tablets of Montelukast Sodium by Direct Compression Method. Trop J Pharm Res. Feb. 4, 2015;14(1):1-6.

Van Driest SL, et al. Acute kidney injury risk-based screening in pediatric inpatients: a pragmatic randomized trial. Pediatr Res. Aug. 27, 2019; 118-124.

Van Hecken A, et al. Effect of montelukast on the pharmacokinetics and pharmacodynamics of warfarin in healthy volunteers. J Clin Pharmacol. May 1999;39(5):495-500.

Vane JR. Inhibition of Prostaglandin Synthesis as a Mechanism of Action for Aspirin-like Drugs. Nature New Biology. Nature Publishing Group; Jun. 1971;231(25):232-235.

Vermeulen Windsant IC et al. Cardiovascular surgery and organ damage: Time to reconsider the role of hemolysis. The Journal of Thoracic and Cardiovascular Surgery. Jul. 1, 2011;142(1):1-11.

Villa G, et al. Extracorporeal Membrane Oxygenation and the Kidney. Cardiorenal Med. Dec. 2015;6(1):50-60.

Vincent J-L, et al. Circulatory Shock. New England Journal of Medicine. Massachusetts Medical Society; Oct. 31, 2013;369(18):1726-1734.

Walsh M, et al. Effects of remote ischemic preconditioning in high-risk patients undergoing cardiac surgery (Remote IMPACT): a randomized controlled trial. CMAJ. Mar. 15, 2016;188(5):329-336.

Wang T, et al. Arachidonic Acid Metabolism and Kidney Inflammation. IJMS. Jul. 27, 2019;20(15):3683.

Wang V, et al. The Economic Burden of Chronic Kidney Disease and End-Stage Renal Disease. Semin Nephrol. 2016;36(4):319-330.

Wang Y, et al. Cardiac surgery-associated acute kidney injury: risk factors, pathophysiology and treatment. Nat Rev Nephrol. Nov. 2017;13(11):697-711.

Watnick, S., et al. "Kidney disease." CURRENT Medical Diagnosis and Treatment 47 (2008): 794-826.

Wei R, et al. Vasoconstrictor stimulus determines the functional contribution of myoendothelial feedback to mesenteric arterial tone. J Physiol (Lond). 2018 01;596(7):1181-1197.

Wilkins CH, et al. Understanding What Information Is Valued by Research Participants, and Why. Health Affairs. Mar. 2019;38(3):399-407.

Woszczek G, et al. Functional Characterization of Human Cysteinyl Leukotriene 1 Receptor Gene Structure. J Immunol. Oct. 15, 2005;175(8):5152-5159.

Wrobel K, et al. Influence of Baseline Characteristics, Operative Conduct, and Postoperative Course on 30-Day Outcomes of Coronary Artery Bypass Grafting Among Patients With Left Ventricular Dysfunction: Results From the Surgical Treatment for Ischemic Heart Failure (STICH) Trial. Circulation. Aug. 25, 2015;132(8):720-730.

Wu C, et al. BioGPS and MyGene.info: organizing online, gene-centric information. Nucleic Acids Res. Jan. 2013;41(Database issue):D561-565.

Wu S-H, et al. Add-on therapy with montelukast in the treatment of Henoch-Schönlein purpura. Pediatr Int. Jun. 2014;56(3):315-322.

(56) References Cited

OTHER PUBLICATIONS

Wu, S., et al. "The protective role of montelukast against intestinal ischemia-reperfusion injury in rats." Scientific reports 5.1 (2015): 15787.

Yan F, et al. Phase I-II clinical trial design: a state-of-the-art paradigm for dose finding. Annals of Oncology. Elsevier; Mar. 1, 2018;29(3):694-699.

Yang G, et al. Transgenic smooth muscle expression of the human CysLTI receptor induces enhanced responsiveness of murine airways to leukotriene D4. Am J Physiol Lung Cell Mol Physiol. May 2004;286(5):L992-L1001.

Yeung CK, et al. Coenzyme Q10 dose-escalation study in hemodialysis patients: safety, tolerability, and effect on oxidative stress. BMC Nephrol. Nov. 3, 2015;16:183.

Zedan MM, et al. Montelukast as an add-on treatment in steroid dependant nephrotic syndrome, randomised-controlled trial. J Nephrol. Aug. 2016;29(4):585-92.

Zhang WR, et al. Plasma IL-6 and IL-10 Concentrations Predict AKI and Long-Term Mortality in Adults after Cardiac Surgery. J Am Soc Nephrol. Dec. 2015;26(12):3123-3132.

Zhao JJ, et al. Pharmacokinetics and bioavailability of montelukast sodium (MK-0476) in healthy young and elderly volunteers. Biopharm Drug Dispos. Dec. 1997;18(9):769-777.

ZYFLO Package Insert [Internet]. FDA. 2012. Available from: https://www.accessdata.fda.gov/drugsatfda_docs/label/2012/020471s017lbl.pdf 14 pages.

* cited by examiner

METHODS OF TREATMENT FOR A KIDNEY DISEASE

CROSS-REFERENCE TO RELATED APPLICATIONS

This patent application is the U.S. national stage entry, under 35 U.S.C. § 371 of International Application Number PCT/US2021/040204, filed Jul. 1, 2021 which claims priority to U.S. Provisional Application No. 63/047,217 filed on Jul. 1, 2020 and U.S. Provisional Application No. 63/048,623 filed Jul. 6, 2020, the entire contents of each of which are hereby incorporated by reference.

STATEMENT REGARDING FEDERALLY SPONSORED RESEARCH

This invention was made with government support under grant U34TR003298 awarded by the National Institutes of Health. The government has certain rights in the invention.

FIELD

This disclosure relates to methods of treatment for a cardiac surgery-associated acute kidney injury and extracorporeal membrane oxygenation-associated acute kidney injury.

The methods include administering to a subject a therapeutically effective amount of a leukotriene receptor antagonist compound.

INTRODUCTION

Acute kidney injury (AKI) is a devastating complication affecting a large portion of patients undergoing surgery, experiencing sepsis, or receiving care in an intensive care unit. The diagnosis of AKI is independently associated with a 5-fold increase in mortality. Even with apparent clinical recovery, AKI promotes renal function deterioration, ultimately progressing to chronic kidney disease (CKD) or end-stage renal disease (ESRD) in many patients. The prevalence of CKD and ESRD are increasing and pose substantial burdens on patients and society. In the past 30 years, no novel treatments for AKI or for the progression of CKD have been developed. Novel therapies, even if effective in a subset of renal disease patients, are greatly needed. Although AKI affects many types of patients, it occurs in 30% of cardiac surgery patients and is a major risk factor for death. Cardiac surgery provides an efficient setting to study the prevention of AKI with novel, safe therapies already in use where mechanisms are homogenous, timing of insults are known, and patients remain hospitalized.

There is an unmet medical need. Five hundred thousand people undergo cardiac surgery each year in the U.S. Despite advancements in surgical technique and perioperative patient management, postoperative organ injury remains a major problem. Thirty percent of patients suffer from AKI following cardiac surgery (25% at Vanderbilt), and these patients have a 5-fold increase in death at 30 days. Even with apparent clinical recovery, AKI promotes renal function deterioration, ultimately progressing to CKD or ESRD in many patients. Unfortunately, in the past 3 decades, no new treatments for the progression of CKD have been defined, thus limiting the therapeutic armamentarium to blood pressure control, glucose management in diabetics, and the use of renin-angiotensin system blockers. Novel therapies, even if effective in a subset of renal disease patients, are greatly needed.

In addition to significant morbidity and mortality, AKI and subsequent CKD or ESRD involve reduced quality of life and significant economic burdens on patients and their caregivers, e.g. considerable direct medical and nonmedical costs as well as productivity losses such as absenteeism, attending working while ill, disability, and early death.

While science has uncovered molecular mechanisms for approximately 5,700 human medical conditions, patients benefit from approved therapies for only about 500 of these conditions. Further, many approved therapies have suboptimal efficacy or unacceptable toxicity in many patient populations. Methods to improve drug/disease pairing for optimal efficacy and minimal toxicity represent an unmet medical need on a massive scale. In addition, new drugs created by the pharmaceutical industry in a given year address only 10-30 diseases and require massive investment. A recent review suggests that pursuing targets supported by human genetics could double the success rate in clinical development.

Therefore, there is a need for a novel, effective, and non-toxic treatment for AKI.

SUMMARY

In an aspect, the disclosure relates to a method of treating or reducing the severity of a cardiac surgery-associated acute kidney injury (CSA-AKI) in a subject in need thereof. The method may comprise administering to the subject a therapeutically effective amount of a compound of Formula I:

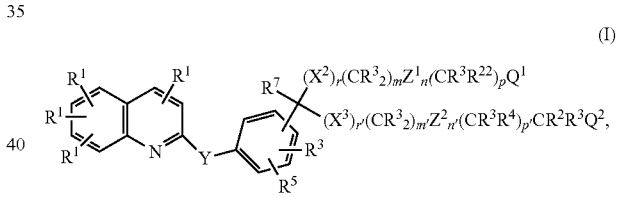

or a pharmaceutically acceptable ester or salt thereof, where: $R^1$ is H, halogen, —$CF_3$, —CN, —$NO_2$, or $N_3$; $R^2$ is lower alkyl, lower alkenyl, lower alkynyl, —$CF_3$, —$CH_2F$, —$CHF_2$, $CH_2CF_3$, substituted or unsubstituted phenyl, substituted or unsubstituted benzyl, substituted or unsubstituted 2-phenethyl, or two $R^2$ groups joined to the same carbon to form a carbocyclic ring of up to 8 members; $R^3$ is H or $R^2$; $R^4$ is halogen, —$NO_2$, —CN, —$OR^3$, —$SR^3$, $NR^3R^3$, $NR^3C(O)R^7$, or $R^3$; $R^5$ is H, halogen, —$NO_2$, —$N_3$, —CN, —$SR^2$, —$NR^3R^3$, —$OR^3$, lower alkyl, or —$C(O)R^3$; $R^6$ is —$(CH_2)_s$—$C(R^7R^7)$—$(CH_2)_s$—$R^8$ or —$CH_2C(O)NR^{12}R^{12}$; $R^7$ is H or $C_1$-$C_4$ alkyl; $R^8$ is the radical W—$R^9$; $R^9$ contains up to 20 carbon atoms and is (1) an alkyl group or (2) an alkylcarbonyl group of an organic acyclic or monocyclic carboxylic acid; $R^{11}$ is lower alkyl, —$C(O)R^{14}$, unsubstituted phenyl, or unsubstituted benzyl; $R^{12}$ is H or $R^{11}$; $R^{13}$ is lower alkyl, lower alkenyl, lower alkynyl, —$CF_3$ or substituted or unsubstituted phenyl, benzyl, or 2-phenethyl; $R^{1'}$ is H or $R^{13}$; $R^{16}$ is H, $C_1$-$C_4$ alkyl, or OH; $R^{17}$ is lower alkyl, lower alkenyl, lower alkynyl, or substituted or unsubstituted phenyl, benzyl, or 2-phenethyl; $R^{18}$ is lower alkyl, lower alkenyl, lower alkynyl, —CF3 or substituted or unsubstituted phenyl, benzyl, or 2-phenethyl; $R^{19}$ is lower alkyl, lower alkenyl, lower alkynyl, —$CF_3$ or substituted or unsubstituted phenyl, benzyl, or 2-phenethyl; $R^{21}$ is H or $R^{17}$; $R^{22}$ is $R^4$, $CHR^7 OR^3$, or $CHR^7SR^2$; m is 0-8; m' is 2 or 3; n and n' are independently 0 or 1, p and p' are independently 0-8; m+n+p is 1-10 when r is 1 and $X_2$ is O, S, S(O), or $S(O)_2$; m+n+p is 0-10 when r is 1 and $X_2$ is $CR^3R^{16}$; m+n+p is 0-10 when r is 0; m'+n'+p' is 2-10; r and r' are independently 0 or 1; s is 0-3; $Q^1$ is —C(O)OR$^3$, 1H (or 2H)-tetrazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O)NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH; $Q^2$ is OH; W is O, S, or NR$^3$; $X^2$ and $X^3$ are independently O, S, S(O), S(O)$_2$, or CR$^3$R$^{16}$; with the proviso that at least one is S or SO$_2$; Y is —CR$^3$=CR$^3$— $Z^1$ and $Z^2$ are independently -HET(R$^3$)(R$^5$)—; HET is the diradical of a benzene, a pyridine, a furan, or a thiophene; and, wherein the compound decreases urinary leukotrienes.

In a further aspect, the disclosure relates to a method of treating or reducing the severity of an extracorporeal membrane oxygenation-associated acute kidney injury (ECMO-AKI) in a subject in need thereof. The method may comprise administering to the subject a therapeutically effective amount of a compound of Formula I:

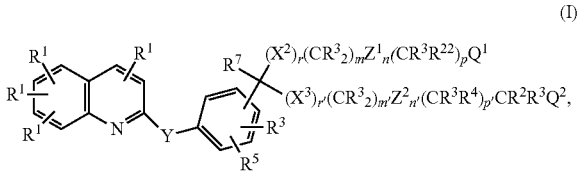

(I)

or a pharmaceutically acceptable ester or salt thereof, where: $R^1$ is H, halogen, —CF$_3$, —CN, —NO$_2$, or N$_3$; $R^2$ is lower alkyl, lower alkenyl, lower alkynyl, —CF$_3$, —CH$_2$F, —CHF$_2$, CH$_2$CF$_3$, substituted or unsubstituted phenyl, substituted or unsubstituted benzyl, substituted or unsubstituted 2-phenethyl, or two $R^2$ groups joined to the same carbon to form a carbocyclic ring of up to 8 members; $R^3$ is H or $R^2$; $R^4$ is halogen, —NO$_2$, —CN, —OR$^3$, —SR$^3$, NR$^3$R$^3$, NR$^3$C(O)R$^7$, or R$^3$; $R^5$ is H, halogen, —NO$_2$, —N$_3$, —CN, —SR$^2$, —NR$^3$R$^3$, —OR$^3$, lower alkyl, or —C(O)R$^3$; R$^6$ is —(CH$_2$)$_s$—C(R$^7$R$^7$)—(CH$_2$)$_s$—R$^8$ or —CH$_2$C(O)NR$^{12}$R$^{12}$; R$^7$ is H or C$_1$-C$_4$ alkyl; R$^8$ is the radical W—R$^9$; R$^9$ contains up to 20 carbon atoms and is (1) an alkyl group or (2) an alkylcarbonyl group of an organic acyclic or monocyclic carboxylic acid; R$^{11}$ is lower alkyl, —C(O)R$^{14}$, unsubstituted phenyl, or unsubstituted benzyl; R$^{12}$ is H or R$^{11}$; R$^{13}$ is lower alkyl, lower alkenyl, lower alkynyl, —CF$_3$ or substituted or unsubstituted phenyl, benzyl, or 2-phenethyl; R$^{14}$ is H or R$^{13}$; R$^{10}$ is H, C$_1$-C$_4$ alkyl, or OH; R$^{17}$ is lower alkyl, lower alkenyl, lower alkynyl, or substituted or unsubstituted phenyl, benzyl, or 2-phenethyl; R$^{10}$ is lower alkyl, lower alkenyl, lower alkynyl, —CF3 or substituted or unsubstituted phenyl, benzyl, or 2-phenethyl; R$^{19}$ is lower alkyl, lower alkenyl, lower alkynyl, —CF$_3$ or substituted or unsubstituted phenyl, benzyl, or 2-phenethyl; R$^{21}$ is H or R$^{17}$; R$^{22}$ is R$^4$, CHR$^7$ OR$^3$, or CHR$^7$SR$^2$; m is 0-8; m' is 2 or 3; n and n' are independently 0 or 1, p and p' are independently 0-8; m+n+p is 1-10 when r is 1 and X$_2$ is O, S, S(O), or S(O)$_2$; m+n+p is 0-10 when r is 1 and X$_2$ is CR$^3$R$^{16}$; m+n+p is 0-10 when r is 0; m'+n'+p' is 2-10; r and r' are independently 0 or 1; s is 0-3; $Q^1$ is —C(O)OR$^3$, 1H (or 2H)-tetrazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O) NR$^{12}$R$^{12}$, —NR$^{21}$C(O)R$^{18}$, —OC(O)NR$^{12}$R$^{12}$, —C(O)R$^{19}$, —S(O)R$^{19}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH; $Q^2$ is OH; W is O, S, or NR$^3$; $X^2$ and $X^3$ are independently O, S, S(O), S(O)$_2$, or CR$^3$ R$^{16}$; with the proviso that at least one is S or SO$_2$; Y is —CR$^3$=CR$^3$— $Z^1$ and $Z^2$ are independently -HET(R$^3$)(R$^5$)—; HET is the diradical of a benzene, a pyridine, a furan, or a thiophene; and, wherein the compound decreases urinary leukotrienes.

The disclosure provides for other aspects and embodiments that will be apparent in light of the following detailed description and accompanying figures.

BRIEF DESCRIPTION OF THE DRAWINGS

FIG. 2A shows an example in which the 120 mg dose is most desirable, and a greater proportion of subjects are randomized to that dose as the study progresses. FIG. 2B shows a treatment time course.

DETAILED DESCRIPTION

Figure 1:
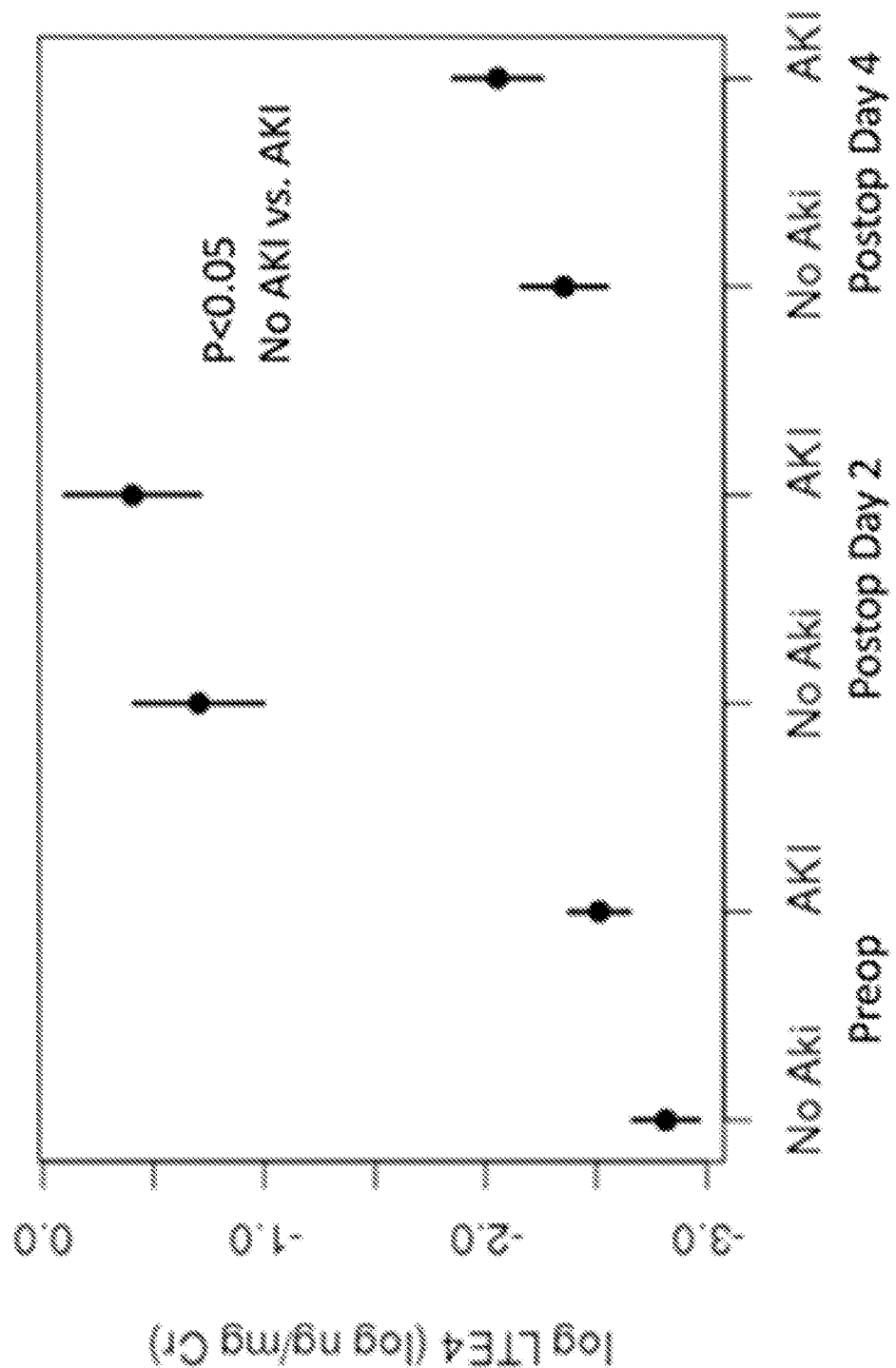
FIG. 1 shows that urinary LTE$_4$ increases after cardiac surgery.

Cardiac surgery serves as a model form of acute kidney injury (AKI) with 'experimental conditions' that enable the investigation of clinically relevant renal injury mechanisms and also the testing of novel therapies. The suitability of cardiac surgery as a model form of AKI is due, in part, to the similarity between mechanisms of cardiac surgery-associated AKI (CSA-AKI), such as inflammation, oxidative damage, and ischemia, and other clinical conditions, a similar degree of renal insult consistently imposed upon a relatively homogenous patient population, known timing of renal insults, and a hospitalized patient population. Features supporting enrollment feasibility and recruitment include the high volume of patients undergoing cardiac surgery, the high incidence of CSA-AKI, and the elective nature of the surgery. The latter feature also allows researchers to adequately measure baseline parameters and schedule assessments linked closely to clinical events. Given these specific characteristics, clinical investigations of CSA-AKI can help decipher pathologic mechanisms of AKI and develop therapies that may also have efficacy in other forms of AKI.

Identification of local renal generation of cysteinyl leukotrienes will better characterize the therapeutic potential of montelukast to affect renal inflammation and AKI. Leukotrienes are arachidonic acid metabolites that regulate inflammation. Leukotrienes are subdivided into the dihydroxy fatty acid leukotriene LTB$_4$ and the cysteinyl leukotrienes LTC$_4$, LTD$_4$, and LTE$_4$. LTC$_4$ and LTD$_4$ are rapidly metabolized systemically, are not present in urine of healthy individuals, and most studies measure LTE$_4$ to assess inflammation. Urinary LTE$_4$ levels may reflect local LTE$_4$ production and increased renal inflammation or filtration of systemically produced LTE$_4$ and extra-renal inflammation. Montelukast may act directly on renal CysLT1 receptors and/or indirectly through amelioration of extra-renal or systemic pathology. An unexplored opportunity to identify renally generated cysteinyl leukotrienes is to measure urinary LTC$_4$ and LTD$_4$, in addition to LTE$_4$. The presence of LTC$_4$ and LTD$_4$ in the urine would signify renal generation of cysteinyl leukotrienes, solidifying the potential of the montelukast AKI therapeutic/indication pairing. Urinary $LTC_4$, $LTD_4$, and $LTE_4$ will be measured using mass spectrometry in biobanked urine samples from patients who did and did not suffer from AKI following cardiac surgery.

Through an NCATS-supported platform using published and publicly available methods to rapidly identify and validate drug repurposing candidates, a phenome-wide association study (PheWAS) was performed within BioVU (Vanderbilt's large-scale DNA biobank). The PheWAS revealed novel associations between single nucleotide polymorphisms (SNPs) in the gene that encodes the protein target of montelukast (CYSLTR1) and multiple clinical renal disease phenotypes. These results are concordant with substantial evidence in animal models that demonstrate that leukotrienes, arachidonic acid metabolites broadly involved in inflammation, contribute to the pathophysiology of various kidney diseases, including AKI. Montelukast is a widely used generic drug that reduces inflammation by binding and blocking leukotriene receptors and is FDA-approved for asthma and allergic rhinitis. Preliminary data show-increased risk of nephritis, nephropathy, and dialysis among rs139639671 missense carriers; increased urinary leukotrienes in patients who develop AKI following cardiac surgery; and 38% reduced risk of AKI among montelukast users compared to non-users in 3,721 adult patients. Described herein are activities and procedures that will support the design and enhance the execution of a clinical trial that will effectively test whether montelukast can be repurposed to prevent cardiac surgery-associated AKI (CSA-AKI).

The methods described herein demonstrate that a safe, affordable generic drug can be used to treat a serious medical condition that affects thousands of patients annually. In addition, the publicly available repurposing method employed herein is generalizable to other drug-indication pairings. A goal of this disclosure is to rapidly accelerate the development of a safe pharmacological approach to treating or preventing disease.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, preferably within 5-fold, and more preferably within 2-fold, of a value.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The term "baseline" as used herein refers to an initial measurement such as measurement of a biomarker. For example, the lowest ever serum creatinine measurement from a body fluid sample may be treated as a baseline.

The term "biomarker" as used herein with regard to a physiological substance such as one of the proteins as described herein. A biomarker may also refer to one or more fragments, variants, etc., of a particular protein and/or peptide or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "body fluid sample" as used herein, refers to any sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing medical condition or the effect of a treatment regimen on a medical condition. Preferred body fluid samples include but are not limited to, blood, serum, plasma, cerebrospinal fluid, urine, saliva, sputum, or pleural effusions. In addition, certain body fluid samples may be more readily analyzed following a fractionation or purification procedure, for example, separation of whole blood into serum or plasma components.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having a kidney disease. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, a value that corresponds to the 25th percentile, the 50th percentile or the 75th percentile, and the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for a protein activity may be defined in accordance with standard practice. A control may be a subject or cell without a compound as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

The term "dose" as used herein denotes any form of the active ingredient formulation or composition that contains an amount sufficient to produce a therapeutic effect with at least a single administration. "Formulation" and "compound" are used interchangeably herein.

The term 'dosage' as used herein refers to the administering of a specific amount, number, and frequency of doses over a specified period of time, typically 1 day.

The term "glomerular filtration rate" as used herein, refers to any measurement capable of determining kidney function. In general, a normal glomerular filtration rate ranges between approximately 120-90 mL/minute per 1.73 m2 of body surface. Compromised kidney function is assumed when glomerular filtration rates are less than 90 mL/minute per 1.73 $m^2$ of body surface. Kidney failure is probable when glomerular filtration rates fall below approximately 30 mL/minute per 1.73 $m^2$ of body surface. Dialysis is frequently initiated when glomerular filtration rates fall below approximately 15 mL/minute per 1.73 $m^2$ of body surface.

As used herein, an "improvement in renal function" is an abrupt (for example, within 14 Days, within 7 Days, within 72 hours, or within 48 hours) measurable increase in a measure of renal function. Such as methods for measuring and/or estimating glomerular filtration rate (GFR).

The term "prophylaxis" refers to preventing or reducing the progression of a disorder, either to a statistically significant degree or to a degree detectable to one skilled in the art.

As used herein, "reduced renal function" is an abrupt (for example, within 14 Days, within 7 Days, within 72 hours, or within 48 hours) reduction in kidney function that may be identified by an absolute increase in serum creatinine of greater than or equal to 0.1 mg/dL (≥8.8 μmol/L), a percentage increase in serum creatinine of greater than or equal to 20% (1.2-fold from baseline), or a reduction in urine output (oliguria of less than 0.5 mL/kg per hour).

The term "renal biomarker" as used herein, refers to any biological compound related to the progressive development of chronic kidney disease. In particular, a renal biomarker may be a kidney injury marker. For example, a renal biomarker may comprise a urinary protein, or any metabolite and/or derivative thereof, wherein the renal biomarker is either overexpressed or underexpressed as a result of an AKI.

"Sample" or "test sample" as used herein can mean any sample in which the presence and/or level of a target is to be detected or determined or any sample comprising a DNA targeting or gene editing system or component thereof as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. The sample comprises an aliquot. The sample may comprise a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject," "study participant," "subject," "participant," and "patient" as used herein interchangeably refers to any vertebrate, including, but not limited to, a mammal that wants or is in need of the herein described compounds, compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male. The subject may be female. The subject has a specific genetic marker. The subject may be undergoing other forms of treatment.

"Treatment" or "treating" when referring to protection of a subject from a disease, means suppressing, repressing, reversing, alleviating, ameliorating, or inhibiting the progress of disease, or completely eliminating a disease. A treatment may be either performed in an acute or chronic way. The term also refers to reducing the severity of a disease or symptoms associated with such disease prior to affliction with the disease. Preventing the disease involves administering a composition or compound of the present invention to a subject prior to onset of the disease. Suppressing the disease involves administering a composition or compound of the present invention to a subject after induction of the disease but before its clinical appearance. Repressing or ameliorating the disease involves administering a composition or compound of the present invention to a subject after clinical appearance of the disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics, and protein and nucleic acid chemistry and hybridization described herein are those that are well known and commonly used in the art. The meaning and scope of the terms should be clear, in the event however of any latent ambiguity, definitions provided herein take precedent over any dictionary or extrinsic definition. Further, unless otherwise required by context, singular terms shall include pluralities and plural terms shall include the singular.

2. KIDNEY INJURY

The term "kidney injury" as used herein, refers to an "injury to renal function" that may be an abrupt (for example, within 14 Days, within 7 Days, within 72 hours, or within 48 hours) measurable reduction in a measure of renal function. Such an injury to renal function may be identified, for example, by a decrease in GFR or estimated GFR (eGFR), a reduction in urine output, an increase in serum creatinine, an increase in urinary leukotrienes, an increase in serum cystatin C, a requirement for renal replacement therapy (for example, dialysis), etc.

A kidney injury may be acute. The term "acute renal disease/failure/injury" as used herein, refers to any progressive worsening of renal function over hours to days, resulting in the retention of nitrogenous wastes (such as urea nitrogen) and creatinine in the blood. Retention of these substances may also be referred to as, azotemia. Current Medical Diagnosis & Treatment 2008, 47th Ed, McGraw Hill, New York, pages 785-815 is incorporated herein by reference in its entirety. As used herein, "acute kidney injury" or "AKI" or "acute renal failure" or "ARF" may be characterized by abrupt deterioration in kidney function, manifested by an increase in serum creatinine level with or without reduced urine output. Specifically, an abrupt (for example, within 14 Days, within 7 Days, within 72 hours, or within 48 hours) reduction in kidney function may be identified by an absolute increase in serum creatinine of greater than or equal to 0.3 mg/dL (z26.4 μmol/L), a percentage increase in serum creatinine of greater than or equal to 50% (1.5-fold from baseline), or a reduction in urine output (oliguria of less than 0.5 mL/kg per hour for at least 6 hours).

The spectrum of injury ranges from mild to advanced, sometimes requiring renal replacement therapy. The spectrum of injury is categorized into stages. The term "Stage I" as used herein may be characterized by an increase in serum creatinine of more than or equal to 0.3 mg/dL (≥26.4 μmol/L) and/or an increase to more than or equal to 150% (1.5-fold) from baseline. Alternatively, the category may be defined by a urine output less than 0.5 mL/kg per hour for more than 6 hours. The term "Stage II" as used herein may be characterized by an increase in serum creatinine to more than 200% (>2-fold) from baseline. Alternatively, the category may be defined by a urine output less than 0.5 mL/kg per hour for more than 12 hours. The term "Stage III" as used herein may be characterized by an increase in serum creatinine to more than 300% (>3-fold) from baseline and/or serum creatinine ≥354 μmol/L accompanied by an acute increase of at least 44 μmol/L. Alternatively, the category may be defined by a urine output less than 0.3 mL/kg per hour for 24 hours or anuria for 12 hours.

A kidney injury may be chronic. Chronic kidney disease (CKD) is a slow and progressive loss of kidney function over a period of several years. Eventually, a person will develop permanent kidney failure. CKD, also known as chronic renal failure, chronic renal disease, or chronic kidney failure, is much more widespread than people realize; it often goes undetected and undiagnosed until the disease is well advanced. It is not unusual for people to realize they have chronic kidney failure only when their kidney function is down to 25 percent of normal. As kidney failure advances and the organ's function is severely impaired, dangerous levels of waste and fluid can rapidly build up in the body. Treatment is aimed at stopping or slowing down the progression of the disease—this is usually done by controlling its underlying cause. The term "chronic renal disease/failure/injury" as used herein, refers to a medical condition wherein exemplary symptoms may include, but are not limited to, hyperphosphatemia (for example, >4.6 mg/dL) or low glomerular filtration rates (for example, <90 mL/minute per 1.73 m2 of body surface). However, many CKD patients may have normal serum phosphate levels in conjunction with a sustained reduction in glomerular filtration rate for 3 or more months, or a normal GFR in conjunction with sustained evidence of a structural abnormality of the kidney. In some cases, patients diagnosed with CKD are placed on hemodialysis to maintain normal blood homeostasis (for example, urea or phosphate levels). Alternatively, "chronic kidney disease" or "CKD" refers to a medical condition wherein a patient has either i) a sustained reduction in GFR<60 mL/min per 1.73 $m^2$ of body surface for 3 or more months; or ii) a structural or functional abnormality of renal function for 3 or more months even in the absence of a reduced GFR. Structural or anatomical abnormalities of the kidney could be defined as, but not limited to, persistent microalbuminuria or proteinuria or hematuria or presence of renal cysts. CKD may also result from an abnormal loss of renal function over months to years. Current Medical Diagnosis & Treatment 2008, 47th Ed, McGraw Hill, New York, pages 785-815 is incorporated herein by reference in its entirety.

a. Cardiac Surgery-Associated Acute Kidney Injury (CSA-AKI)

CSA-AKI is one of the most common causes of AKI and is correlated with increased mortality. The pathophysiology of CSA-AKI is complex and may include renal ischemia-reperfusion injury, inflammation, oxidative stress, hemolysis, and nephrotoxins. Preoperative renal ischemia and reperfusion injury (IRI) is one of the primary causes of CSA-AKI. Renal perfusion is complex and highly regulated. Kidneys are perfused by about 20% of cardiac output, however the majority of blood filtered by cortex glomeruli is shunted away from the vasa recta. This shunt may aid in maintaining the electrolyte and water concentration gradients in the renal medulla required for tubule and collecting system reabsorption. However, as a result, the renal medulla and corticomedullary junction are hypoxic relative to other tissues ($PO_2$ 10-20 mmHg) and this may increase susceptibility to ischemia. Numerous factors during surgery alter renal perfusion leading to damage of tubules at the corticomedullary junction and in the medulla. For example, cardiopulmonary bypass (CPB) provides continuous blood flow that can dysregulate the balance between cortical and medullary perfusion. Increased cortical perfusion results in increased solute transport and may lead to corticomedullary ischemia via increased medullary oxygen consumption. Aorta cannulation and cross-clamping increase atheroemboli to the kidneys, which also induces ischemia as well as inflammation. Other factors during surgery such as sympathetic nervous system activation, endogenous release of catecholamines, and induction of the renin-angiotensin-aldosterone cascade may also impair renal oxygenation.

Cardiac surgery also induces renal and systemic inflammation. Elevated postoperative plasma concentrations of inflammatory cytokines are associated with a subsequent diagnosis of AKI and increased mortality. The mechanisms that increase inflammation during cardiac surgery are not fully understood, but contact activation from the exposure of blood to the CPB circuit, ischemia reperfusion injury, and oxidative damage all contribute. For example, ischemia and reperfusion induce the production of reactive oxygen species, and reactive oxygen species induce inflammation by upregulation of proinflammatory transcription factors, including nuclear factor kappa-B. Cytokines and chemokines recruit neutrophils, macrophages, and lymphocytes into the renal parenchyma. Parenchymal infiltration and activation of these immune cells increases AKI and leads to fibrosis.

Although IRI is a major component of CSA-AKI, it is only one part of the molecular and physiologic milieu. Exposure of blood to the CPB circuit in CSA-AKI contributes to vascular inflammation and dysfunction. The CPB circuit may also contribute to hemolysis/cell-free hemoglobin and oxygen delivery during surgery. Cardiac surgery involving extracorporeal circulation is often associated with alterations in vascular reactivity and permeability due to changes in the expression and activity of isoforms of nitric oxide synthase and cyclooxygenase. Vascular reactivity/dysfunction drives IRI. CPB may induce hemolysis, caused in part by exposure of blood to a non-endothelialized circuit and to mechanical shear stress. The CPB circuit contains a pump, oxygenator, suction catheters, and filters that damage erythrocytes and increase plasma-free hemoglobin. Free hemoglobin depletes circulating haptoglobin and injures the kidneys by catalyzing free-radical production, precipitating with Tamms Horsfall proteins in the renal collecting system, and inducing renal arteriole vasoconstriction by eliminating nitric oxide. In addition, circulating labile iron further increases reactive oxygen species production via the Fenton and Haber Weis reactions, particularly in tissues where free hemoglobin and iron are sequestered, namely the kidney. In a case-control study of AKI patients and risk-matched controls, patients who developed AKI had twice the plasma-free hemoglobin at the end of CPB than those who did not develop AKI, despite similar AKI risk profiles and identical CPB durations in each group. These data suggest that hemolysis and high concentrations of plasma-free hemoglobin, through induction of subsequent injurious mechanisms or from direct effects, may contribute to the development of AKI following cardiac surgery. Cardiac surgery may cause alterations in systemic and tissue-specific determinants of oxygen delivery such as cardiac output, arterial blood pressure, venous pressure, hemoglobin concentration, fraction of inhaled oxygen, hemoglobin oxygen saturation, circulating catecholamines, angiotensin II concentrations, nitric oxide, adenosine, carbon dioxide, and/or oxygen.

b. Extracorporeal Membrane Oxygenation-Associated Acute Kidney Injury (ECMO-AKI)

Extracorporeal membrane oxygenation (ECMO) is an effective therapy for patients with reversible cardiac and/or respiratory failure. AKI can occur in patients treated with ECMO and can evolve into CKD or end-stage renal disease. ECMO can be used in patients recovering from cardiac surgery; triggers inflammation and reduced renal oxygen delivery after surgery, frequently leading to AKI. Also, AKI in patients treated with ECMO is associated with a 4-fold increase in mortality rate. ECMO may contribute to kidney dysfunction through several mechanisms. For example, renal ischemia-reperfusion injury, inflammation, oxidative stress, hemolysis, and nephrotoxins. Exposure of blood to the ECMO circuit stimulates an inflammatory response, which entails activation of neutrophils, and release cytokines, arachidonic acid metabolites (e.g., leukotrienes) and reactive oxygen species, causing widespread microvascular injury and capillary leak. Prolonged use of ECMO also causes hemolysis. ECMO also causes alterations in hemodynamics and blood flow, which impact oxygen delivery to the kidney.

IRI is a heterogenous group of conditions, some of which have features not relevant in the CSA-AKI or ECMO-AKI context such as autoimmunity/autoantibodies or intestinal bacteria translocation. IRI in the context of cardiac surgery or ECMO can be caused by specific procedures that are not relevant in other settings (for example, cardiopulmonary bypass or ECMO circuits). Ischemic syndromes are a heterogeneous group of conditions. If/when vascular inflammation and dysfunction, hemolysis and cell-free hemoglobin, and/or altered oxygen delivery occur in other IRI settings these physiological components occur to a different degree and are caused by different mechanisms than CSA-AKI and ECMO-AKI. There are significant differences between a systemic reduction in perfusion, such as during shock, compared to regional ischemia and reperfusion of a single organ. Further differences are between warm ischemia that may occur during myocardial ischemia and reperfusion and cold ischemia that may occur during organ transplantation when the organ is cooled with a cold perfusion solution following procurement. Specifically, some forms of IRI may include components that are not relevant in the cardiac surgery setting such as autoimmunity/autoantibodies or intestinal bacterial translocation in gastrointestinal IRI.

3. COMPOUNDS FOR TREATMENT OF KIDNEY INJURY

U.S. Pat. No. 5,565,473 is incorporated herein by reference in its entirety. Provided herein are methods for preventing, treating, or reducing the severity of a CSA-AKI in a subject in need thereof by administering a therapeutically effective amount of a compound of Formula I, or a pharmaceutically acceptable salt or ester thereof, or a composition comprising a compound of Formula I, or a pharmaceutically acceptable salt or ester thereof to the subject. U.S. Pat. No. 5,565,473 discloses compounds of Formula I, which disclosure is incorporated herein by reference. Further, provided herein are methods for preventing, treating, or reducing the severity of a ECMO-AKI in a subject in need thereof by administering a therapeutically effective amount of a compound of Formula I, or a pharmaceutically acceptable salt or ester thereof, or a composition comprising a compound of Formula I or a pharmaceutically acceptable salt or ester thereof to the subject.

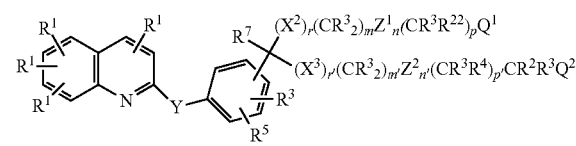

(I)

$R^1$ may be H, halogen, —$CF_3$, —CN, —$NO_2$, or $N_3$; $R^2$ may be a lower alkyl, lower alkenyl, lower alkynyl, —$CF_3$, —$CH_2F$, —$CHF_2$, $CH_2CF_3$, substituted or unsubstituted phenyl, substituted or unsubstituted benzyl, substituted or unsubstituted 2-phenethyl, or two $R^2$ groups joined to the same carbon may form a ring of up to 8 members containing 0-2 heteroatoms chosen from O, S, and N; $R^3$ may be H or $R^2$; $CR^3R^{22}$ may be the radical of a standard amino acid; $R^4$ may be halogen, $-NO_2$, $-CN$, $-OR^3$, $-SR^3$, $NR^3R^3$, $NR^3C(O)R^7$ or $R^3$; $R^5$ may be H, halogen, $-NO_2$, $-N_3$, $-CN$, $-SR^2$, $-NR^3R^3$, $-OR^3$, lower alkyl, or $-C(O)R^3$; $R^6$ may be $(CH_2)_s-(R^7 R^7)-(CH_2)_s-R^8$ or $-CH_2 C(O) NR^{12} R^{12}$; $R^7$ may be H or $C_1$-$C_4$ alkyl; $R^8$ may be a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or the radical W—$R^9$; $R^9$ may contain up to 20 carbon atoms and may be an alkyl group or an alkylcarbonyl group of an organic acyclic or monocyclic carboxylic acid containing not more than 1 heteroatom in the ring; $R^{10}$ may be $-SR^{11}$, $-OR^{12}$, or-$NR^{12}R^{12}$; $R^{11}$ may be a lower alkyl, $-C(O)R^{14}$, unsubstituted phenyl, or unsubstituted benzyl; $R^{12}$ may be H, $R^{11}$ or two $R^{12}$ groups joined to the same N may form a ring of 5 or 6 members containing 1-2 heteroatoms chosen from O, S, and N; $R^{13}$ may be a lower alkyl, lower alkenyl, lower alkynyl, $-CF_3$ or substituted or unsubstituted phenyl, benzyl, or 2-phenethyl; $R^{14}$ may be H or $R^{13}$; $R^{16}$ may be H, $C_1$-$C_4$ alkyl, or OH; $R^{17}$ may be lower alkyl, lower alkenyl, lower alkynyl, or substituted or unsubstituted phenyl, benzyl, or 2-phenethyl; $R^{18}$ may be a lower alkyl, lower alkenyl, lower alkynyl, $-CF_3$ or substituted or unsubstituted phenyl, benzyl, or 2-phenethyl; Rig may be lower alkyl, lower alkenyl, lower alkynyl, $-CF_3$ or substituted or unsubstituted phenyl, benzyl, or 2-phenethyl; $R^{20}$ may be H, $C_1$-$C_4$ alkyl, substituted or unsubstituted phenyl, benzyl, phenethyl, or pyridinyl or two $R^2$ groups joined to the same N may form a saturated ring of 5 or 6 members containing 1-2 heteroatoms chosen from O, S, and N; $R^{21}$ may be H or $R^{17}$; $R^{22}$ may be $R^4$, $CHR^7OR^3$, or $CHR^7SR^2$; m and m' may be independently 0-8; n and m' may be independently 0 or 1; p and p' may be independently 0-8; m+n+p may be 1-10 when r is 1 and $X^2$ is O, S, S(O), or S(O)$_2$; m+n+p may be 0-10 when r is 1 and $X^2$ is $CR^3 R^{16}$; m+n+p may be 0-10 when r is 0; m'+m'+p' may be 0-10; r and r may be independently 0 or 1; s may be 0-3; $Q^1$ may be $-C(O)OR^3$, 1H (or 2H)-tetrazol-5-yl, $-C(O)OR^6$, $-C(O)NHS(O)_2R^{13}$, $-CN$, $-C(O)NR^{12} R^{12}$, $-NR^{21}S(O)_2R^{13}$, $-CN$, $-NR^{12}C(O) NR^{12}R^{12}$, $-NR^{21}C(O)R^{18}$, $-OC(O)NR^{12}R^{12}$, $-C(O)R^{19}$, $-S(O)R^{18}$, $-S(O)_2 R^{18}$, $-S(O)_2 NR^{12}R^{12}$, $-NO_2$, $-NR^{21}C(O)OR^{17}$, $-C(NR^{12}R^{12})=NR^{12}$, $-C(R^{13})=NOH$; or if $Q^1$ is $-C(O)OH$ and $R^{22}$ is $-OH$, $-SH$, $-CHR^7OH$ or $-NHR^3$, then $Q^1$ and $R^{22}$ and the carbons through which they are attached may form a heterocyclic ring by loss of water; $Q^2$ may be OH or $NR^{20}R^{20}$; W may be O, S, or $NR^3$; $X^2$ and $X^3$ may be independently O, S, S(O), S(O)$_2$, or $CR^3R^{16}$; Y may be $-CR^3=CR^3-$ or $-C≡C-$; $Z^1$ and $Z^2$ may be independently -HET($R^3$)($R^5$)—; HET may be the diradical of a benzene, a pyridine, a furan, or a thiophene; and the pharmaceutically acceptable salts thereof.

Abbreviations used herein are defined according to the following: Et=ethyl; Me=methyl; Bz=benzyl; Ph=phenyl; t-Bu=tert-butyl; i-Pr=isopropyl; n-Pr=normal propyl; c-Hex=cyclohexyl; c-Pr=cyclopropyl; 1,1-c-Bu=1,1-bis-cyclobutyl; 1,1-c-Pr=1,1-bis-cyclopropyl (e.g., HOCH2 (1,1-c-Pr)CH2 CO2 Me is methyl 1-(hydroxymethyl)cyclopropaneacetate); c-=cyclo; Ac=acetyl; Tz=1H (or 2H)-tetrazol-5-yl; Th=2- or 3-thienyl; C3 H5=allyl; c-Pen=cyclopentyl; c-Bu=cyclobutyl; phe=benzenediyl; pye=pyridinediyl; fur=furandiyl; thio=thiophenediyl; DEAD=diethyl azocarboxylate; DHP=dihydropyran; DIAD=diisopropyl azodicarboxylate; r.t.=room temperature.

Alkyl, alkenyl, and alkynyl are intended to include linear, branched, and cyclic structures and combinations thereof.

"Alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propyinonyl, 2-(cyclododecyl)ethyl, adamantyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

"Lower alkenyl" groups means alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

"Lower alkynyl" means alkynyl groups of 2 to carbon atoms. Examples of lower alkynyl groups include ethynyl, propargyl, 3-methyl-1-pentynyl, 2-heptynyl, and the like.

"Alkylcarbonyl" means alkylcarbonyl groups of 1 to 20 carbon atom of a straight, branched or cyclic configuration. Examples of alkylcarbonyl groups are 2-methylbutanoyl, octadecanoyl, 11-cyclohexylundecanoyl and the like. Thus, the 11-cyclohexylundecanoyl group is c-Hex-$(CH_2)10$ $-C(O)-$.

Substituted phenyl, benzyl, 2-phenethyl and pyridinyl means structures with 1 or 2 substituents on the aromatic ring selected from lower alkyl, $R^{10}$, $NO_2$, $SCF_3$, halogen, $-C(O)R^7$, $-C(O)R^{10}$, CN, $CF_3$, and $CN_4H$.

Halogen means F, Cl, Br and I.

The prodrug esters of $Q^1$ (i.e., when $Q^1=-C(O)OR^6$) are intended to mean the esters such as are described by Saari et al., *J. Med. Chem.* 1987, 21(8); 746-753, Sakamoto et al., *Chem. Pharm. Bull.* 1984, 32(6); 2241-2248, and Bundgaard et al., *J. Med. Chem.* 1987 30(3); 451-454. Within the definition of $R^8$, some representative monocyclic or bicyclic heterocyclic radicals are: 2,5-dioxo-1-pyrrolidinyl, (3-pyridinylcarbonyl)amino, 1,3-dihydro-1,3-dioxo-2H-isoindol-2-yl, 1,3-dihydro-2H-isoindol-2-yl, 2,4-imidazolinedion-1-yl, 2,6-piperidinedion-1-yl, 2-imidazolyl, 2-oxo-1,3-dioxolen-4-yl, piperidin-1-yl, morpholin-1-yl, and piperazin-1-yl.

When $Q^1$ and $R^{22}$ and the carbons through which they are attached form a ring, the rings thus formed include lactones, lactams, and thiolactones.

It is intended that the definitions of any substituent (e.g., $R^1$, $R^2$, m, X, etc.) in a particular molecule be independent of its definitions elsewhere in the molecule. Thus, $-NR^3R^3$ represents $-NHH$, $-NHCH_3$, $-NHC_6H_5$, etc.

The heterocycles formed when two $R^3$, $R^{12}$, or $R^{20}$ groups join through N include pyrrolidine, piperidine, morpholine, thiamorpholine, piperazine, and N-methylpiperazine.

"Standard amino acids", the radical of which may be $CR^3R^{22}$, means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, and valine. (See F. H. C. Crick, *Symposium of the Society of Experimental Biology.* 1958 12; 140.

Some of the compounds described herein contain one or more centers of asymmetry and may thus give rise to diastereoisomers and optical isomers. The present disclosure is meant to comprehend such possible diastereoisomers as well as their racemic and resolved, optically active forms. Optically active (R) and (S) isomers may be resolved using conventional techniques.

"Isomerism" refers to compounds having the same atomic mass and atomic number but differing in one or more physical or chemical properties. Various types of isomerism include the following identified below.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation.

"Optical isomerism" describes one type of stereoisomerism which manifests itself by the rotation that the isomer, either pure or in solution, imparts to the plane of polarized light. It is caused in many instances by the attachment of four different chemical atoms or groups to at least one of the carbon atoms in a molecule. These isomers may be described as d-, l-, or a d, l-pair or D-, L- or a D,L-pair; or R-, S-, or an R,S-pair, depending upon the nomenclature system employed.

"Diastereoisomer" refers to stereoisomers some or all of which are dissymmetric but which are not mirror images of each other. Diastereoisomers corresponding to a given structural formula must have at least two asymmetric atoms. A compound having two asymmetric atoms will usually exist in four diastereoisomeric forms, i.e. (−)-erythro, (+)-erythro, (−)-threo and (+)-threo.

Some of the compounds described herein contain olefinic double bonds, and unless specified otherwise, are meant to include both E and Z geometric isomers.

As used herein, the terms "salt" or "salts" refer to an acid addition or base addition salt of a compound of the disclosure. "Salts" include in particular "pharmaceutically acceptable salts." The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid and/or base salts by virtue of the presence of amino and/or carboxyl groups or groups similar thereto.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable acid addition salts can be formed with inorganic acids and organic acids. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. The salts may be derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present disclosure provides compounds of Formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

"Pharmaceutically acceptable ester" of the compound of Formula I which may be used in therapy includes those containing the alkanoyloxy group, —O—C(=O)—Z, wherein Z is an alkyl group containing 1 to 12 carbon atoms, which is attached to carbon atom 2 of the propylene linkage instead of the hydroxyl group, i.e., the hydroxy group has been esterified. The group, Z, may be for example, methyl, ethyl, butyl, hexyl, octyl, dodecyl and the like. This disclosure contemplates those compounds of Formula I which are esters as described herein and at the same time are the pharmaceutically acceptable acid addition salts thereof.

a. Montelukast

Montelukast is in the leukotriene receptor antagonists class of medications and is a quinoline. Montelukast may be chemically described as [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetic acid. The empirical formula is $C_{35}H_{35}ClNO_3S$, and its molecular weight is 586.2. The structural formula is shown by Formula II:

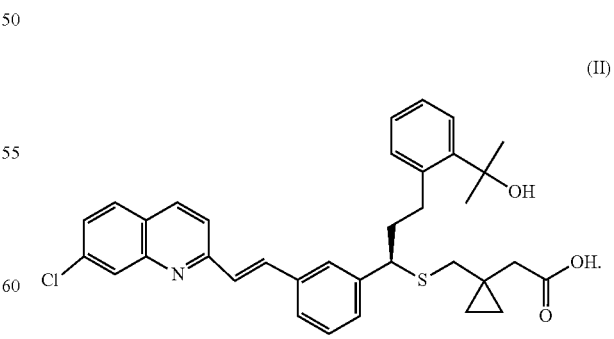

(II)

Montelukast sodium is sold under the tradename SINGULAIR®. SINGULAIR® is available as film-coated tablets, chewable tablets, and oral granules for oral administration. Montelukast sodium is chemically described as [R-(E)]-1-

[[[1-[3-[2-(7-chloro-2-quinolinyl)ethenyl]phenyl]-3-[2-(1-hydroxy-1-methylethyl)phenyl]propyl]thio]methyl]cyclopropaneacetic acid, monosodium salt. The empirical formula is $C_{35}H_{35}ClNNaO_3S$, and its molecular weight is 608.18. The structural formula is shown by Formula III:

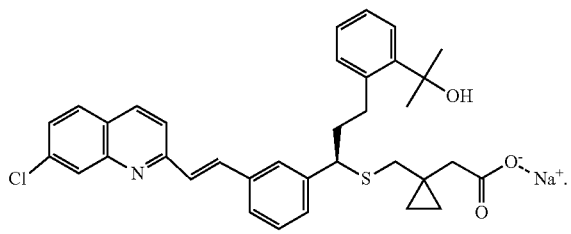

(III)

Provided herein are methods for preventing, treating, or reducing the severity of a CSA-AKI in a subject in need thereof by administering a therapeutically effective amount of a compound of Formula II, or a pharmaceutically acceptable salt or ester thereof, or a compound of Formula III, or a composition comprising a compound of Formula II, or a pharmaceutically acceptable salt or ester thereof, or a composition comprising a compound of Formula III to the subject. Further, provided herein are methods for preventing, treating, or reducing the severity of a ECMO-AKI in a subject in need thereof by administering a therapeutically effective amount of a compound of Formula II, or a pharmaceutically acceptable salt or ester thereof, or a compound of Formula III, or a composition comprising a compound of Formula II or a pharmaceutically acceptable salt or ester thereof, or a composition comprising a compound of Formula III to the subject.

It is used to prevent wheezing, difficulty breathing, chest tightness, and coughing caused by asthma. Montelukast is also used to treat the symptoms of seasonal and perennial allergic rhinitis and to prevent bronchospasm during exercise. The prototype cysteinyl leukotriene receptor antagonist, montelukast, is generally considered to have a niche application in the therapy of exercise- and aspirin-induced asthma. It is also used as add-on therapy in patients whose asthma is poorly controlled with inhaled corticosteroid monotherapy, or with the combination of a long-acting beta(2)-agonist and an inhaled corticosteroid. Recently, however, montelukast has been reported to possess secondary anti-inflammatory properties, apparently unrelated to conventional antagonism of cysteinyl leukotriene receptors. These novel activities enable montelukast to target eosinophils, monocytes, and, in particular, the corticosteroid-insensitive neutrophil, suggesting that this agent may have a broader spectrum of anti-inflammatory activities than originally thought. If so, montelukast is potentially useful in the chemotherapy of intermittent asthma, chronic obstructive pulmonary disease, cystic fibrosis, and viral bronchiolitis, which, to a large extent, involve airway epithelial cell/neutrophil interactions.

Montelukast acts as both a bronchodilator and an anti-inflammatory agent in the lung through its actions on a range of cell types. CysLT1Rs have been cloned and characterized. These receptors have been found on the surface of several structural cells (e.g., epithelial cells and smooth muscle cells) and inflammatory cells (including macrophages, monocytes and eosinophils). CysLT1Rs are known to mediate processes involved in the pathophysiology of asthma and AR, including submucosal edema, airway smooth muscle cell proliferation and contraction, mucus production, as well as recruitment and activation of inflammatory cells, mainly eosinophils. In mice, excessive expression of CysLT1R has been shown to be associated with profound airway eosinophilia, Th2 cytokine production and airway hyperresponsiveness. This is in line with observations by Lehtinen and colleagues, who found increased numbers of eosinophils in airway mucosal biopsies of asthmatic patients after $LTE_4$ inhalation and Diamant et al., who demonstrated sputum eosinophilia following inhalations of $LTD_4$ in patients with similar asthma characteristics. Recent evidence suggests that CysLTs may also play an important role in the process of airway remodeling through a CysLT1R-mediated increase of matrix proteins, including tenascin and laminin. Furthermore, CysLT2R has also been found on a number of inflammatory cells, including monocytes and eosinophils as well as on structural cells, such as epithelial cells, endothelial cells, smooth muscle cells and fibroblasts. Although its role in the pathophysiology of asthma is much less specified, the CysLT2R may be implicated in the process of airway remodeling.

Of the total number of subjects in clinical studies of montelukast, 3.5% were 65 years of age and over and 0.4% were 75 years of age and over. No overall differences in safety or effectiveness were observed between these subjects and younger subjects, and other reported clinical experience has not identified differences in responses between the elderly and younger patients, but greater sensitivity of some older individuals cannot be ruled out. The package insert also indicates that dosage modifications do not appear to be necessary in individuals with decreased kidney function because montelukast is not significantly eliminated via the renal route. The cysteinyl leukotriene pathway may be a unique feature of the form of CSA-AKI or ECMO-AKI intended for treatment.

i) Leukotrienes

Leukotriene synthesis can be activated in a cell (e.g., a leukocyte) by a variety of stimuli. The enzymatic machinery for phospholipase A2 (PLA2)-catalyzed arachidonate hydrolysis and leukotriene synthesis is localized primarily at or near the nuclear membrane, necessitating that leukotriene B4 (LTB4) and leukotriene C4 (LTC4) be transported by carrier proteins out of the cell; the LTC4 transporter is multidrug resistance protein 1; the LTB4 transporter is unknown. In the extracellular milieu, LTC4 is converted to leukotriene D4 (LTD4) and LTD4 to leukotriene E4 (LTE4). Collectively, these molecules make up the cysteinyl leukotrienes. Leukotrienes act on target cells, which may be leukocytes, epithelial cells, smooth-muscle cells, or endothelial cells, by interacting with one or both classes of their cognate receptors. B leukotriene receptor 1 (BLT1) is expressed primarily on leukocytes and is a high-affinity receptor, whereas B leukotriene receptor 2 (BLT2) is expressed more ubiquitously, has a somewhat lower affinity for LTB4, and can bind other lipids. The two cysteinyl leukotriene receptors have a broad distribution. All leukotriene receptors activate the Gq class of G proteins, resulting in increased intracellular calcium, the Gi class, resulting in decreased intracellular cyclic AMP (cAMP), or both. These effects, which activate downstream protein kinases, culminate in myriad cellular and tissue responses.

ii) a Compound of Formula I May Prevent AKI Through Inhibition of Cysteinyl Leukotrienes Leukotriene receptor antagonists (LTRAs), including montelukast, are known to be useful for long-term management of asthma patients complicated by allergic rhinitis (AR) or exercise-induced asthma (EIA). Currently available LTRAs are pranlukast hydrate, zafirlukast, and montelukast. These LTRAs have a bronchodilator action and inhibit airway inflammation, resulting in a significant improvement of asthma symptoms, respiratory function, inhalation frequency of as-needed inhaled P2-agonist, airway inflammation, airway hyperresponsiveness, dosage of ICSs, asthma exacerbations, and patients' quality of life. Although cys-LTs are deeply associated with the pathogenesis of asthma, LTRAs alone are less effective compared with ICS.

A compound of Formula I may prevent vasoconstriction. Cysteinyl leukotrienes are released following cardiac surgery. These leukotrienes reduce renal blood flow and glomerular filtration rate by triggering vasoconstriction; as a leukotriene receptor antagonist, montelukast prevents vasoconstriction. A compound of Formula I may prevent tubular damage. Acute tubular necrosis (ATN) is the term used to designate AKI resulting from damage to the tubules; ischemia resulting from severe or protracted decrease in renal perfusion is one of the two major causes of ATN. Through a compound of Formula I's vasodilation and anti-inflammatory effects, it may prevent ischemia-induced damage.

A compound of Formula I may prevent inflammation. Leukotrienes are important inflammatory mediators; montelukast, as an antagonist, has anti-inflammatory properties and has been shown to attenuate markers of inflammation in animal models. A compound of Formula I may prevent oxidative stress. Leukotrienes are mediators of oxidative stress; leukotriene antagonists such as montelukast have been shown to attenuate markers of oxidative stress in animal models and decrease reactive oxygen species production in humans. A compound of Formula I may also mitigate the damage caused by plasma-free hemoglobin through its effects on the mechanisms described above—vasoconstriction, inflammation, and oxidative stress.

4. PHARMACEUTICAL COMPOSITIONS

Further provided herein are pharmaceutical compositions comprising the above-described compounds of Formula I, or pharmaceutically acceptable salts or esters thereof including compositions comprising a compound of Formula II or a pharmaceutically acceptable salt or ester thereof, as well as compositions comprising a compound of Formula III.

The compounds of Formula I or pharmaceutically acceptable salts or esters thereof as detailed herein, or at least one component thereof, may be formulated into pharmaceutical compositions in accordance with standard techniques well known to those skilled in the pharmaceutical art. The pharmaceutical compositions can be formulated according to the mode of administration to be used. In cases where pharmaceutical compositions are injectable pharmaceutical compositions, they are sterile, pyrogen free, and particulate free. An isotonic formulation may be used. Generally, additives for isotonicity may include sodium chloride, dextrose, mannitol, sorbitol and lactose. In some cases, isotonic solutions such as phosphate buffered saline can be used. Stabilizers include gelatin and albumin.

The composition may further comprise a pharmaceutically acceptable excipient. The pharmaceutically acceptable excipient may be functional molecules as vehicles, adjuvants, carriers, or diluents. The term "pharmaceutically acceptable carrier," may be a non-toxic, inert solid, semi-solid or liquid filler, diluent, encapsulating material or formulation auxiliary of any type. Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. The transfection facilitating agent may be a polyanion, polycation, including poly-L-glutamate (LGS), or lipid.

In another aspect, the present disclosure provides a pharmaceutical composition comprising a compound as described herein, an ester thereof, or a pharmaceutically acceptable salt thereof, and a pharmaceutically acceptable carrier. The composition may comprise at least two pharmaceutically acceptable carriers, such as those described herein. For purposes of the present disclosure, unless designated otherwise, solvates and hydrates are generally considered compositions. Preferably, pharmaceutically acceptable carriers are sterile. The pharmaceutical composition can be formulated for particular routes of administration such as oral administration, intravenous administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. The pharmaceutical compositions are tablets or gelatin capsules comprising the active ingredient together with one or more of: diluents, e.g., lactose, dextrose, sucrose, mannitol, sorbitol, cellulose and/or glycine; lubricants, e.g., silica, talcum, stearic acid, its magnesium or calcium salt and/or polyethyleneglycol; binders, e.g., magnesium aluminum silicate, starch paste, gelatin, tragacanth, methylcellulose, sodium carboxymethylcellulose and/or polyvinylpyrrolidone; disintegrants, e.g., starches, agar, alginic acid or its sodium salt, or effervescent mixtures; and absorbents, colorants, flavors and sweeteners.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions may be prepared according to conventional mixing, granulating or coating methods, respectively, and contain about 0.1-100%, or about 0.1-75%, or about 1-50%, of the active ingredient.

A composition as described herein may comprise from about 5 mg to about 250 mg of a compound of Formula I, or a pharmaceutically acceptable salt or ester thereof as detailed herein. A composition as described herein may comprise about 10 mg to about 250 mg, about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg, about 5 mg to about 120 mg, about 10 mg to about 120 mg, about 20 mg to about 120 mg, about 30 mg to about 120 mg, about 40 mg to about 120 mg, about 50 mg to about 120 mg, about 60 mg to about 120 mg, about 70 mg to about 120 mg, about 80 mg to about 120 mg, about 90 mg to about 120 mg, about 100 mg to about 120 mg, about 110 mg to about 120 mg, about 5 mg to about 60 mg, about 10 mg to about 60 mg, about 20 mg to about 60 mg, about 30 mg to about 60 mg, about 40 mg to about 60 mg, about 50 mg to about 60 mg, about 5 mg to about 20 mg, about 10 mg to about 20 mg, or about 15 mg to about 20 mg of a compound of Formula I or a pharmaceutically acceptable salt or ester thereof as detailed herein. A composition as described herein may comprise at least 5 mg, at least 10 mg, at least 20 mg, at least 30 mg, at least 40 mg, at least 50 mg, at least 60 mg, at least 70 mg, at least 80 mg, at least 90 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, or at least 240 mg of a compound of Formula I or a pharmaceutically acceptable salt or ester thereof as detailed herein. A composition as described herein may comprise at most 250 mg, at most 240 mg, at most 230 mg, at most 220 mg, at most 210 mg, at most 200 mg, at most 190 mg, at most 180 mg, at most 170 mg, at most 160 mg, at most 150 mg, at most 140 mg, at most 130 mg, at most 120 mg, at most 110 mg, at most 100 mg, at most 90 mg, at most 80 mg, at most 70 mg, at most 60 mg, at most 50 mg, at most 40 mg, at most 30 mg, at most 20 mg, or at most 10 mg of a compound of Formula I or a pharmaceutically acceptable salt or ester thereof as detailed herein. A composition as described herein may typically comprise from about 20 mg to about 120 mg of a compound of Formula I esters thereof, or pharmaceutically acceptable salts thereof as detailed herein.

5. ADMINISTRATION

The compounds of Formula I, or pharmaceutically acceptable salts or esters thereof as detailed herein, or at least one component thereof, may be administered or delivered to a subject or a cell of the subject. The compounds of Formula I, or pharmaceutically acceptable salts or esters thereof as detailed herein, or at least one component thereof, may be administered or delivered to a subject or a cell of the subject in a therapeutically effective amount. Such compositions can be administered in dosages and by techniques well known to those skilled in the medical arts taking into consideration such factors as the age, sex, weight, and condition of the particular subject, and the route of administration. To determine the optimal dose a dose escalation will be performed using toxicity-based escalation criteria and dose comparison will be performed using response-adaptive randomization based on efficacy-toxicity assessments that quantify each dose's desirability. This design enhances efficiency (increases power) and addresses the shortcomings of conventional algorithms for determining recommended doses, which are often based on toxicity alone, are not adaptive, and may not find the dose with the best risk-benefit tradeoff for patients. The presently disclosed compounds of Formula I, or pharmaceutically acceptable salts or esters thereof, or compositions comprising the same, may be administered to a subject by different routes including orally, parenterally, sublingually, transdermally, rectally, transmucosally, topically, intranasal, intravaginal, via inhalation, via buccal administration, intrapleurally, intravenous, intraarterial, intraperitoneal, subcutaneous, intradermally, epidermally, intramuscular, intranasal, intrathecal, intracranial, and intraarticular or combinations thereof.

The term "a therapeutically effective amount" of a compound as described herein refers to an amount of a compound as described herein that will elicit a biological or medical response of a subject, for example, reduction or inhibition of an enzyme or a protein activity, or ameliorate symptoms, alleviate conditions, slow or delay disease progression, or prevent a disease or injury, etc.

A subject in need thereof may have an elevated level of serum creatinine, plasma creatinine, or urine creatinine, compared to baseline creatinine levels in the subject or a healthy control subject. The subject may have a single nucleotide polymorphism (SNP) in the gene CYSTLR1. The SNP may be rs139639671 or I123T.

the compositions or compounds described herein may be administered concomitantly with a secondary treatment. The compositions or compounds described herein may be administered once per day, twice per day, or three times per day. The compositions or compounds described herein may be administered to the subject more than once per day. The compositions or compounds described herein may be administered to the subject once per day.

The compositions or compounds described herein may be administered to the subject for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 32 days, at least 33 days, at least 34 days, at least 35 days, at least 36 days, at least 37 days, at least 38 days, at least 39 days, at least 40 days, at least 41 days, at least 42 days, at least 43 days, at least 44 days, at least 45 days, at least 46 days, at least 47 days, at least 48 days, at least 49 days, or at least 50 days following surgery. The compositions or compounds described herein may be administered to the subject for at most 1 day, at most 2 days, at most 3 days, at most 4 days, at most 5 days, at most 6 days, at most 7 days, at most 8 days, at most 9 days, at most 10 days, at most 11 days, at most 12 days, at most 13 days, at most 14 days, at most 15 days, at most 16 days, at most 17 days, at most 18 days, at most 19 days, at most 20 days, at most 21 days, at most 22 days, at most 23 days, at most 24 days, at most 25 days, at most 26 days, at most 27 days, at most 28 days, at most 29 days, at most 30 days, at most 31 days, at most 32 days, at most 33 days, at most 34 days, at most 35 days, at most 36 days, at most 37 days, at most 38 days, at most 39 days, at most 40 days, at most 41 days, at most 42 days, at most 43 days, at most 44 days, at most 45 days, at most 46 days, at most 47 days, at most 48 days, at most 49 days, or at most 50 days following surgery. The compositions or compounds described herein may be administered to the subject for at least 1 day, at least 2 days, at least 3 days, at least 4 days, or at least 5 days before surgery. The compositions or compounds described herein may be administered to the subject for at most 1 day, at most 2 days, at most 3 days, at most 4 days, or at most 5 days before surgery. The compositions or compounds described herein may be administered for the duration that a patient is hospitalized. The compositions or compounds described herein may be administered to the subject prior to surgery, during surgery, after surgery, or a combination thereof.

the compositions or compounds described herein may be administered about 3 hours to about 12 hours apart, about 4 hours to about 12 hours apart, about 5 hours to about 12 hours apart, about 6 hours to about 12 hours apart, about 7 hours to about 12 hours apart, about 8 hours to about 12 hours apart, about 9 hours to about 12 hours apart, or about 10 hours to about 12 hours apart. The compositions or compounds described herein may be administered at least 3 hours apart, at least 4 hours apart, at least 5 hours apart, at least 6 hours apart, at least 7 hours apart, at least 8 hours apart, at least 9 hours apart, at least 10 hours apart, or at least 11 hours apart. The compositions or compounds described herein may be administered at most 12 hours apart, at most 11 hours apart, at most 10 hours apart, at most 9 hours apart, at most 8 hours apart, at most 7 hours apart, at most 6 hours apart, at most 5 hours apart, or at most 4 hours apart.

A subject may be connected to an extracorporeal membrane oxygenation (ECMO) machine. A subject may be administered a compound or composition as described herein at least 30 minutes, at least 1 hour, at least 2 hours, at least 3 hours, at least 4 hours, at least 5 hours, at least 6 hours, at least 7 hours, or at least 8 hours prior to connecting an ECMO machine to the subject. A subject may be administered a compound or composition as described herein at most 1 hour, at most 2 hours, at most 3 hours, at most 4 hours, at most 5 hours, at most 6 hours, at most 7 hours, at most 8 hours, or at most 9 hours prior to connecting an ECMO machine to the subject. The compositions or compounds described herein may be administered to the subject prior to, throughout the duration of, after being connected to the ECMO machine, or a combination thereof.

the compositions or compounds described herein may be administered once in the morning and once in the evening. The compositions or compounds described herein may be administered without food or with food. The compositions or compounds described herein may be administered about 0 minutes, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 120 minutes, or about 150 minutes prior to food consumption. The compositions or compounds described herein may be administered at least 0 minutes, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, or at least 120 minutes prior to food consumption. The compositions or compounds described herein may be administered at most 150 minutes, at most 60 minutes, at most 55 minutes, at most 50 minutes, at most 45 minutes, at most 40 minutes, at most 35 minutes, at most 30 minutes, at most 25 minutes, at most 20 minutes, at most 15 minutes, at most 10 minutes, or at most 5 minutes prior to food consumption. The compositions or compounds described herein may typically be administered about 0 minutes to about 150 minutes prior to food consumption.

The daily dosage of a compound of Formula I, or a pharmaceutically acceptable salt or ester thereof, may be from about 5 mg to about 250 mg. The daily dosage of a compound of Formula I, a pharmaceutically acceptable salt or ester thereof may be about 10 mg to about 250 mg, about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg, about 5 mg to about 120 mg, about 10 mg to about 120 mg, about 20 mg to about 120 mg, about 30 mg to about 120 mg, about 40 mg to about 120 mg, about 50 mg to about 120 mg, about 60 mg to about 120 mg, about 70 mg to about 120 mg, about 80 mg to about 120 mg, about 90 mg to about 120 mg, about 100 mg to about 120 mg, about 110 mg to about 120 mg, about 5 mg to about 60 mg, about 10 mg to about 60 mg, about 20 mg to about 60 mg, about 30 mg to about 60 mg, about 40 mg to about 60 mg, about 50 mg to about 60 mg, about 5 mg to about 20 mg, about 10 mg to about 20 mg, or about 15 mg to about 20 mg. The daily dosage of a compound of Formula I, ester thereof, or pharmaceutically acceptable salt thereof may be at least 5 mg, at least 10 mg, at least 20 mg, at least 30 mg, at least 40 mg, at least 50 mg, at least 60 mg, at least 70 mg, at least 80 mg, at least 90 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, or at least 240 mg. The daily dosage of a compound of Formula I, ester thereof, or pharmaceutically acceptable salt thereof may be at most 250 mg, at most 240 mg, at most 230 mg, at most 220 mg, at most 210 mg, at most 200 mg, at most 190 mg, at most 180 mg, at most 170 mg, at most 160 mg, at most 150 mg, at most 140 mg, at most 130 mg, at most 120 mg, at most 110 mg, at most 100 mg, at most 90 mg, at most 80 mg, at most 70 mg, at most 60 mg, at most 50 mg, at most 40 mg, at most 30 mg, at most 20 mg, or at most 10 mg. The daily dosage of a compound of Formula I, or a pharmaceutically acceptable salt or ester thereof typically may be from about 20 mg to about 120 mg.

Following administration of the presently disclosed compounds of Formula I, or pharmaceutically acceptable salts or esters thereof, or compositions comprising the same, to a subject, the occurrence of CSA-AKI, pathophysiological causes of CSA-AKI, or the symptoms thereof in a subject may be reduced. The pathophysiological causes of CSA-AKI may comprise cardiac surgery-induced physiological changes such as one or more of renal ischemia-reperfusion injury, renal inflammation, systemic inflammation, elevated inflammatory cytokines, elevated reactive oxygen species, oxidative stress, hemolysis, dysregulated renal perfusion, atheroemboli, hemolysis, elevated plasma-free hemoglobin, nephrotoxins, dysregulated cardiac output, dysregulated arterial blood pressure, dysregulated venous pressure, dysregulated hemoglobin oxygen saturation, elevated circulating catecholamines, and elevated angiotensin II concentrations. The symptoms of CSA-AKI may comprise one or more of decreased urine output, swelling in legs, ankles and around the eyes, fatigue or tiredness, shortness of breath, confusion, nausea, seizures or coma in severe cases, chest pain or pressure, feeling sick or being sick, diarrhea, and dehydration.

Following administration of the presently disclosed compounds of Formula I, or pharmaceutically acceptable salts or esters thereof, or compositions comprising the same, to a subject, the occurrence of ECMO-AKI, pathophysiological causes of ECMO-AKI, or the symptoms thereof in a subject may be reduced. The pathophysiological causes of ECMO-AKI may comprise ECMO-induced physiological changes such as one or more of renal inflammation, systemic inflammation, elevated inflammatory cytokines, elevated reactive oxygen species, oxidative stress, reduced renal oxygen delivery, renal ischemia-reperfusion injury, hemolysis, nephrotoxins, and dysregulated hemodynamics and blood flow. The symptoms of ECMO-AKI may comprise one or more of decreased urine output, swelling in legs, ankles and around the eyes, fatigue or tiredness, shortness of breath, confusion, nausea, seizures or coma in severe cases, chest pain or pressure, feeling sick or being sick, diarrhea, and dehydration.

Following delivery of the presently disclosed compounds of Formula I, or pharmaceutically acceptable salts or esters thereof, or compositions comprising the same, to a subject, urinary cysteinyl leukotriene levels are decreased following administration of the compound. Following delivery of the presently disclosed compounds of Formula I, or pharmaceutically acceptable salts or esters thereof, or compositions comprising the same, to a subject, one or more of urinary $LTC_4$, $LTD_4$, $LTE_4$ levels are decreased following administration of the compound.

6. EXAMPLES

The foregoing may be better understood by reference to the following examples, which are presented for purposes of illustration and are not intended to limit the scope of the invention. The present disclosure has multiple aspects and embodiments, illustrated by the appended non-limiting examples.

Example 1

PheWAS Implicated Cysteinyl Leukotrienes in Renal Disease

Using BioVU (Roden et al., *Clin Pharmacol Ther.* 2008, 84(3):362-369; NIH Genomic Data Sharing Policy. National Institutes of Health: Grants. 2014; Bowton E et al., *Science Translational Medicine.* 6(234) 2014), a PheWAS was conducted using genetic and clinical data from 36,000 patients of a SNP in the gene CYSTLR1 (rs139639671 or I123T) and a constellation of kidney-related conditions including nephritis/nephrosis/renal sclerosis (OR=4.75; p=0.003); type 2 diabetes with renal manifestations (OR=4.74; p=0.006); stage I or II CKD (OR=4.75; p=0.013); dialysis (OR=4.38; p=0.017); and hypertensive CKD (OR=2.73; p=0.027) (TABLE 1). CYSTLR1 encodes the cysteinyl leukotriene receptor, which is the target of montelukast. This CYSTLR1 variant was predicted to be deleterious by the SIFT prediction algorithm (Sim N-L et al., *Nucleic Acids Res.* 2012; 40) and benign (i.e. currently no evidence for damaging effect) by the PolyPhen2 algorithm, (Adzhubei I A et al., *Nat Methods.* 2010, 7(4):248-249) although no literature exploring the effects of this variant has been identified. In addition, this SNP was associated with chronic pulmonary heart disease (OR=3.25, p=0.02), a complication of chronic obstructive pulmonary disease (COPD). Montelukast reduces COPD, supporting the validity of the PheWAS. Both the validating (lung disease) and novel (kidney disease) phenotypes were 3-6-fold overrepresented among carriers of this SNP. This PheWAS demonstrated an association between the gene that codes for the CYSTL1 leukotriene receptor (CYSLTR) and kidney disease and led to the present hypothesis that CYSLTR function may impact kidney diseases and that montelukast, a CYSLTR antagonist, could impact AKI. Indeed, a disproportionately high rate of prior postoperative AKI was confirmed in a subset of SNP carriers.

TABLE 1

| Condition | Code | p-value | Odds ratio | Total Cases | Expected* SNP carrier cases | Actual SNP carrier cases | Insights from review of SNP carrier case EHRs |
|---|---|---|---|---|---|---|---|
| PheWAS results validating use of montelukast | | | | | | | |
| Chronic pulmonary heart disease | 415.2 | 0.016 | 3.25 | 1217 | 1 | 6 | 4/6 have asthma and 5/6 had either COPD or pulmonary hypertension |
| PheWAS results uncovering novel use of montelukast | | | | | | | |
| Nephritis; nephrosis; renal sclerosis | 580 | 0.003 | 4.75 | 882 | 1 | 6 | This cluster represents 8 unique patients, 5 of whom also have a history of AKI along with surgeries known to carry increased risk for AKI such as cardiac, bowel, and lung. |
| Type 2 diabetes with renal manifestations | 250.22 | 0.006 | 4.74 | 810 | 1 | 5 | |
| Nephritis and nephropathy without mention of glomerulonephritis | 580.3 | 0.007 | 5.77 | 488 | 0 | 4 | |
| Nephritis and nephropathy in diseases classified elsewhere | 580.31 | 0.009 | 7.42 | 275 | 0 | 3 | |

TABLE 1-continued

| Condition | Code | p-value | Odds ratio | Total Cases | Expected* SNP carrier cases | Actual SNP carrier cases | Insights from review of SNP carrier case EHRs |
|---|---|---|---|---|---|---|---|
| Chronic kidney disease, Stage I or II | 585.4 | 0.013 | 4.75 | 578 | 1 | 4 | |
| Renal dialysis | 585.31 | 0.017 | 4.38 | 661 | 1 | 4 | |
| Hypertensive chronic kidney disease | 401.22 | 0.027 | 2.73 | 1836 | 2 | 7 | |

*Minor allele frequency of rs139639671 is 0.001 and expected cases are rounded to nearest whole number.

Example 2

Cardiac Surgery Patients with AKI have Elevated Postoperative Leukotrienes (LT)

Urinary $LTE_4$ data that VUMC's eicosanoid core had measured in a previous cardiac surgery trial of omega-3 fatty acids to prevent atrial fibrillation following cardiac surgery and $LTC_4$, $LTD_4$, and $LTE_4$ data from a small AKI case-control study using Statin and ROCS trial cohorts were obtained (Mozaffarian D et al., *JAMA*. 2012, 21; 308(19): 2001-2011; Aim 2 of the U34 trial planning grant). Urinary $LTE_4$ concentrations increased significantly following cardiac surgery and were higher in patients diagnosed with AKI (FIG. 1). In the case-control study, urinary $LTC_4$ (marker of renal LT production) was 75% higher on postoperative day 2 in AKI subjects (95% CI: 8 to 183%; P=0.022), compared to non-AKI subjects matched on age, sex, eGFR, COPD, and smoking. In addition, a significant inverse relationship between urinary $LTE_4$ and urinary creatinine was found, indicating that increased $LTE_4$ may be associated with decreased eGFR. These data support the investigation of leukotriene antagonism to impact AKI.

Example 3

Montelukast Use is Associated with Reduced Risk of AKI

Epidemiologic EHR data from Vanderbilt's 'Synthetic Derivative' was examined to determine whether montelukast use is associated with decreased AKI. Individuals eligible for inclusion in the dataset included those with two or more serum creatinine labs occurring after montelukast gained marketing approval (N=3,721), and children were excluded. Montelukast users were defined as those with ≥23 mentions of montelukast where 22 mentions are 230 days apart (N=147). AKI was defined as a ≥21.5-fold serum creatine increase from baseline (N=1,220). 'Case users' were defined as those who qualified as both an AKI case and a montelukast user (N=58). Crude and adjusted odds ratios (OR) and 95% confidence intervals (CI) were calculated using logistic regression. Montelukast users had 38% reduced odds of AKI (95% CI: 13 to 56%) compared to non-users, adjusted for race (black/white/other), sex (male/female), age, body mass index (BMI), and asthma (yes/no).

Example 4

Establishment of Baseline Characteristics

Baseline characteristics were established to estimate AKI rates. A cohort study of all major cardiac surgery cases at VUMC from 2009-2020 was conducted and eligible patients with and without an outcome enrichment strategy that required AKI risk factors for study participation were calculated. 4,718 of the 11,745 patients (40.2%) were excluded because they failed exclusion criteria (montelukast users; ESRD; emergent, VAD, transplant, or OpCAB surgery; etc.; TABLE 2). Outcome enrichment (2 or more AKI risk factors, TABLE 2) included 3,168 (45.1%) of the 7,027 eligible patients. Stage 1, 2, and 3 Kidney Disease Improving Global Outcomes (KDIGO) AKI rates (KDIGO Clinical Practice Guideline for Acute Kidney Injury. 2012, 2(1)), dialysis, and death affected 21.2%, 5.6%, 3.2%, 2.1%, and 3.0% of eligible patients and 28.4%, 7.5%, 4.6%, 3.2%, and 4.5% of the outcome-enriched population, respectively. This preliminary study establishes broad inclusivity and feasibility in an at-risk patient population and demonstrates advantages of including risk factors (outcome enrichment) to identify patients at risk of AKI who may benefit from treatments as described herein.

TABLE 2

| Inclusion Criteria | Exclusion Criteria |
|---|---|
| 1. Age ≥18 years | 1. History of intolerance to montelukast |
| 2. Elective cardiac surgery, defined as surgery on the heart or aorta that requires sternotomy or thoracotomy | 2. Current diagnosis of bronchial asthma or exercise-induced bronchospasm and currently on montelukast or other leukotriene receptor antagonists (zafirlukast, pranlukast) |
| 3. Planned use of CPB during surgery | |
| 4. Two or more AKI risk factors from the list below: | 3. Pregnancy or breastfeeding |
| Age at screening ≥70 years | 4. Diagnosis of schizophrenia, Parkinson's, or multiple sclerosis |
| Combined surgery defined as CABG + valve, two or more valves, CABG + aorta, or valve + aorta | 5. Renal replacement therapy (RRT) within 30 days prior to screening |
| History of chronic kidney disease (CKD), defined as eGFR <60 mL/min per 1.73 m², using the CKD-EPI formula | 6. eGFR <15 mL/min per 1.73 m² per CKD-EPI or MDRD equation within 30 days prior to screening |
| History of congestive heart failure (CHF) defined as: | 7. AKI present at time of surgery, according to KDIGO creatinine criteria |

TABLE 2-continued

| Inclusion Criteria | Exclusion Criteria |
| --- | --- |
| CHF requiring hospitalization in the last year or<br>LVEF ≤30% by echocardiogram or heart cath<br>History of diabetes mellitus (type 1 or 2)<br>History of proteinuria/albuminuria in the last year defined as:<br>Urinary dipstick with ≥2 + proteinuria/albuminuria,<br>Urinary albumin creatinine ratio measurement of ≥300 mg/g, or<br>Total quantity of protein in a 24-hour urine collection test ≥0.3 g/day | 8. Prior kidney transplantation<br>9. History of significant liver dysfunction, defined as transaminases greater than 3 times the upper limit of normal, serum bilirubin >3 mg/dl, or a diagnosis of cirrhosis<br>10. Patients who refuse blood transfusion<br>11. Active endocarditis<br>12. Surgery scheduled to be performed with circulatory arrest<br>13. Surgery scheduled for aortic dissection, ventricular assist device (VAD) placement, or heart transplantation<br>14. Extracorporeal Membrane Oxygenation (ECMO) in place at surgery<br>15. VAD therapy in place at time of surgery |

Example 5

Proposed Clinical Trial of Montelukast for CSA-AKI

Study design. A dose-escalating, two-stage, adaptive design to measure efficacy while monitoring and maintaining subject safety will be used. Treatment will begin prior to surgery on the morning of surgery and will continue daily until postoperative day 7 or hospital discharge, whichever occurs sooner. The primary outcome is an 8-level AKI ordinal outcome based on the KDIGO criteria that will be assessed daily for 7 days; sensitivity outcomes include other metrics of AKI, including any KDIGO AKI, moderate/severe KDIGO AKI, and dialysis; and secondary efficacy outcomes include other organ injuries common in cardiac surgery and impacted by acute inflammation (Khwaja, NEC. 2012,120(4):c179-c184; Leaf et al., *Am J Kidney Dis.* 2017, 69(1):108-116; Palevsky, *Nephron.* 2018, 140(2):111-115; Marrazzo et al., *BMJ Open.* 2019, 9(7):e026848; Garg et al., *BMJ Open.* 2014, 4(3):e004842; Garg et al., *J Am Soc Nephrol.* 2019, 30(7):1294-1304). The primary safety outcome is a composite of hepatitis, neurologic, cardiac, infectious, and serious adverse events.

Patient Sample, Site Selection, and Recruitment Feasibility. 580 patients across 7 sites will be recruited. This number of subjects is required to detect an adequate signal for efficacy while ensuring safety in a high-risk patient population with high rates of morbidities. Collaborating sites with a history of successful cardiac surgery clinical trial performance, stand-alone clinical trial support services, and heterogeneity of hospital structure (University medical center, large clinical enterprise, and community hospitals) and patient population (regional and socioeconomic diversity) were selected. This is the path to advance this therapeutic/indication pairing to a phase III study and ultimately, if successful, to thousands of surgical patients and other forms of AKI. Eligible participants include those undergoing elective open-heart cardiac surgery with cardiopulmonary bypass (CPB)—most often coronary artery bypass grafting (CABG), valve, and/or ascending aorta surgery—and with a moderate or high risk for developing AKI based on presence of 2 or more AKI risk factors (TABLE 2). This outcome enrichment strategy increases the efficiency of the trial and reduces the sample size required to detect a clinically meaningful effect while also enabling inclusion of a large proportion of the cardiac surgery patient population. The exclusion criteria are designed to ensure patient safety and scientific integrity of the study. Participants will not be excluded based on sex/gender, spoken language, race, ethnicity, or country of origin.

Participants will be recruited during their preoperative surgical or anesthesia clinic appointments, in the hospital ward, in surgery holding, or using other site-specific recruitment methods. over 1,400 cardiac surgery patients have been recruited into perioperative interventional clinical trials using these methods (7,080 subjects across all sites in last 10 years). Based on analysis of the 11,745 patient EHR cohort, it is anticipated that approximately 45% of elective on-pump cardiac surgery patients to be eligible, 5,220 of the 11,600 patients per year across all sites. Given the annual volume of cardiac surgery patients at these centers (even during COVID-19), the track record of recruitment, and the short study timeline, this study is highly feasible and does not require advanced recruitment and retention strategies to study 580 patients over 30 months.

Study Procedures. Participants will be randomly assigned to one of four study arms (three oral montelukast dosing regimens or matching placebo) depending on study phase and adaptive randomization, begin taking study drug preoperatively at least one hour before start of surgery and then daily until postoperative day 7 or hospital discharge, whichever occurs sooner.

Blood and urine specimens will be collected at a specific timepoints, centrifuged, and supernatant stored for biomarker analysis. Serum creatinine is measured prior to surgery and then daily postoperatively until hospital discharge to quantify AKI using KDIGO criteria (Khwaja, NEC. 2012,120(4):c179-c184; Leaf et al., *Am J Kidney Dis.* 2017, 69(1):108-116; Palevsky, *Nephron.* 2018, 140(2):111-115; Marrazzo et al., *BMJ Open.* 2019, 9(7):e026848; Garg et al., *BMJ Open.* 2014, 4(3):e004842; Garg et al., *J Am Soc Nephrol.* 2019, 30(7):1294-1304). Baseline characteristics (demographics, past medical history), procedural exposures (type of surgery, cardiopulmonary bypass variables, medication exposures), and postoperative events (adverse events, outcomes) will be recorded using REDCap, a secure, web-based application developed at Vanderbilt and now used worldwide to support data capture for research studies (Hamis et al., *J Biomed Inform.* 2009, 42(2):377-381). REDCap provides validated and uniform data entry across sites, creates audit trails for tracking data entry, protects data, and exports data to statistical packages.

Randomized Treatment Assignment and Blinding. All drug administration will be double-blind, and site Investigational Pharmacies will be responsible for study drug storage, labeling, assignment, and dispensing. Belmar Pharma Solutions will formulate, test, and provide identical tablets containing the three montelukast dose strengths and matching placebo so that participants in all arms take only one tablet daily. The site pharmacy will receive orders for subject enrollment and a prescription for study drug from study coordinators. Using the randomization assignment list created by a biostatistician, the pharmacist will assign the subject to placebo or drug, record the assignment, and dispense the appropriate unidentifiable tablets. Randomization during the dose escalation phase will be stratified by site and presence of CKD (eGFR<60 mL/min/1.73 m$^2$) in permuted blocks of block size 2 or 4.

Figure 2A:
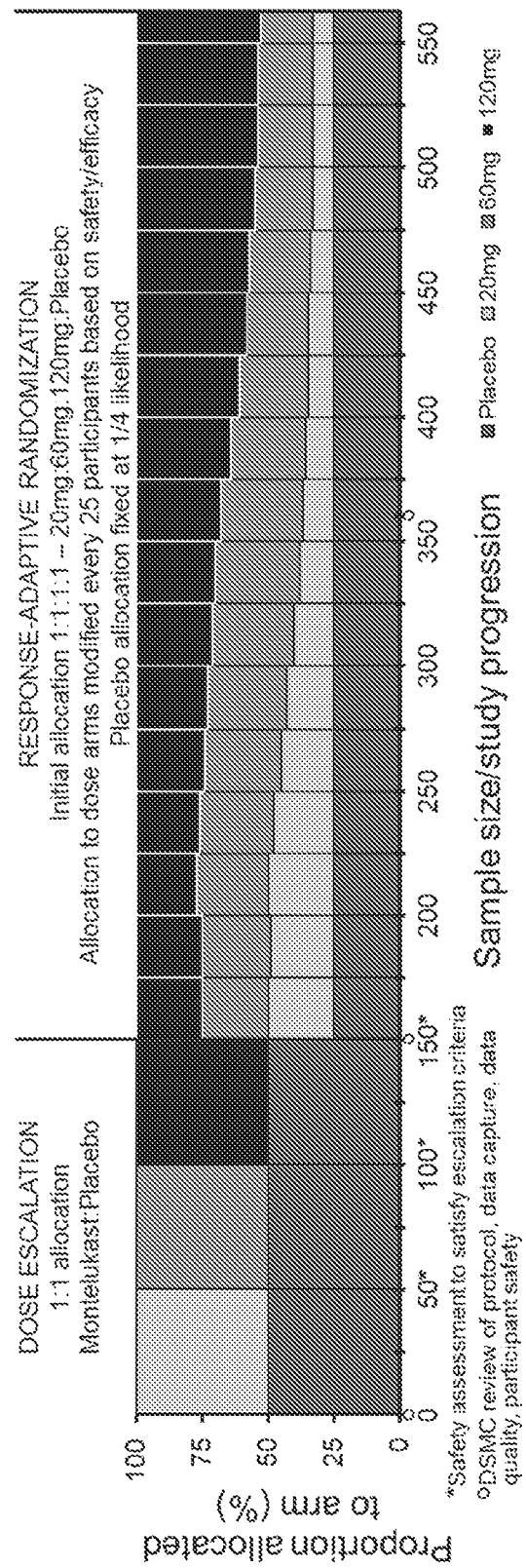
FIG. 2A-B shows the dose escalation stage assessment of safety and feasibility and the response-adaptive randomization stage determines the dose that maximizes "desirability" (best safety and efficacy).
Figure 2B:
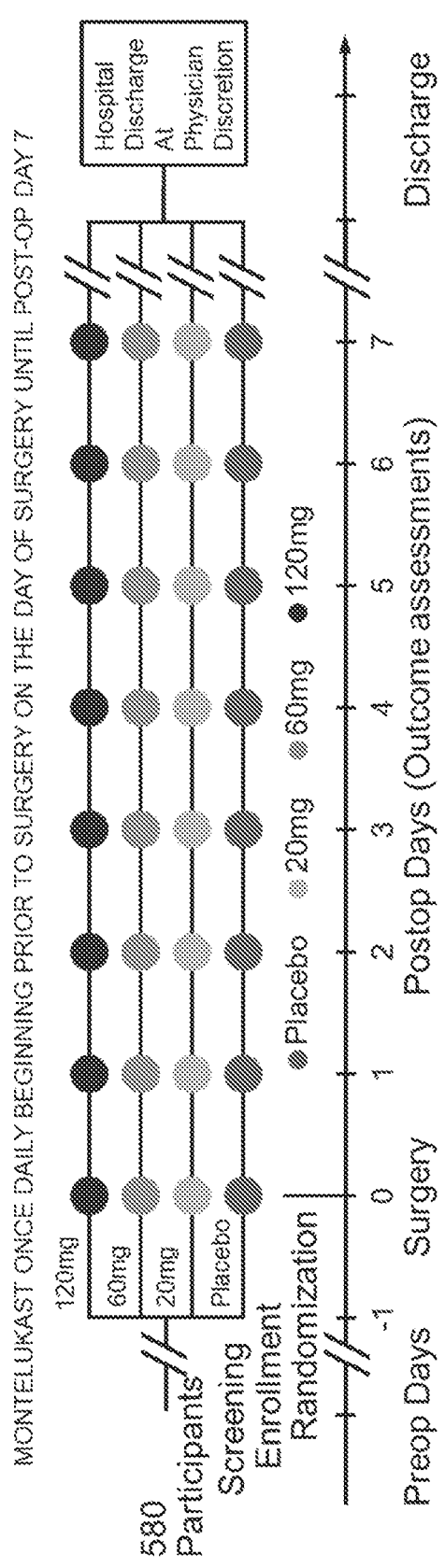

Montelukast dosing rationale and safety. Montelukast has a rapid onset of action. In asthma clinical trials, a single oral dose of 10, 100, or 250 mg significantly improved forced expiratory volume in 1 second (FEV1) within 1 hour of administration, and these effects were maintained for a 24-hour period. The half-life of montelukast is 5 hours, and steady state plasma levels are achieved on Day 2 of dosing. Higher doses, such as 200 mg three times per day, failed to increase FEV1 more than 10 mg once daily, but a dose-dependent increase in plasma concentration was observed in dose ranging study of 20-800 mg. This demonstrates increased bioavailability at higher doses, and the optimal dose to affect AKI is unknown. The pharmacokinetics and pharmacodynamics of oral montelukast during cardiac surgery are also unknown. 20 mg, 60 mg, and 120 mg daily doses will be tested, treatment will be initiated 1-2 hours prior to surgery, and treatment will be continued for 7 days (FIG. 2B). LTE$_4$ may remain elevated until at least postoperative day 7, and KDIGO consensus criteria for AKI diagnosis include a 7 day observation period.

Other pharmacokinetic and safety features of montelukast are also favorable. The pharmacokinetics of oral montelukast 10 mg are similar in elderly volunteers (aged ≥65 years) and younger adults (aged 20 to 45 years), suggesting that dosing adjustments are not required for elderly patients. Montelukast has a low potential for drug-drug interactions. Dosage adjustments are also not required in those with renal or mild to moderate hepatic dysfunction. Single doses of 800 mg and 200 mg three times per day for 10 days have been tested with no significant adverse events.

In early studies of leukotriene synthesis inhibitors (as opposed to CYSLTR antagonists like montelukast), mild liver toxicity was noted in a small percentage of patients. Also, in phase IV post marketing studies, a concern for neuropsychiatric disturbances was noted in chronic montelukast users, prompting a warning from the FDA. Additional research did not support this finding, and this potential toxicity is not relevant for patients recovering from cardiac surgery receiving 7 days of treatment. Nonetheless, patients with baseline hepatitis and neuropsychiatric events/diagnoses will be excluded, and hepatitis and neuropsychiatric events will be included in the safety outcome composite.

Example 6

Testing the Hypothesis that Perioperative Montelukast Treatment is Safe in Cardiac Surgery Patients and Impacts Postoperative AKI The trial consists of two stages: a dose-escalation stage and a response-adaptive-randomization stage. The dose escalation stage will use toxicity-based safety criteria and the response-adaptive randomization stage will use an efficacy-toxicity tradeoff that quantifies each dose's desirability in order to safely evaluate efficacy vs. placebo, and to determine the most desirable dose. (FIG. 2A). Primary, secondary, and safety analyses of treatment will use data from both stages combined.

Dose escalation stage. A dose escalation strategy will be implemented in the first 150 participants to evaluate the safety of montelukast in this patient population/setting at 3 doses (20 mg, 60 mg, and 120 mg). Each dose will be evaluated in blocks of 50 patients. Escalation to a higher dose will occur only when the safety criterion is met at the lower dose. All doses that meet the safety criterion will be included in (i.e., "graduate to") the subsequent response-adaptive randomization stage of the trial, described below. The safety criterion uses a binary composite safety outcome assessed daily in each participant. Mixed-effects logistic regression will be used to quantify the effect of montelukast on the odds of safety events at each dose level versus placebo (the "safety odds ratios"). The safety criterion is met if the lower bound of the 95% confidence interval is not greater than 1.3. The 1.3 threshold was selected because it corresponds (approximately) to a 3 percentage-point difference (13% vs 16%) in the seven-day incidence of the composite safety endpoint, based on two clinical trials completed by our group (Billings et al., *JAMA*. 2016, 315(9):877-888; Lopez et al., *Trials*. 2017, 18(1):295). For example, if the lower limit of the 95% confidence interval of the safety composite is 16% in a treatment group and the rate of the safety composite is 13% in the placebo group, that dose would not graduate.

Response-adaptive randomization stage. A response-adaptive randomization will be implemented in the remaining 430 participants following dose escalation to evaluate montelukast feasibility, efficacy, and safety at all dose levels that graduate from dose-escalation stage. The randomization probabilities among placebo and the montelukast arms will be equal at the start of the second stage and will then be adjusted in response to accumulating evidence of the tradeoff between efficacy and toxicity, or "desirability", among the different dose levels (placebo will remain constant; Yan et al., *Annals of Oncology*. 2018, 29(3):694-699). The "desirability" of each dose is computed as the ratio of the efficacy odds ratio (reduced AKI vs placebo, using the method described below under Statistical analysis plan for primary outcome) and the safety odds ratio (reduced composite safety events vs placebo, using the method described above under Dose escalation stage). Following completion of every 25th participant, the unblinded statistician will use a bootstrap procedure to estimate, for each dose level, the probability that the maximum desirability occurs at that dose level (i.e., the "maximum desirability probability"). The next 25 patients will then be randomly allocated in proportion to the maximum desirability probabilities. For example, if the desirability probabilities are 0.2, 0.3, and 0.5 for 20 mg, 60 mg and 120 mg dose levels, the next 25 patients will be randomized: 25.0% placebo, 0.20·0.75=15.0% 20 mg, 0.3·0.75=22.5% 60 mg, and 0.5·0.75=37.5% 120 mg.

Primary clinical efficacy outcome. The primary outcome is an 8-level AKI ordinal outcome scale, assessed daily from surgery to postoperative day 7 or hospital discharge, and based on the well-validated and accepted KDIGO consensus criteria for AKI diagnosis (Khwaja, NEC. 2012,120(4): c179-c184; Leaf et al., *Am J Kidney Dis*. 2017, 69(1):108-116; Palevsky, *Nephron*. 2018, 140(2):111-115; Marrazzo et al., *BMJ Open*. 2019, 9(7):e026848; Garg et al., *BMJ Open*.

2014, 4(3):e004842; Garg et al., *J Am Soc Nephrol.* 2019, 30(7):1294-1304). This type of longitudinal ordinal outcome provides both increased statistical efficiency and granular, disease-specific quantification of benefits and harms at the patient level (Evans et al., *Clin Infect Dis. Oxford Academic;* 2015, 61(5):800-806; Evans et al., *Clin Trials.* 2020, 17(6): 617-626; Roozenbeek et al., *Crit Care.* 2011, 15(3):R127). This specific outcome provides discrepancy among different KDIGO stages of AKI, yet also captures both more and less severe kidney-related injury and significantly increases statistical power compared to binary outcomes (Roozenbeek et al., *Crit Care.* 2011, 15(3):R127). The daily longitudinal assessment of patients further increases power and allows us to differentiate participants who develop AKI that resolves from participants who develop AKI that persists. Persistent AKI has major implications for long-term poor outcomes. The scale is derived from data captured during routine clinical care, which demonstrates its high feasibility and ability to be adopted by other perioperative clinical trials that consider renal endpoints, and this type of outcome has been recommended as appropriate for Phase II clinical trials of AKI by the NIH and clinical experts in consultation with the FDA. An 8-level scale as compared to a 4-level scale for example, provides enhanced opportunity to detect treatment effects and determine if montelukast should be advanced to a phase III clinical trial. KDIGO Stage 1 AKI is divided into two levels based on the 0.3 mg/dl or the 50% increase in serum creatinine criteria, consistent with a large retrospective cohort study in hospitalized patients that demonstrated that these two Stage 1 AKI subpopulations have significant differences in severity of clinical outcomes. The scale also includes dialysis and mortality, which have been identified as critical endpoints to include in perioperative clinical trials of AKI. This contrasts with historic AKI endpoints that are encumbered by inability to differentiate different severities of AKI, for example any AKI yes/no (RIFLE, AKIN, or KDIGO), or have been insensitive and lacked power to detect important treatment effects, for example moderate/severe AKI or dialysis yes/no. However, both the 8-level AKI ordinal outcome scale daily for 7-days following surgery or until hospital discharge and other common metrics of perioperative AKI as sensitivity outcomes will be measured (TABLE 3). This strategy provides an excellent opportunity to test the hypothesis that montelukast reduces AKI in the setting of a phase II trial where the goal is to detect a preliminary signal of efficacy and generate evidence aimed to provide substantial support for continuing on to a phase III trial, during which a hard renal outcome at 30 days would be chosen.

TABLE 3

Study outcomes and criteria

| AKI KDIGO ordinal outcome scale | |
|---|---|
| 1 | No AKI, serum creatinine (SCr) decrease from baseline |
| 2 | No AKI, 0.0-0.3 mg/dL increase in SCr |
| 3 | Stage 1 AKI, 0.3 mg/dL increase in SCr <48 hours |
| 4 | Stage 1 AKI, 1.5-1.9 fold increase in SCr ≤7 days |
| 5 | Stage 2 AKI, 2-2.9 fold increase in SCr ≤7 days |
| 6 | Stage 3 AKI, ≥3 fold increase in SCr in ≤7 days |
| 7 | Stage 3 AKI, dialysis prior to discharge |
| 8 | Death prior to discharge |

AKI sensitivity outcomes

Any KDIGO stage AKI (Stage 1, 2, or 3; yes/no)
Moderate/Severe KDIGO AKI (Stage 2 or 3; yes/no)

TABLE 3-continued

Study outcomes and criteria

Peak delta serum creatinine ≤7 days from baseline
Dialysis prior to discharge (yes/no)

Safety outcome composite

| Hepatitis | Transient ischemic attack |
|---|---|
| Myocardial infarction | Infection |
| Ventricular arrythmia | Pneumonia |
| Neuropsychiatric events | SAEs (including mortality) |
| Stroke | |

Secondary efficacy outcomes

| Atrial fibrillation | Reintubation |
|---|---|
| Delirium | ICU readmission |
| Neurocognition | Mortality |

Safety/toxicity outcome. A composite safety outcome consisting of hepatic, neurologic, cardiac, and infectious acute events as well as additional uncategorized SAEs will be used. These include hepatitis, defined as transaminases greater than 3 times the upper limit of normal measured on postoperative day 2 (POD2), POD4, and as clinically indicated; ventricular arrhythmia requiring direct current cardioversion; Q-wave or STEMI myocardial infarction; neuropsychiatric events including suicide ideation ascertained during daily follow-up; stroke, defined as a focal neurologic deficit confirmed by imaging (CT or MRI) that does not resolve; transient ischemic attack, defined as a focal neurologic deficit that resolves during hospitalization; infection, defined as initiation of antibiotics following surgery that are not part of perioperative antibiotic prophylaxis; and pneumonia, defined as infection with clinical documented suspicion of pneumonia based on CXR findings and/or sputum culture. Rates of all safety outcomes and the composite will be compared between treatment groups rather than external benchmarks, eliminating bias relative to application of diagnostic criteria.

Secondary efficacy outcomes were selected based on other acute organ injuries common in this patient population and associated with perioperative inflammation and therefore potentially affected by montelukast. These secondary efficacy endpoints include atrial fibrillation, defined as any postoperative atrial fibrillation confirmed with an ECG or rhythm strip; delirium incidence, severity, and duration using twice daily Richmond Agitation-Sedation Scale (RASS; Sessler et al., *Am J Respir Crit Care Med.* 2002, 166(10):1338-1344) and Confusion Assessment Method (CAM) assessments (CAM-ICU and CAM-ICU-7; Ely et al., *JAMA.* 2001, 286(21):2703; Khan et al., *Critical Care Medicine.* 2017, 45(5):851-857; Lindroth et al., *Ann Am Thorac Soc.* 2020, 17(9):1094-1103); neurocognition, measured using the Montreal Cognitive Assessment (MoCA; Nasreddine et al., *Journal of the American Geriatrics Society.* 2005, 53(4):695-699) at baseline and post-op day 5+/− one day; reintubation; intensive care unit (ICU) readmission; and mortality.

Statistical Analysis Plan. The effect of montelukast on the primary efficacy endpoint will be assessed by comparing drug arms to placebo. Data from both stages will be used, but only drug doses that graduated from the dose-escalation stage will be evaluated in the efficacy analysis. For each dose level, the effect of montelukast versus placebo will be estimated on the 8-level ordinal endpoint using an odds ratio with 95% confidence interval, using mixed-effects ordinal logistic regression ("efficacy odds ratios"). These odds ratios represent, for any level of the ordinal outcome, the effect of the intervention on the odds of a poorer outcome (more severe level). For example, an odds ratio of 0.8 indicates 20% less odds of AKI (any level), dialysis, or death in participants treated with montelukast compared to placebo. To test for efficacy, the null hypothesis that there is no effect of montelukast at any dose will be simultaneously tested. This will be implemented using a single, simultaneous, multiple degree-of-freedom test. A statistical simulation will be used to ensure a type-I error rate of 5%, accounting for dose escalation, response adaptive randomization, and interim analyses. Regression analysis will be adjusted for time (postoperative day); factors associated with leukotriene agonism including COPD, smoking, and asthma; and risk factors for AKI, including age, sex, and eGFR. Heterogeneity among participants will be modeled using a random intercept term. Quantitative covariates will be modeled using a flexible nonlinear splines method. Graphical and quantitative regression diagnostics will be examined, including the repeated dichotomization method to assess the proportional odds assumption.

The primary statistical analysis takes full advantage of the ordinal and longitudinal nature of the AKI ordinal outcome, and does not require summarization across time points, nor across levels of the ordinal endpoint. These features will allow for full exploitation of the granularity of the primary endpoint and are partly responsible for the efficiency of this study design (high power). Nevertheless, to facilitate communication about drug effects on the primary endpoint, and in addition to the efficacy odds ratios, a number of clinically relevant summaries of the primary endpoint will be computed and those will be analyzed as sensitivity endpoints. These summaries will include the proportion of participants who develop any AKI or moderate/severe AKI (KDIGO criteria), peak serum creatinine within 7 days of surgery, the proportion of participants who recover from AKI prior to hospital discharge (creatinine returns to within 0.3 mg/dl of baseline), and the incidence of dialysis.

As a secondary endpoint, the three dose levels will also be directly compared with respect to their efficacy-safety profile, or "desirability" as defined above under Response-adaptive randomization stage. To implement this analysis, the relative desirability between each pair of dose levels will be computed as the ratio of the respective desirability measures. These quantities will be presented with bootstrap-based 95% confidence intervals and will allow for reporting both the most effective dose and the most "desirable" dose, which may be the same dose, for example, 60 mg or 120 mg.

Power and sample size justification. The study design, including dose escalation and response-adaptive randomization were examined using extensive statistical simulation. These simulations were used to ensure a 5% type-I error probability for the end-of-study test of overall efficacy and to assess statistical power and sample size requirements. Baseline safety and ordinal outcome event rates and composite safety endpoint rates were established based on data from 815 cardiac surgery patients who participated in two previously completed interventional clinical trials (Billings et al., *JAMA*. 2016, 315(9):877-888; Lopez et al., *Trials*. 2017, 18(1):295). It is assumed that the same rate of the composite safety endpoint (13% or 1.86% daily for 7 days) in the placebo and 20 mg montelukast arms and increasing to 14% and 15% for the 60 mg and 120 mg arms. It is assumed a dose-dependent effect of montelukast, and it is considered a maximum effect size (i.e., most AKI reduction/smallest odds ratio) of 0.74. This corresponds to a reduction in the incidence of any AKI from 30% to 24% (6 percentage point reduction, or 20% relative reduction), a clinically significant effect that would provide good evidence that montelukast impacts CSA-AKI. 580 participants provide 80% power to detect this effect. This power estimate is conservative since the ordinal AKI event rates in the trial will likely be higher than the rates in the preliminary trials due to outcome enrichment (restricting recruitment to those with AKI risk factors). In contrast, if the incidence of moderate/severe AKI were the primary outcome, only 18% power would be available to detect this treatment effect (OR: 0.74 with baseline AKI rate of 7.5%), or 6,000 subjects would be needed to have 80% power. The clinically relevant longitudinal AKI ordinal outcome scale based on KDIGO criteria has distinct statistical advantages for measuring treatment effects over AKI sensitivity outcomes. Statistical simulations were also used to model the adaptive nature of the trial. If there is no dose effect on AKI but increased toxicity, the lowest dose level of montelukast achieves the largest allocation. In contrast, if increasing dose increases AKI reduction, the 120 mg dose level achieves the largest allocation, even with marginally increased toxicity. Actual rates of AKI and toxicity in the trial will determine dose allocation and results.

Example 7

Testing the Hypothesis that Perioperative Montelukast Treatment Impacts Systemic and Renal Inflammation During Cardiac Surgery The effects of oral montelukast on leukocytes isolated from study participants, urinary markers of leukotriene signaling, and systemic markers of inflammation will be measured in order to measure mechanisms of CYSLTR activity, connect CYSLTR antagonism with urinary markers of tubular injury and clinical efficacy/safety outcomes measured in Example 6, and generate evidence about the role of renal and systemic inflammation in development of CSA-AKI. This will test the current hypothesis and may identify additional therapeutic targets for future investigation. The pharmacokinetic profile of perioperative oral montelukast will be determined at 3 doses in cardiac surgery patients to establish feasibility of this therapeutic/indication pairing. rs139639671/1123T in CYSLTR will be genotyped and compared to systemic and renal inflammation makers and clinical endpoints in montelukast and placebo groups. This will further establish that the missense SNP identified in the PheWAS results is a gain of function for CYSLTR, increases LT signaling, increases inflammation, and may lead to CSA-AKI.

A key mechanistic question is the source of leukotrienes post-cardiac surgery. $LTC_4$ and $LTD_4$ are produced locally in tissues but then are rapidly metabolized to $LTE_4$ locally and in the circulation which then undergoes mostly renal and less so hepatic clearance. Thus, urinary $LTE_4$ is a marker of whole-body leukotriene burden and urinary $LTC_4$ and $LTD_4$ better reflects local renal generation of leukotrienes. A rise in urinary $LTC_4$ and $LTD_4$ post-cardiac surgery which associates with AKI would reflect an intra-renal mechanism for leukotriene action. These actions may include alterations in renal inflammation and downstream tubular injury addressed in these studies on inflammation but would also raise the possibility of leukotriene mediated glomerular vasoconstriction which has been demonstrated in several animal models. Extra-renal leukotriene generation may still impact renal outcomes via systemic inflammation which will also be addressed in the studies of Example 6. In addition, leukotrienes exhibit feed forward behavior driving their own generation. A fall in urinary leukotriene levels in montelukast treated patients would point to a feed forward cycle. And finally, it has been noted that patients with higher LTE$_4$ levels have increased disease susceptibility and better response to montelukast, as was also noted in the preliminary study of LT expression in cardiac surgery patients herein.

Experimental methodology. Monocytes will be isolated using a magnetic cell isolation system (StemCell) and measure phospho-ERK, and phospho-IKK by ELISA as markers of monocyte activation (R&D Systems/Cell Signaling). Samples will be standardized by measurement of total ERK, p38, and IKK using ELISA. Cytokine measurements will be made using plasma and urine harvested pre-operatively, intraoperatively following cardiopulmonary bypass (CBP) and on days 1 and 3 post-operatively (TABLE 4). Concentrations of pro-inflammatory (TNFα, IL-6, IL-8, IL-1β), Th2 (IL-4, IL-13) and Th-17 (IL-17) cytokines in plasma and urine will be measured using a Magpix multi-cytokine array (Bio-Rad). Urinary cysteinyl leukotrienes will be measured with a validated, gold standard LC-MS (as opposed to ELISAs with specificity concerns) protocol (Montuschi et al., *J Chromatogr B Analyt Technol Biomed Life Sci.* 2014, 964:12-25). Creatinine will be measured in urine samples to normalize urinary cytokine and LT concentrations.

TABLE 4

Pharmacokinetics, pharmacodynamics, tubular injury markers

| Specimen | | Anesthetic induction | Following CPB | ICU admit | POD 1 | POD 2 | POD 3 | POD 4 |
|---|---|---|---|---|---|---|---|---|
| Montelukast plasma | Plasma | √ | √ | √ | √ | √ | √ | √ |
| rs139639671/I123T SNP | DNA | √ | | | | | | |
| Inflammatory pathways | WBCs | √ | √ | | √ | | | |
| T$_H$2, T$_H$17, and additional | Plasma/U | √ | √ | | √ | | √ | |
| LTC$_4$, LTD$_4$, and LTE$_4$ | Urine | √ | √ | √ | √ | | √ | |
| IGFBP7/TIMP-2, NGAL | Urine | √ | √ | √ | √ | √ | | |

The effects of treatment on these markers will be quantified using summary and longitudinal regression methods similar to those described for the primary outcome, and a series of analyses will be implemented to explore the associations between these markers over time and stratified by clinical conditions (e.g., by AKI).

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the disclosure are set out in the following numbered clauses:

Clause 1. A method of treating or reducing the severity of a cardiac surgery-associated acute kidney injury (CSA-AKI) in a subject in need thereof, the method comprising administering to the subject a therapeutically effective amount of a compound of Formula I:

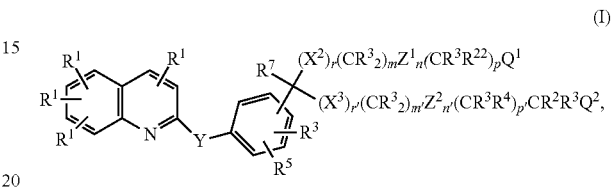

(I)

or a pharmaceutically acceptable esters or salts thereof, where: $R^1$ is H, halogen, —CF$_3$, —CN, —NO$_2$, or N$_3$; $R^2$ is lower alkyl, lower alkenyl, lower alkynyl, —CF$_3$, —CH$_2$F, —CHF$_2$, CH$_2$CF$_3$, substituted or unsubstituted phenyl, substituted or unsubstituted benzyl, substituted or unsubstituted 2-phenethyl, or two $R^2$ groups joined to the same carbon to form a carbocyclic ring of up to 8 members; $R^3$ is H or $R^2$; $R^4$ is halogen, —NO$_2$, —CN, —OR$^3$, —SR$^3$, NR$^3$R$^3$, NR$^3$C(O)R$^7$, or $R^3$; $R^5$ is H, halogen, —NO$_2$, —N$_3$, —CN, —SR$^2$, —NR$^3$R$^3$, —OR$^3$, lower alkyl, or —C(O)R$^3$; $R^5$ is —(CH$_2$)$_s$—C(R$^7$R$^7$)—(CH$_2$)$_s$—R$^8$ or —CH$_2$C(O)NR$^{12}$R$^{12}$; $R^7$ is H or C$_1$-C$_4$ alkyl; $R^8$ is the radical W—R$^9$; $R^9$ contains up to 20 carbon atoms and is (1) an alkyl group or (2) an alkylcarbonyl group of an organic acyclic or monocyclic carboxylic acid; $R^{11}$ is lower alkyl, —C(O)R$^{14}$, unsubstituted phenyl, or unsubstituted benzyl; $R^{12}$ is H or $R^{11}$; $R^{13}$ is lower alkyl, lower alkenyl, lower alkynyl, —CF$_3$ or substituted or unsubstituted phenyl, benzyl, or 2-phenethyl; $R^{14}$ is H or $R^{13}$; $R^{16}$ is H, C$_1$-C$_4$ alkyl, or OH; $R^{17}$ is lower alkyl, lower alkenyl, lower alkynyl, or substituted or unsubstituted phenyl, benzyl, or 2-phenethyl; $R^{18}$ is lower alkyl, lower alkenyl, lower alkynyl, —CF3 or substituted or unsubstituted phenyl, benzyl, or 2-phenethyl; $R^{19}$ is lower alkyl, lower alkenyl, lower alkynyl, —CF$_3$ or substituted or unsubstituted phenyl, benzyl, or 2-phenethyl; $R^{21}$ is H or $R^{17}$; $R^{22}$ is $R^4$, CHR$^7$ OR$^3$, or CHR$^7$SR$^2$; m is 0-8; m' is 2 or 3; n and n' are independently 0 or 1, p and p' are independently 0-8; m+n+p is 1-10 when r is 1 and X$_2$ is O, S, S(O), or S(O)$_2$; m+n+p is 0-10 when r is 1 and X$_2$ is CR$^3$R$^{16}$; m+n+p is 0-10 when r is 0; m'+n'+p' is 2-10; r and r are independently 0 or 1; s is 0-3; Q$^1$ is —C(O)OR$^3$, 1 H (or 2H)-tetrazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O) NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH; Q$^2$ is OH; W is O, S, or NR$^3$; X$^2$ and X$^3$ are independently O, S, S(O), S(O)$_2$, or CR$^3$ R$^{16}$; with the proviso that at least one is S or SO$_2$; Y is —CR$^3$=CR$^3$—Z$^1$ and Z$^2$ are independently -HET(-R$^3$—R$^5$)—; HET is the diradical of a benzene, a pyridine, a furan, or a thiophene; and, wherein the compound decreases urinary leukotrienes.

Clause 2. The method of clause 1, wherein the compound is administered in the form of a composition wherein the composition comprises a pharmaceutically acceptable carrier.

Clause 3. The method of any one of the preceding clauses, wherein the compound is montelukast or a pharmaceutically acceptable salt thereof.

Clause 4. The method of any one of the preceding clauses, wherein the compound is a pharmaceutically acceptable salt of montelukast.

Clause 5. The method of any one of clauses 2-4, wherein the composition comprises about 5 mg to about 250 mg of the compound.

Clause 6. The method of any one of the preceding clauses, wherein the subject is administered about 10 mg of the compound perioperatively.

Clause 7. The method of any one of clauses 1-5, wherein the subject is administered about 100 mg of the compound perioperatively through postoperative day 4.

Clause 8. The method of any one of the preceding clauses, wherein the subject is administered about 10 mg of the compound postoperatively.

Clause 9. The method of any one of clauses 7-8, wherein the subject is administered about 10 mg of the compound on postoperative day 5.

Clause 10. The method of any one of the preceding clauses, wherein the compound is administered at least 3 days preoperatively.

Clause 11. The method of any one of the preceding clauses, wherein the compound is administered perioperatively.

Clause 12. The method of any one of the preceding clauses, wherein the compound is administered at least 6 days postoperatively.

Clause 13. The method of any one of the preceding clauses, wherein the compound is administered orally or intravenously.

Clause 14. The method of any one of the preceding clauses, wherein the compound is administered at least 1× per day.

Clause 15. The method of any one of the preceding clauses, wherein the subject has a single nucleotide polymorphism (SNP) in the gene CYSTLR1.

Clause 16. The method of clause 15, wherein the SNP is rs139639671 or I123T.

Clause 17. The method of any one of the preceding clauses, wherein the subject has been identified as having an elevated level of serum creatinine, plasma creatinine, or urine creatinine, compared to baseline creatinine levels in the subject or a healthy control subject.

Clause 18. The method of any one of the preceding clauses, wherein urinary cysteinyl leukotriene levels are decreased following administration of the compound.

Clause 19. The method of any one of the preceding clauses, wherein one or more of urinary LTC4, LTD4, LTE4 levels are decreased following administration of the compound.

Clause 20. A method of treating or reducing the severity of an extracorporeal membrane oxygenation-associated acute kidney injury (ECMO-AKI) in a subject in need thereof, the method comprising administering to the subject a therapeutically effective amount of a compound of Formula I:

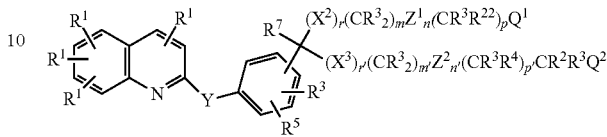

(I), or a pharmaceutically acceptable esters or salts thereof, where: R$^1$ is H, halogen, —CF$_3$, —CN, —NO$_2$, or N$_3$; R$^2$ is lower alkyl, lower alkenyl, lower alkynyl, —CF$_3$, —CH$_2$F, —CHF$_2$, CH$_2$CF$_3$, substituted or unsubstituted phenyl, substituted or unsubstituted benzyl, substituted or unsubstituted 2-phenethyl, or two R$^2$ groups joined to the same carbon to form a carbocyclic ring of up to 8 members; R$^3$ is H or R$^2$; R$^4$ is halogen, —NO$_2$, —CN, —OR$^3$, —SR$^3$, NR$^3$R$^3$, NR$^3$C (O)R$^7$, or R$^3$; R$^5$ is H, halogen, —NO$_2$, —N$_3$, —CN, —SR$^2$, —NR$^3$R$^3$, —OR$^3$, lower alkyl, or —C(O)R$^3$; R$^6$ is —(CH$_2$)$_s$ —C(R$^7$R$^7$)—(CH$_2$)$_s$—R$^8$ or —CH$_2$C(O)NR$^{12}$R$^{12}$; R$^7$ is H or C$_1$-C$_4$ alkyl; R$^8$ is the radical W—R$^9$; R$^9$ contains up to 20 carbon atoms and is (1) an alkyl group or (2) an alkylcarbonyl group of an organic acyclic or monocyclic carboxylic acid; R$^{11}$ is lower alkyl, —C(O)R$^{14}$, unsubstituted phenyl, or unsubstituted benzyl; R$^{12}$ is H or R$^{11}$; R$^{13}$ is lower alkyl, lower alkenyl, lower alkynyl, —CF3 or substituted or unsubstituted phenyl, benzyl, or 2-phenethyl; R$^{14}$ is H or R$^{13}$; R$^{16}$ is H, C$_1$-C$_4$ alkyl, or OH; R$^{17}$ is lower alkyl, lower alkenyl, lower alkynyl, or substituted or unsubstituted phenyl, benzyl, or 2-phenethyl; R$^{18}$ is lower alkyl, lower alkenyl, lower alkynyl, —CF3 or substituted or unsubstituted phenyl, benzyl, or 2-phenethyl; R$^{19}$ is lower alkyl, lower alkenyl, lower alkynyl, —CF$_3$ or substituted or unsubstituted phenyl, benzyl, or 2-phenethyl; R$^{21}$ is H or R$^{17}$; R$^{22}$ is R$^4$, CHR$^7$ OR$^3$, or CHR$^7$SR$^2$; m is 0-8; m' is 2 or 3; n and n' are independently 0 or 1, p and p' are independently 0-8; m+n+p is 1-10 when r is 1 and X$_2$ is O, S, S(O), or S(O)$_2$; m+n+p is 0-10 when r is 1 and X$_2$ is CR$^3$R$^{16}$; m+n+p is 0-10 when r is 0; m'+n'+p' is 2-10; r and r' are independently 0 or 1; s is 0-3; Q$^1$ is —C(O)OR$^3$, 1H (or 2H)-tetrazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O) NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH; Q$^2$ is OH; W is O, S, or NR$^3$; X$^2$ and X$^3$ are independently O, S, S(O), S(O)$_2$, or CR$^3$ R$^{16}$; with the proviso that at least one is S or SO$_2$; Y is —CR$^3$=CR$^3$—, Z$^1$ and Z$^2$ are independently -HET(-R$^3$—R$^5$)—; HET is the diradical of a benzene, a pyridine, a furan, or a thiophene; and, wherein the compound decreases urinary leukotrienes.

Clause 21. The method of clause 20, wherein the compound is administered in the form of a composition wherein the composition comprises a pharmaceutically acceptable carrier.

Clause 22. The method of any one of the preceding clauses, wherein the compound is montelukast or a pharmaceutically acceptable salt thereof.

Clause 23. The method of any one of the preceding clauses, wherein the compound is a pharmaceutically acceptable salt of montelukast.

Clause 24. The method of any one of clauses 21-23, wherein the composition comprises about 5 mg to about 250 mg of the compound.

Clause 25. The method of any one of the preceding clauses, wherein the subject is administered the compound at least 2 hours prior to connecting an ECMO machine to the subject.

Clause 26. The method of clause 24, wherein the subject is administered about 100 mg of the compound prior to and throughout the duration of being connected to the ECMO machine.

Clause 27. The method of clause 24, wherein the subject is administered about 10 mg of the compound prior to and throughout the duration of being connected to the ECMO machine.

Clause 28. The method of any one of the preceding clauses, wherein the compound is administered orally or intravenously.

Clause 29. The method of any one of the preceding clauses, wherein the compound is administered at least 1× per day.

Clause 30. The method of any one of the preceding clauses, wherein the subject has a single nucleotide polymorphism (SNP) in the gene CYSTLR1.

Clause 31. The method of clause 30, wherein the SNP is rs139639671 or I123T.

Clause 32. The method of any one of the preceding clauses, wherein the subject has been identified as having an elevated level of serum creatinine, plasma creatinine, or urine creatinine, compared to baseline creatinine levels in the subject or a healthy control subject.

Clause 33. The method of any one of the preceding clauses, wherein urinary cysteinyl leukotriene levels are decreased following administration of the compound.

Clause 34. The method of any one of the preceding clauses, wherein one or more of urinary LTC4, LTD4, LTE4 levels are decreased following administration of the compound.

The invention claimed is:

1. A method of treating or reducing the severity of a cardiac surgery-associated acute kidney injury (CSA-AKI) in a subject in need thereof, the method comprising administering to the subject a therapeutically effective amount of a compound of Formula I:

(I)

$$\begin{array}{c}\text{structure with substituents } R^1, R^2, R^3, R^5, R^7, Y, \\ (X^2)_r(CR^3{}_2)_m Z^1{}_n(CR^3R^{22})_p Q^1, \\ (X^3)_{r'}(CR^3{}_2)_{m'} Z^2{}_{n'}(CR^3R^4)_{p'} CR^2R^3 Q^2\end{array}$$

or a pharmaceutically acceptable ester or salt thereof, where:

$R^1$ is H, halogen, —$CF_3$, —CN, —$NO_2$, or $N_3$;

$R^2$ is lower alkyl, lower alkenyl, lower alkynyl, —$CF_3$, —$CH_2F$, —$CHF_2$, $CH_2CF_3$, substituted or unsubstituted phenyl, substituted or unsubstituted benzyl, substituted or unsubstituted 2-phenethyl, or two $R^2$ groups joined to the same carbon to form a carbocyclic ring of up to 8 members;

$R^3$ is H or $R^2$;

$R^4$ is halogen, —$NO_2$, —CN, —$OR^3$, —$SR^3$, $NR^3R^3$, $NR^3C(O)R^7$, or $R^3$;

$R^5$ is H, halogen, —$NO_2$, —$N_3$, —CN, —$SR^2$, —$NR^3R^3$, —$OR^3$, lower alkyl, or —$C(O)R^3$;

$R^6$ is —$(CH_2)_s$—$C(R^7R^7)$—$(CH_2)_s$—$R^6$ or —$CH_2C(O)NR^{12}R^{12}$;

$R^7$ is H or $C_1$-$C_4$ alkyl;

$R^8$ is the radical W—$R^9$;

$R^9$ contains up to 20 carbon atoms and is (1) an alkyl group or (2) an alkylcarbonyl group of an organic acyclic or monocyclic carboxylic acid;

$R^{11}$ is lower alkyl, —$C(O)R^{14}$, unsubstituted phenyl, or unsubstituted benzyl;

$R^{12}$ is H or $R^{11}$;

$R^{13}$ is lower alkyl, lower alkenyl, lower alkynyl, —$CF_3$ or substituted or unsubstituted phenyl, benzyl, or 2-phenethyl;

$R^{14}$ is H or $R^{13}$;

$R^{16}$ is H, $C_1$-$C_4$ alkyl, or OH;

$R^{17}$ is lower alkyl, lower alkenyl, lower alkynyl, or substituted or unsubstituted phenyl, benzyl, or 2-phenethyl;

$R^{18}$ is lower alkyl, lower alkenyl, lower alkynyl, —CF3 or substituted or unsubstituted phenyl, benzyl, or 2-phenethyl;

$R^{19}$ is lower alkyl, lower alkenyl, lower alkynyl, —$CF_3$ or substituted or unsubstituted phenyl, benzyl, or 2-phenethyl;

$R^{21}$ is H or $R^{17}$; —$R^{22}$ is $R^4$, $CHR^7$ $OR^3$, or $CHR^7SR^2$;

m is 0-8;

m' is 2 or 3;

n and n' are independently 0 or 1, p and p' are independently 0-8;

m+n+p is 1-10 when r is 1 and $X_2$ is O, S, S(O), or $S(O)_2$;

m+n+p is 0-10 when r is 1 and $X_2$ is $CR^3R^8$;

m+n+p is 0-10 when r is 0;

m'+n'+p' is 2-10;

r and r' are independently 0 or 1;

s is 0-3;

$Q^1$ is —$C(O)OR^3$, 1H (or 2H)-tetrazol-5-yl, —$C(O)OR^G$, —$C(O)NHS(O)_2R^{13}$, —CN, —$C(O)NR^{12}R^{12}$, $NR^{21}S(O)_2R^{13}$, —$NR^{12}C(O)NR^{12}R^{12}$, —$NR^{21}C(O)R^{18}$, —$OC(O)NR^{12}R^{12}$, —$C(O)R^{19}$, —$S(O)R^{18}$, —$S(O)_2R^{18}$, —$S(O)_2NR^{12}R^{12}$, —$NO_2$, —$NR^{21}C(O)OR^{17}$, —$C(NR^{12}R^{12})$=$NR^{12}$, —$C(R^{13})$=NOH;

$Q^2$ is OH;

W is O, S, or $NR^3$;

$X^2$ and $X^3$ are independently O, S, S(O), $S(O)_2$, or $CR^3R^{16}$; with the proviso that at least one is S or $SO_2$;

Y is —$CR^3$=$CR^3$—

$Z^1$ and $Z^2$ are independently -HET($R^3$)($R^5$)—;

HET is the diradical of a benzene, a pyridine, a furan, or a thiophene; and, wherein the compound decreases urinary leukotrienes.

2. The method of claim 1, wherein the compound is administered in the form of a composition wherein the composition comprises a pharmaceutically acceptable carrier.

3. The method of claim 2, wherein the composition comprises about 5 mg to about 250 mg of the compound.

4. The method of claim 1, wherein the compound is montelukast or a pharmaceutically acceptable salt of montelukast.

5. The method of claim 4, wherein the pharmaceutically acceptable salt of montelukast is montelukast sodium.

6. The method of claim 1, wherein the subject is administered the compound perioperatively, the subject is administered the compound perioperatively through at least postoperative day 7, the subject is administered the compound postoperatively, and/or the compound is administered to the subject at least 3 days preoperatively.

7. The method of claim 1, wherein the compound is administered orally or intravenously at least once per day.

8. The method of claim 1, wherein the subject has a single nucleotide polymorphism (SNP) in the gene CYSTLR1.

9. The method of claim 8, wherein the SNP is rs139639671 or I123T.

10. The method of claim 1, wherein the subject has been identified as having an elevated level of serum creatinine, plasma creatinine, or urine creatinine, compared to baseline creatinine levels in the subject or a healthy control subject.

11. The method of claim 1, wherein urinary cysteinyl leukotriene levels are decreased in the subject following administration of the compound.

12. The method of claim 1, wherein one or more of urinary $LTC_4$, $LTD_4$, and $LTE_4$ levels are decreased in the subject following administration of the compound.

13. A method of treating or reducing the severity of an extracorporeal membrane oxygenation-associated acute kidney injury (ECMO-AKI) in a subject in need thereof, the method comprising administering to the subject a therapeutically effective amount of a compound of Formula I:

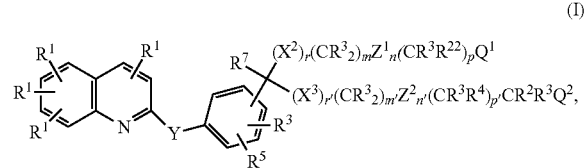

(I)

or a pharmaceutically acceptable ester or salt thereof, where:

$R^1$ is H, halogen, —$CF_3$, —CN, —$NO_2$, or $N_3$;

$R^2$ is lower alkyl, lower alkenyl, lower alkynyl, —$CF_3$, —$CH_2F$, —$CHF_2$, $CH_2CF_3$, substituted or unsubstituted phenyl, substituted or unsubstituted benzyl, substituted or unsubstituted 2-phenethyl, or two $R^2$ groups joined to the same carbon to form a carbocyclic ring of up to 8 members;

$R^3$ is H or $R^2$;

$R^4$ is halogen, —$NO_2$, —CN, —$OR^3$, —$SR^3$, $NR^3R^3$, $NR^3C(O)R^7$, or $R^3$;

$R^5$ is H, halogen, —$NO_2$, —$N_3$, —CN, —$SR^2$, —$NR^3R^3$, —$OR^3$, lower alkyl, or —$C(O)R^3$;

$R^6$ is —$(CH_2)_s$—$C(R^7R^7)$—$(CH_2)_s$—$R^8$ or —$CH_2C(O)NR^{12}R^{12}$;

$R^7$ is H or $C_1$-$C_4$ alkyl;

$R^8$ is the radical W—$R^9$;

$R^9$ contains up to 20 carbon atoms and is (1) an alkyl group or (2) an alkylcarbonyl group of an organic acyclic or monocyclic carboxylic acid;

$R^{11}$ is lower alkyl, —$C(O)R^{14}$, unsubstituted phenyl, or unsubstituted benzyl;

$R^{12}$ is H or $R^{11}$;

$R^{13}$ is lower alkyl, lower alkenyl, lower alkynyl, —$CF_3$ or substituted or unsubstituted phenyl, benzyl, or 2-phenethyl;

$R^{14}$ is H or $R^{13}$;

$R^{16}$ is H, $C_1$-$C_4$ alkyl, or OH;

$R^{17}$ is lower alkyl, lower alkenyl, lower alkynyl, or substituted or unsubstituted phenyl, benzyl, or 2-phenethyl;

$R^{18}$ is lower alkyl, lower alkenyl, lower alkynyl, —CF3 or substituted or unsubstituted phenyl, benzyl, or 2-phenethyl;

$R^{19}$ is lower alkyl, lower alkenyl, lower alkynyl, —$CF_3$ or substituted or unsubstituted phenyl, benzyl, or 2-phenethyl;

$R^{21}$ is H or $R^{17}$—;

$R^{22}$ is $R^4$, $CHR^7$ $OR^3$, or $CHR^7SR^2$;

m is 0-8;

m' is 2 or 3;

n and n' are independently 0 or 1, p and p' are independently 0-8;

m+n+p is 1-10 when r is 1 and $X_2$ is O, S, S(O), or $S(O)_2$;

m+n+p is 0-10 when r is 1 and $X_2$ is $CR^3R^8$;

m+n+p is 0-10 when r is 0;

m'+n'+p' is 2-10;

r and r' are independently 0 or 1;

s is 0-3;

$Q^1$ is —$C(O)OR^3$, 1H (or 2H)-tetrazol-5-yl, —$C(O)OR^G$, —$C(O)NHS(O)_2R^{13}$, —CN, —$C(O)NR^{12}R^{12}$, $NR^{21}S(O)_2R^{13}$, —$NR^{12}C(O)NR^{12}R^{12}$, —$NR^{21}C(O)R^{18}$, —$OC(O)NR^{12}R^{12}$, —$C(O)R^{19}$, —$S(O)R^{18}$, —$S(O)_2R^{18}$, —$S(O)_2NR^{12}R^{12}$, —$NO_2$, —$NR^{21}C(O)OR^{17}$, —$C(NR^{12}R^{12})$=$NR^{12}$, —$C(R^{13})$=NOH;

$Q^2$ is OH;

W is O, S, or $NR^3$;

$X^2$ and $X^3$ are independently O, S, S(O), $S(O)_2$, or $CR^3R^{16}$; with the proviso that at least one is S or $SO_2$;

Y is —$CR^3$=$CR^3$—

$Z^1$ and $Z^2$ are independently -HET($R^3$)($R^5$)—;

HET is the diradical of a benzene, a pyridine, a furan, or a thiophene; and, wherein the compound decreases urinary leukotrienes.

14. The method of claim 13, wherein the compound is administered in the form of a composition wherein the composition comprises a pharmaceutically acceptable carrier.

15. The method of claim 13, wherein the compound is montelukast or a pharmaceutically acceptable salt of montelukast.

16. The method of claim 15, wherein the pharmaceutically acceptable salt of montelukast is montelukast sodium.

17. The method of claim 15, wherein the composition comprises about 5 mg to about 250 mg of the compound.

18. The method of claim 13, wherein the subject is administered the compound at least 2 hours prior to connecting an ECMO machine to the subject, or wherein the subject is administered the compound prior to and throughout the duration of being connected to the ECMO machine.

19. The method of claim 13, wherein the compound is administered orally or intravenously at least once per day.

20. The method of claim 13, wherein the subject has a single nucleotide polymorphism (SNP) in the gene CYSTLR1.

21. The method of claim 20, wherein the SNP is rs139639671 or I123T.

22. The method of claim 13, wherein the subject has been identified as having an elevated level of serum creatinine, plasma creatinine, or urine creatinine, compared to baseline creatinine levels in the subject or a healthy control subject.

23. The method of claim 13, wherein urinary cysteinyl leukotriene levels are decreased in the subject following administration of the compound.

24. The method of claim 13, wherein one or more of urinary $LTC_4$, $LTD_4$, and $LTE_4$ levels are decreased in the subject following administration of the compound.

* * * * *